US009926347B2

(12) United States Patent
Alper et al.

(10) Patent No.: US 9,926,347 B2
(45) Date of Patent: *Mar. 27, 2018

(54) METHODS FOR ENGINEERING SUGAR TRANSPORTER PREFERENCES

(71) Applicant: Board of Regents, The University of Texas System, Austin, TX (US)

(72) Inventors: Hal Alper, Austin, TX (US); Eric Young, Arlington, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/034,772

(22) PCT Filed: Nov. 5, 2014

(86) PCT No.: PCT/US2014/064168
§ 371 (c)(1),
(2) Date: May 5, 2016

(87) PCT Pub. No.: WO2015/069796
PCT Pub. Date: May 14, 2015

(65) Prior Publication Data
US 2016/0280745 A1  Sep. 29, 2016

Related U.S. Application Data

(60) Provisional application No. 61/900,115, filed on Nov. 5, 2013.

(51) Int. Cl.
C07K 14/40 (2006.01)
C12P 7/10 (2006.01)
C07K 14/39 (2006.01)

(52) U.S. Cl.
CPC .............. *C07K 14/40* (2013.01); *C07K 14/39* (2013.01); *C12P 7/10* (2013.01); *Y02E 50/16* (2013.01)

(58) Field of Classification Search
None
See application file for complete search history.

(56) References Cited

U.S. PATENT DOCUMENTS

| 7,910,718 B2 | 3/2011 | Simikin et al. |
| 2010/0017904 A1 | 1/2010 | Abad et al. |
| 2011/0020910 A1 | 1/2011 | Glass et al. |
| 2011/0195448 A1 | 8/2011 | Lippmeier et al. |
| 2012/0329109 A1 | 12/2012 | Chua et al. |
| 2015/0344532 A1* | 12/2015 | Alper ............... C07K 14/33 435/254.21 |
| 2016/0280745 A1* | 9/2016 | Alper ............... C07K 14/40 |

FOREIGN PATENT DOCUMENTS

| WO | WO-2012/097091 A2 | 7/2012 |
| WO | WO-2012/097091 A3 | 7/2012 |
| WO | WO-2013/155481 A1 | 10/2013 |
| WO | 2014018552 A1 | 1/2014 |
| WO | 2015179701 A1 | 11/2015 |

OTHER PUBLICATIONS

Davis, E.O. et al. (Oct. 15, 1987). "The cloning and DNA sequence of the gene xylE for xylose-proton symport in *Escherichia coli* K12," *J Biol Chem* 262(29):13928-13932.
Du, J. et al. (Nov. 2010, e-published Aug. 11, 2010). "Discovery and characterization of novel d-xylose-specific transporters from Neurospora crassa and Pichia stipites," *Mol Biosyst* 6(11):2150-2156.
GenBank Accession No. CAI44932.1, created on Oct. 24, 2006, located at <http://ww.ncbi.nlm.nih.gov/protein/CAI44932.1>, last visited Nov. 29, 2016, 2 pages.
Hamacher, T. et al. (2002). "Characterization of the xylose-transporting properties of yeast hexose transporters and their influence on xylose utilization," *Microbiology* 148(pt.9):2783-2788.
International Search Report dated Feb. 4, 2015, for PCT Application No. PCT/US2014/064168, filed Nov. 5, 2014, 3 pages.
Kasahara, T. et al. (Oct. 11, 2011, e-published Sep. 13, 2011). "Crucial effects of amino acid side chain length in transmembrane segment 5 on substrate affinity in yeast glucose transporter Hxt7," *Biochemistry* 50(40):8674-8681.
Saloheimo, A. et al. (Apr. 2007, e-published Dec. 19, 2006). "Xylose transport studies with xylose-utilizing *Saccharomyces cerevisiae* strains expressing heterologous and homologous permeases" *Appl Microbiol Biotechnol* 74(5):1041-1052.
Subtil, T. et al. (Oct. 12, 2011). "Improving L-arabinose utilization of pentose fermenting *Saccharomyces cerevisiae* cells by heterologous expression of L-arabinose transporting sugar transporters," *Biotechnol Biofuels* 4:38.
Sun, L. et al. (Oct. 18, 2012). "Crystal structure of a bacterial homologue of glucose transporters GLUT1-4," *Nature* 490(7420):361-366.
Wieczorke, R. et al. (Dec. 31, 1999). "Concurrent knock-out of at least 20 transporter genes is required to block uptake of hexoses in *Saccharomyces cerevisiae*," *FEBS Lett* 464(3):123-128.
Written Opinion dated Feb. 4, 2015, for PCT Application No. PCT/US2014/064168, filed Nov. 5, 2014, 5 pages.
Young, E. et al. (May 2011, e-published Mar. 18, 2011). "Functional survey for heterologous sugar transport proteins, using *Saccharomyces cerevisiae* as a host," *Appl Environ Microbiol* 77(10):3311-3319.
Young, E.M. et al. (Jul. 2012, e-published Mar. 18, 2012). "A molecular transporter engineering approach to improving xylose catabolism in *Saccharomyces cerevisiae*," *Metab Eng* 14(4):401-411.

(Continued)

*Primary Examiner* — Hope Robinson
(74) *Attorney, Agent, or Firm* — Meunier Carlin & Curfman LLC

(57) ABSTRACT

Provided herein are compositions and methods useful for transporting xylose, arabinose and other monosaccharides, into a yeast cell.

5 Claims, 18 Drawing Sheets

(56) References Cited

OTHER PUBLICATIONS

Young, E.M. et al. (Jan. 7, 2014, e-published Dec. 16, 2013). "Rewiring yeast sugar transporter preference through modifying a conserved protein motif," *Proc Natl Acad Sci USA* 111(1):131-136.
Bengtsson, O. et al. (Nov. 2008). "Identification of common traits in improved xylose-growing *Saccharomyces cerevisiae* for inverse metabolic engineering," 25(11):835-847.
Curran, K.A. et al. (Jul. 2012). "Expanding the chemical palate of cells by combining systems biology and metabolic engineering," Metab Eng 14(4):289-297.
International Search Report and Written Opinion dated Aug. 26, 2015, for PCT Application No. PCT/US2015/032058, filed May 21, 2015, 4 pages.
Wahlbom, C.F. et al. (Feb. 2003). "Molecular analysis of a *Saccharomyces cerevisiae* mutant with improved ability to utilize xylose shows enhanced expression of proteins involved in transport, initial xylose metabolism, and the pentose phosphate pathway," Appl Environ Microbiol 69(2):740-746.

* cited by examiner

METHODS FOR ENGINEERING SUGAR TRANSPORTER PREFERENCES

CROSS-REFERENCES TO RELATED APPLICATIONS

This application claims the benefit of U.S. Provisional Application No. 61/900,115, filed Nov. 5, 2013, which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant no. CBET 1067506 awarded by the National Science Foundation. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 93331-920858_ST25.TXT, created on Nov. 5, 2013, 12,049 bytes, machine format IBM-PC, MS-Windows operating system, is hereby incorporated by reference.

BACKGROUND OF THE INVENTION

The quest for an optimal xylose pathway in yeast is of utmost importance along the way to realizing the potential of lignocellulosic biomass conversion into fuels and chemicals. An often overlooked aspect of this catabolic pathway is the molecular transport of this sugar. Molecular transporter proteins facilitate monosaccharide uptake and serve as the first step in catabolic metabolism. In this capacity, the preferences, regulation, and kinetics of these transporters ultimately dictate total carbon flux. Optimization of intracellular catabolic pathways only increases the degree to which transport exerts control over metabolic flux. Thus, monosaccharide transport profiles and rates are important design criteria and a driving force to enable metabolic engineering advances. Among possible host organisms, *Saccharomyces cerevisiae* is an emerging industrial organism. However, *S. cerevisiae* lacks an endogenous xylose catabolic pathway and thus is unable to natively utilize the second most abundant sugar in lignocellulosic biomass, xylose. Decades of research have been focused on improving xylose catabolic pathways in recombinant *S. cerevisiae*, but little effort has been focused on the first committed step of the process—xylose transport, an outstanding limitation in the efficient conversion of lignocellulosic sugars. There is a need in the art for efficient transport systems for xylose in yeast. Provided herein are solutions to these and other problems in the art.

BRIEF SUMMARY OF THE INVENTION

Accordingly, provided herein, inter alia, are compositions and methods useful for transporting xylose, arabinose, galactose and other monosaccharides and polysaccharides into a yeast cell.

In a first aspect is a recombinant xylose transporter protein including a transporter motif sequence corresponding to amino acid residue positions 36, 37, 38, 39, 40, and 41 of *Candida intermedia* GXS1 protein. The transporter motif sequence is -G-G/F-$X^1$-$X^2$-$X^3$-G-. $X^1$ is D, C, G, H, I, L, or F. $X^2$ is A, D, C, E, G, H, or I. $X^3$ is N, C, Q, F, G, L, M, S, T, or P. The transporter motif sequence is not -G-G-L-I-F-G- or -G-G-F-I-F-G-.

In another aspect is a recombinant galactose-arabinose transporter protein including a transporter motif sequence corresponding to amino acid residue positions 36, 37, 38, 39, 40, and 41 of *Candida intermedia* GXS1 protein. The transporter motif sequence is -G-G/F-$X^4$-$X^5$-$X^6$-G-. $X^4$ is D, C, F, G, H, L, R, T, or P. $X^5$ is A, C, E, F, H, K, S, P, or V. $X^6$ is R, D, E, F, H, I, M, T, or Y. The sequence is not -G-G-L-V-Y-G-, or -G-G-F-V-F-G-.

Also provided herein are yeast cells that include a recombinant hexose or pentose transporter protein described herein. In one aspect the yeast cell includes a recombinant xylose transporter protein described herein. In another aspect the yeast cell includes a recombinant galactose-arabinose transporter described herein.

Provided herein are nucleic acid sequences that encode a recombinant hexose or pentose transporter protein described herein. In one aspect the nucleic acid encodes a recombinant xylose transporter protein described herein. In another aspect the nucleic acid encodes a recombinant galactose-arabinose transporter protein described herein.

Further provided herein are methods of transporting a hexose or pentose into a yeast cell using the recombinant transporter proteins described herein. In one aspect is a method of transporting xylose into a yeast cell by contacting a yeast cell having a recombinant xylose transporter protein described herein with a xylose compound described herein. The xylose transporter protein is allowed to transport the xylose compound into the yeast cell. In another aspect is a method of transporting galactose or arabinose into a yeast cell by contacting a yeast cell having a recombinant galactose-arabinose transporter protein described herein with a galactose compound or an arabinose compound described herein. The recombinant galactose-arabinose transporter protein is allowed to transport the galactose compound or the arabinose compound into the yeast cell.

DETAILED DESCRIPTION OF THE INVENTION

Figure 1:
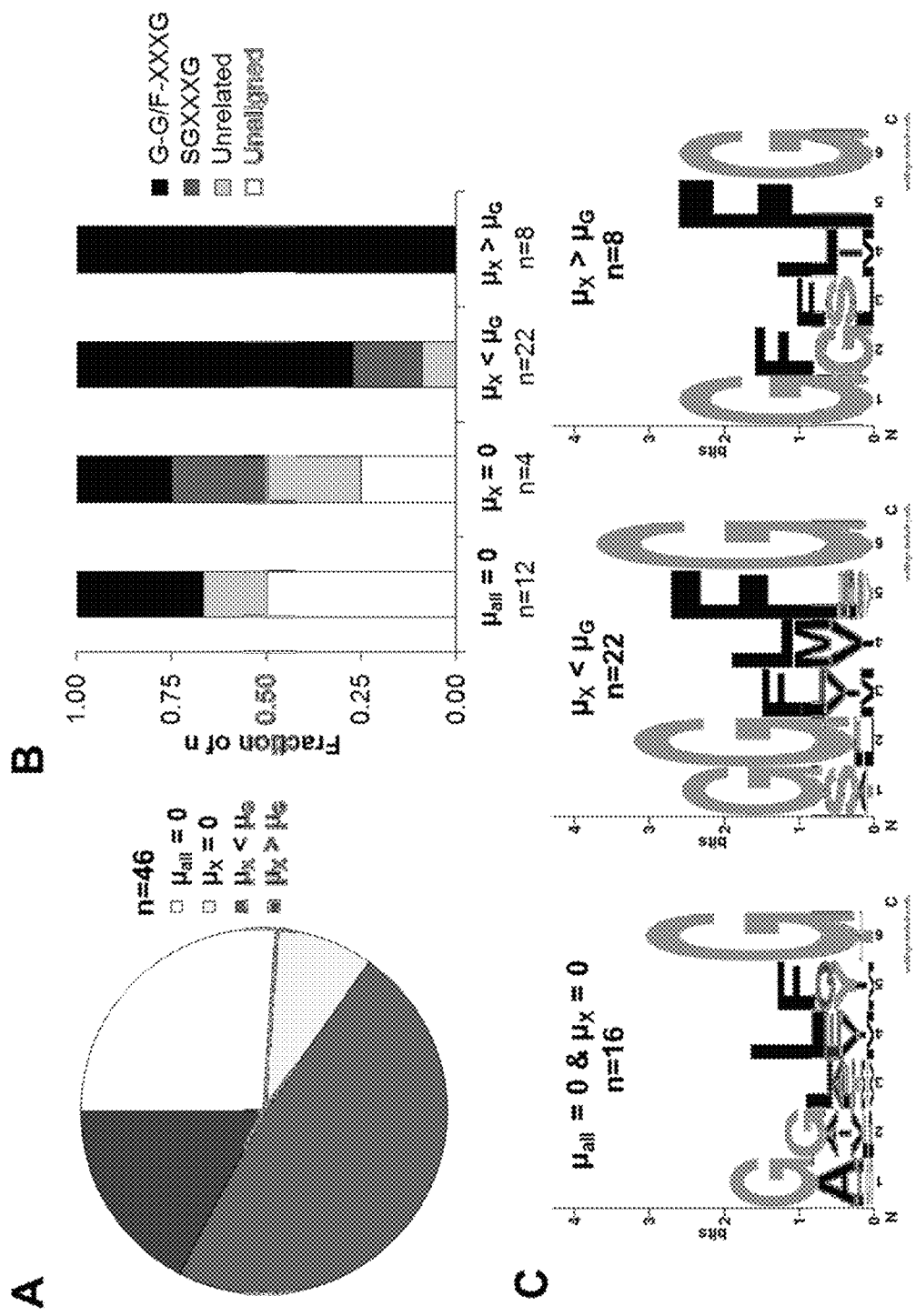
FIG. 1—Sequence categorization and phenotypic classification of native and heterologous transporters. A) The distribution of phenotypic classes for 46 cloned wild type major facilitator superfamily transporters. B) The distribution of each sequence category present in each phenotypic class. Transporters containing the conserved motif are enriched in the phenotypic classes that confer growth on xylose. C) Weblogos of the phenotypic classes illustrate enrichment of the G-G/F-XXXG motif in TMS1. Abbreviations: $\mu_{all}$=0: no growth the five carbon sources tested. $\mu_x$=0: growth on hexoses but not xylose. $\mu_x < \mu_G$: growth on xylose is less than that on glucose. $\mu_x > \mu_G$: growth on xylose is greater than that on glucose.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are well known and commonly used in the art for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference to, for example, a cell, nucleic acid, or protein, indicates that the cell, nucleic acid, or protein, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express genes otherwise modified from those found in the native form of a cell (e.g. genes encoding a mutation in a native or non-native transporter protein, such as a transporter motif sequence described herein). For example, a recombinant protein may be a protein that is expressed by a cell or organism that has been modified by the introduction of a heterologous nucleic acid (e.g. encoding the recombinant protein).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "yeast cell" as used herein, refers to a eukaryotic unicellular microorganism carrying out metabolic or other function sufficient to preserve or replicate its genomic DNA. Yeast cells may carry out fermentation of sugars described herein. Fermentation may convert the sugar to a biofuel or biochemical as set forth herein. Yeast cells referenced herein include, for example, the following species: *Kluyveromyces lactis, Torulaspora delbrueckii, Zygosaccharomyces rouxii, Saccharomyces cerevisiae, Yarrowia lipolytica, Candida intermedia, Cryptococcos neoformans, Debaryomyces hansenii, Phaffia rhodozyma,* or *Scheffersomyces stipitis.*

The term "biofuel" as used herein refers to a convenient energy containing substance produced from living organisms (e.g. biomass conversion to a fuel). Thus, biofuels may be produced through, for example, fermentation of carbohydrates (e.g. sugars) found in biomass (e.g. lignocellulosic biomass). Biofuels may be solid, liquid, or gas forms. Biofuels include, for example, ethanol, biodiesel, vegetable oil, ether (oxygenated fuels), or gas (e.g. methane).

The term "biochemical" as used herein refers to chemicals produced by living organisms. Biochemicals herein include alcohols (e.g. butanol, isobutanol, 2,3-butanediol, propanol); sugars (e.g. erythritol, mannitol, riboflavin); carotenoids (e.g. β-carotene, lycopene, astaxanthin); fatty acids (e.g. ricinoleic acid, linolenic acid, tetracetyl phytosphingosine); amino acids (e.g. valine, lysine, threonine); aromatics (e.g. indigo, vanillin, sytrene, p-hydroxystyrene); flavonoids (e.g. naringenin, genistein, kaempferol, quercetin, chrysin, apigenin, luteolin); stillbenoids (e.g. resveratrol); terpenoids (e.g. β-amyrin, taxadiene, miltiradiene, paclitaxel, artemisinin, bisabolane); polyketides (e.g. aureothin, spectinabilin, lovastatin, geodin); or organic acids (e.g. citric acid, succinic acid, malic acid, lactic acid, polylactic acid, adipic acid, glucaric acid) produced by living organisms (e.g. a yeast cell). See e.g. Curran K. A., Alper H. S., Metabolic Engineering 14:289-297 (2012).

A "transporter motif sequence" as used herein refers to an amino acid sequence that, when present in a protein (e.g. a sugar transporter protein such as a MFS transporter protein), increases the ability of the protein to transport a sugar or sugar-containing compound into a yeast cell. The transporter motif sequence may impart a hexose sugar transport preference or pentose sugar transport preference to the protein. Thus, for example, the transporter motif sequence may impart preference to hexose sugars to a transporter protein, thereby allowing the transporter protein to preferentially transport hexoses into a yeast cell. The transporter motif sequence may impart preference to a single hexose (e.g. galactose). The transporter motif sequence may impart preference to more than one hexose sugar (galactose and mannose). The transporter motif sequence may impart preference to pentose sugars to a transporter protein, thereby allowing the transporter protein to preferentially transport pentose into a yeast cell. The transporter motif sequence may impart preference to a single pentose (e.g. xylose). The transporter motif sequence may impart preference to more than one pentose sugar (e.g. xylose and arabinose). The transporter motif sequence may impart preference for at least two sugars (e.g. galactose and arabinose).

The transporter motif sequence described herein corresponds to residues corresponding to positions 36-41 of the *Candida intermedia* GXS1 protein ("GXS1 motif sequence"). One skilled in the art will immediately recognize the identity and location of residues corresponding to positions 36-41 of the *Candida intermedia* GXS1 protein in other transporter proteins with different numbering systems. For example, by performing a simple sequence alignment with *Candida intermedia* GXS1 protein the identity and location of residues corresponding to positions 36-41 of the *Candida intermedia* GXS1 protein are identified in other yeast transport proteins as illustrated in FIGS. 19 and 20. Insertion (e.g. substitution) of a transporter motif sequence into a yeast transport protein may thereby be performed resulting in a functional yeast transporter protein with an altered sugar transport preference (e.g. changing a preference for hexoses to a preference for pentoses). For example, amino acid residue positions 75-81 of *S. cerevisiae* HXT7 protein correspond to amino acid residue positions 36-41 of the *Candida intermedia* GXS1 protein. See e.g. Example 2 and SEQ ID NO:1.

SEQ ID NO: 1

```
  1   MGLEDNRMVKRFVNVGEKKAGSTAMAIIVGLFAASGGVLFGYDTGTISGVMTMDYVLARY   60

61   PSNKHSFTADESSLIVSILSVGIFFGALCAPFLNDTLGRRWCLILSALIVFNIGAILQVI  120

121   STAIPLLCAGRVIAGFGVGLISATIPLYQSETAPKWIRGAIVSCYQWAITIGLFLASCVN  180

181   KGTEHMTNSGSYRIPLAIQCLWGLILGIGMIFLPETPRFWISKGNQEKAAESLARLRKLP  240
```

-continued

```
241   IDHPDSLEELRDITAAYEFETVYGKSSWSQVFSHKNHQLKRLFTGVAIQAFQQLTGVNFI  300

301   FYYGTTFFKRAGVNGFTISLATNIVNVGSTIPGILLMEVLGRRNMLMGGATGMSLSQLIV  360

361   AIVGVATSENNKSSQSVLVAFSCIFIAFFAATWGPCAWVVVGELFPLRTRAKSVSLCTAS  420

421   NWLWNWGIAYATPYMVDEDKGNLGSNVFFIWGGFNLACVFFAWYFIYETKGLSLEQVDEL  480

481   YEHVSKAWKSKGFVPSKHSFREQVDQQMDSKTEAIMSEEASV                    522
```

A "transporter protein" as used herein refers to a transmembrane protein which transports sugars (e.g. hexoses and pentoses) into a yeast cell. The transporter protein may be a yeast transporter protein. The transporter protein may be a transporter protein belonging to the major faciliator superfamily ("MFS") transporter proteins. A transporter protein may transport a hexose (e.g. galactose) into a yeast cell. A transporter protein may transport a pentose (e.g. xylose or arabinose) into a yeast cell. A transporter protein may be engineered, using the transporter motif sequences described herein, to alter its sugar preference (e.g. a transporter protein having a preference to transport a hexose compound may be converted to a transporter protein having a preference to transport a pentose compound). A transporter protein may be characterized as a transporter protein derived from a particular organism. Where a transporter protein is derived from a particular organism, the endogenous sequence of the transporter protein may be maintained and residues corresponding to positions 36-41 of the Candida intermedia GXS1 protein may be replaced with a transporter motif sequence. For example, a C. intermedia gxs1 transporter protein is a gxs1 transporter protein, a homolog thereof, or a functional fragment thereof, found in C. intermedia SEQ ID NO:1. Amino acids 75-81 of S. cerevisiae hxt7 transporter protein may be replace with a transporter motif sequence thereby forming a transporter protein with desired sugar transport characteristics described herein. The transporter protein may be a protein, functional fragment, or homolog thereof, identified by the following NCBI gene ID numbers: 836043, 831564, AJ937350.1, AJ875406.1, 2901237, 2913528, 8998057, 8999011, 50419288, 948529, 4839826, 4852047, 4851844, 4840896, 4840252, 4841106, 4851701, 2907283, 2906708, 2908504, 2909312, 2909701, 4935064, 851943, 856640, 856640, 851946, 856494, 8998297, 2902950, 2902912, 853207, 852149, 855023, 853216, 853236, 850536, 855398, 4836720, 4836632, 4840859, 2913215, 2902914, 2910370, 4838168, 2901237.

A "xylose compound" is xylose or a xylose-containing compound including at least one xylose moiety. Thus as used herein, the term xylose compound represents a single xylose, a chain including one or more xylose moieties, or a xylose moiety covalently or non-covalently bound to another chemical moiety (e.g. another sugar forming a xylose containing polysaccharide or xylose bound to lignin). An "arabinose compound" is arabinose or an arabinose-containing compound including at least one arabinose moiety. Thus as used herein, the term arabinose compound represents a single arabinose, a chain including one or more arabinose moieties, or an arabinose moiety covalently or non-covalently bound to another chemical moiety (e.g. another sugar forming a arabinose containing polysaccharide or arabinose bound to lignin). A "galactose compound" is galactose or a galactose-containing compound including at least one galactose moiety. Thus as used herein, the term galactose compound represents a single galactose, a chain including one or more galactose moieties, or a galactose moiety covalently or non-covalently bound to another chemical moiety (e.g. another sugar forming a galactose containing polysaccharide or bound to lignin).

Polysaccharides herein include hexose-only polysaccharides, pentose-only polysaccharides, and hexose-pentose mixture polysaccharides. The xylose compound, the arabinose compound, or the galactose compound may be derived from or form part of a lignocellulosic biomass (e.g. plant dry matter that may used in as a source for pentose compounds or hexose compounds and for production of biofuels or biochemicals), hemicelluose, or other natural or synthetic sources for xylose, arabinose, or galactose. "Derived from" refers to extraction, removal, purification, or otherwise freeing a xylose compound, arabinose compound, or galactose compound from a source (e.g. lignocellulosic biomass) by either chemical processes (e.g. acid hydrolysis, ammonium explosion, or ionic liquids extraction) or through natural biological processes by organisms capable of using such sources for energy.

A "pentose compound" or "pentose" is a monosaccharide-containing compound having 5 carbon atoms. Pentose compounds include aldopentoses (e.g. pentose compounds having an aldehyde moiety at carbon 1) and ketopentoses (e.g. pentose compounds having a ketone moiety at carbon 2 or carbon 3). Pentose compounds include, for example, D/L-arabinose, D/L-lyxose, D/L-ribose, D/L-xylose, D/L-ribulose, and D/L-xylulose. The term "monosaccharide-containing" refers to a compound that includes at least one monosaccharide.

A "hexose compound" "or "hexose" is a monosaccharide-containing compound having 6 carbon atoms. Hexose compounds include aldohexoses (e.g. hexose compounds having an aldehyde moiety at carbon 1) and ketohexoses (e.g. hexose compounds having a ketone moiety at carbon 2). Hexose compounds include, for example, D/L-allose, D/L-altrose, D/L-glucose, D/L-mannose, D/L-gluose, D/L-idose, D/L-galactose, and D/L-talose.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 Molecular Cloning: A Laboratory Manual, 18.1-18.88). The level of expression of a DNA molecule may also be determined by the activity of the protein.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. A "protein gene product" is a protein expressed from a particular gene.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product or interaction can be produced directly between the added reagents or from an intermediate from one or more of the added reagents which can be produced in the reaction mixture.

The term "contacting" may include allowing two species to react, interact, or physically touch, wherein the two species may be a compound described herein (e.g. xylose compound, arabinose compound, or galactose compound) and a protein or enzyme described herein. Contacting may include allowing the compound described herein to interact with a protein or enzyme that is involved in transporting hexose compounds or pentose compounds into a yeast cell.

Provided herein are recombinant hexose and pentose transporter proteins. In one aspect is a recombinant xylose transporter protein. The recombinant xylose transporter protein includes a transporter motif sequence corresponding to amino acid residue positions 36, 37, 38, 39, 40, and 41 of SEQ ID NO: 1 of *Candida intermedia* GXSJ protein. The transporter motif sequence has the sequence -G-G/F-$X^1$-$X^2$-$X^3$-G- (SEQ ID NO: 29). $X^1$ is D, C, G, H, I, L, or F. $X^2$ is A, D, C, E, G, H, or I. $X^3$ is N, C, Q, F, G, L, M, S, T, or P. In embodiments, the transporter motif sequence is not -G-G-L-I-F-G-(SEQ ID NO: 2) or -G-G-F-I-F-G-.(SEQ ID NO: 3).

$X^1$ may be D, C, G, I, L, or F. $X^1$ may be D, C, G, H, or F. $X^1$ may be D. $X^1$ may be C. $X^1$ may be G. $X^1$ may be I. $X^1$ may be L. $X^1$ may be H. $X^1$ may be F. $X^2$ may be D, C, E, G, H, or I. $X^2$ may be E, G, H, or I. $X^2$ may be H or I. $X^2$ may be H. $X^2$ may be I. $X^3$ may be N, Q, F, M, S, T, or P. $X^3$ may be F, M, S, or T. $X^3$ may be S, T, or M. $X^3$ may be T. $X^3$ may be S. $X^3$ may be M. When $X^1$ is F, $X^2$ may be I and $X^3$ may be M or S.

The transporter motif sequence may be -G-G-F-I-M-G--(SEQ ID NO: 4), -G-F-F-I-M-G--(SEQ ID NO: 5), -G-G-F-I-S-G--(SEQ ID NO: 6), -G-F-F-I-S-G--(SEQ ID NO: 7), -G-G-F-I-T-G--(SEQ ID NO: 8), -G-F-F-I-T-G--(SEQ ID NO: 9), -G-G-F-L-M-G--(SEQ ID NO: 10) -G-F-F-L-M-G--(SEQ ID NO: 11), -G-G-F-L-S-G--(SEQ ID NO: 12), -G-F-F-L-S-G--(SEQ ID NO: 13), -G-G-F-L-T-G--(SEQ ID NO: 14), -G-F-F-L-T-G--(SEQ ID NO: 15), -G-G-F-H-M-G--(SEQ ID NO: 16), -G-F-F-H-M-G--(SEQ ID NO: 17), -G-G-F-H-S-G--(SEQ ID NO: 18), -G-F-F-H-S-G--(SEQ ID NO: 19), -G-G-F-H-T-G--(SEQ ID NO: 20) or -G-F-F-H-T-G--(SEQ ID NO: 21). The transporter motif sequence may be -G-G-F-I-M-G--(SEQ ID NO: 4), -G-F-F-I-M-G--(SEQ ID NO: 5), -G-G-F-I-S-G--(SEQ ID NO: 6), -G-F-F-I-S-G--(SEQ ID NO: 7), -G-G-F-I-T-G--(SEQ ID NO: 8), or -G-F-F-I-T-G--(SEQ ID NO: 9). The transporter motif sequence may be -G-G-F-I-M-G--(SEQ ID NO: 4), -G-F-F-I-M-G-(SEQ ID NO: 5)-, -G-G-F-I-S-G--(SEQ ID NO: 6), or -G-F-F-I-S-G--(SEQ ID NO: 7). The transporter motif sequence may be -G-G-F-I-M-G--(SEQ ID NO: 5), or -G-F-F-I-M-G-(SEQ ID NO: 5) or G-G-F-I-M-G (SEQ ID NO: 4). The transporter motif sequence may be -G-G-F-I-M-G-(SEQ ID NO: 4). The transporter motif sequence may be -G-F-F-I-M-G-(SEQ ID NO: 5). The transporter motif sequence may be -G-G-F-I-S-G-(SEQ ID NO: 6). The transporter motif sequence may be -G-F-F-I-S-G-(SEQ ID NO: 7). The transporter motif sequence may be -G-G-F-I-T-G-(SEQ ID NO: 8). The transporter motif sequence may be -G-F-F-I-T-G-(SEQ ID NO: 9). The transporter motif sequence may be -G-G-F-L-M-G-(SEQ ID NO: 10). The transporter motif sequence may be -G-F-F-L-M-G-(SEQ ID NO: 11). The transporter motif sequence may be -G-G-F-L-S-G-(SEQ ID NO: 12). The transporter motif sequence may be -G-F-F-L-S-G-(SEQ ID NO: 13). The transporter motif sequence may be -G-G-F-L-T-G-(SEQ ID NO: 14). The transporter motif sequence may be -G- F-F-L-T-G-(SEQ ID NO: 15). The transporter motif sequence may be -G-G-F-H-M-G-(SEQ ID NO: 16). The transporter motif sequence may be -G-F-F-H-M-G-(SEQ ID NO: 17). The transporter motif sequence may be -G-G-F-H-S-G-(SEQ ID NO: 18). The transporter motif sequence may be -G-F-F-H-S-G-(SEQ ID NO: 19). The transporter motif sequence may be -G-G-F-H-T-G-(SEQ ID NO: 20). The transporter motif sequence may be -G-F-F-H-T-G-(SEQ ID NO: 21).

The recombinant xylose transporter protein described herein may further include a mutation of an amino acid at the residue position corresponding to 297 of *Candida intermedia* GXSJ protein. The amino acid at the residue position corresponding to 297 of *Candida intermedia* GXSJ protein may be substituted with a Met, Ala, Ser, or Asn residue. The amino acid may be substituted with Met. The amino acid may be substituted with Ala. The amino acid may be substituted with Ser. The amino acid may be substituted with Asn. The recombinant xylose transporter protein may include a -G-G-F-I-M-G- (SEQ ID NO: 4) transporter motif sequence and a Met substitution at the position corresponding to 297 of *Candida intermedia* GXSJ protein. The mutations of the amino acid at the residue position corresponding to 297 of *Candida intermedia* GXSJ protein may prevent transport of hexoses by the recombinant xylose transporter. The mutations of the amino acid at the residue position corresponding to 297 of *Candida intermedia* GXSJ protein, in combination with the transporter motif sequences described herein, may prevent transport of hexoses by the recombinant xylose transporter.

The recombinant xylose transporter protein may be derived from a sugar transporter protein (e.g. a transporter protein (e.g. a MFS transporter protein), a homolog thereof, or a functional fragment thereof, found in a cell). The xylose transporter protein may be derived from a yeast cell transporter protein (e.g. a transporter protein, a homolog thereof, or a functional fragment thereof, found in a yeast cell). The yeast cell transporter protein may be a MFS transporter protein. The recombinant xylose transporter protein may be derived from a *C. intermedia* gxs1 transporter protein (e.g. a gxs 1 transporter protein, a homolog thereof, or a functional fragment thereof, found in *C. intermedia* SEQ ID NO:1), a *S. stipitis* rgt2 transporter protein (e.g. a rgt2 transporter protein, a homolog thereof, or a functional fragment thereof, found in *S. stipitis*), or a *S. cerevisiae* hxt7 transporter protein (e.g. a hxt7 transporter protein, a homolog thereof, or a functional fragment thereof, found in *S. cerevisiae*). The recombinant xylose transporter protein may be derived from a *C. intermedia* gxs1 transporter protein. The recombinant xylose transporter protein may be derived from a *S. stipitis* rgt2 transporter protein. The recombinant xylose transporter protein may be derived from a *S. cerevisiae* hxt7 transporter protein.

In another aspect is a recombinant galactose-arabinose transporter protein. The recombinant galactose-arabinose transporter protein includes a transporter motif sequence corresponding to residue positions 36, 37, 38, 39, 40, and 41 of SEQ ID NO: 1 of *Candida intermedia* GXSJ protein. The transporter motif sequence has the sequence -G-G/F-$X^4$-$X^5$-$X^6$-G-(SEQ ID NO: 31). $X^4$ is D, C, F, G, H, L, R, T, or P. $X^5$ is A, C, E, F, H, K, S, P, or V. $X^6$ is R, D, E, F, H, I, M, T, or Y. The sequence is not -G-G-L-V-Y-G-(SEQ ID NO: 22), or -G-G-F-V-F-G (SEQ ID NO: 23).

$X^4$ may be D, F, G, L, R, or T. $X^4$ may be R, T, H, or F. $X^4$ may be R. $X^4$ may be T. $X^4$ may be H. $X^4$ may be F. $X^5$ may be A, E, F, P, H, or V. $X^5$ may be P, H, or V. $X^5$ may be P. $X^5$ may be H. $X^5$ may be V. $X^6$ may be T, H, F, M, or Y. $X^6$ may be F or Y. $X^6$ may be T or M. $X^6$ may be T. $X^6$ may be H. $X^6$ may be F. $X^6$ may be M. $X^6$ may be Y. When $X^4$ is F or T, $X^5$ may be P or I, and $X^6$ may be M or T.

The transporter motif sequence may be -G-G-F-H-M-G-SEQ ID NO: 16), -G-F-F-H-M-G-SEQ ID NO: 17), -G-G-R-P-T-G (SEQ ID NO: 24), -G-F-R-P-T-G-(SEQ ID NO: 25), -G-G-T-P-T-G-(SEQ ID NO: 26), or -G-F-T-P-T-G-(SEQ ID NO: 27). The transporter motif sequence may be -G-G-F-H-M-G-(SEQ ID NO: 16), -G-F-F-H-M-G-(SEQ ID NO: 17). The transporter motif sequence may be -G-G-R-P-T-G-(SEQ ID NO: 24), -G-F-R-P-T-G-(SEQ ID NO: 25). The transporter motif sequence may be -G-G-T-P-T-G-(SEQ ID NO: 26), or -G-F-T-P-T-G-(SEQ ID NO: 27). The transporter motif sequence may be -G-G-F-H-M-G-(SEQ ID NO: 16). The transporter motif sequence may be -G-F-F-H-M-G-(SEQ ID NO: 17). The transporter motif sequence may be -G-G-R-P-T-G-(SEQ ID NO: 24). The transporter motif sequence may be -G-F-R-P-T-G-(SEQ ID NO: 24). The transporter motif sequence may be -G-G-T-P-T-G-(SEQ ID NO: 29). The transporter motif sequence may be -G-F-T-P-T-G-.(SEQ ID NO: 27).

The recombinant galactose-arabinose transporter protein described herein may include a mutation of an amino acid at the residue position corresponding to 297 of SEQ ID NO: 1 of *Candida intermedia* GXSJ protein. The amino acid at the residue position corresponding to 297 of SEQ ID NO: 1 of *Candida intermedia* GXSJ protein may be substituted with a Met, Thr, Ala, or Ile residue. The amino acid may be substituted with Met. The amino acid may be substituted with Thr. The amino acid may be substituted with Ala. The amino acid may be substituted with Ile. The recombinant galactose- arabinose transporter protein may include a -G-G-T-P-T-G-(SEQ ID NO: 28) transporter motif sequence and a Met substitution at the position corresponding to 297 of *Candida intermedia* GXSJ protein. The mutations of the amino acid at the residue position corresponding to 297 of SEQ ID NO: 1 of *Candida intermedia* GXSJ protein may prevent transport of hexoses, other than galactose, by the recombinant galactose-arabinose transporter. The mutations of the amino acid at the residue position corresponding to 297 of SEQ ID NO: 1 of *Candida intermedia* GXSJ protein, in combination with the transporter motif sequences described herein, may prevent transport of hexoses, other than galactose, by the recombinant galactose-arabinose transporter.

The recombinant galactose-arabinose transporter protein may be derived from a sugar transporter protein (e.g. a transporter protein (e.g. a MFS transporter protein), a homolog thereof, or a functional fragment thereof, found in a cell). The recombinant galactose-arabinose transporter protein may be derived from a yeast cell transporter protein (e.g. a transporter protein, a homolog thereof, or a functional fragment thereof, found in a yeast cell). The transporter protein may be a MFS transporter protein. The recombinant galactose-arabinose transporter protein may be derived from a *C. intermedia* gxs1 transporter protein (e.g. a gxs1 transporter protein, a homolog thereof, or a functional fragment thereof, found in *C. intermedia* SEQ ID NO:1), a *S. stipitis* rgt2 transporter protein (e.g. a rgt2 transporter protein, a homolog thereof, or a functional fragment thereof, found in *S. stipitis*), a *S. cerevisiae* hxt7 transporter protein (e.g. a hxt7 transporter protein, a homolog thereof, or a functional fragment thereof, found in *S. cerevisiae*), or a *S. cerevisiae* GAL2 transporter protein (e.g. a GAL2 transporter protein, a homolog thereof, or a functional fragment thereof, found in *S. cerevisiae*). The recombinant galactose-arabinose transporter protein may be derived from a *C. intermedia* gxs1 transporter protein. The recombinant galactose-arabinose transporter protein may be derived from a *S. stipitis* rgt2 transporter protein. The recombinant galactose-arabinose transporter protein may be derived from a *S. cerevisiae* hxt7 transporter protein. The recombinant galactose-arabinose transporter protein may be derived from a *S. cerevisiae* GAL2 transporter protein.

Further provided herein are nucleic acid sequences encoding the hexose or pentose transporter proteins described herein. In one aspect is a nucleic acid encoding a recombinant xylose transporter protein described herein. In another aspect is a nucleic acid encoding a recombinant galactose-arabinose transporter protein described herein. The nucleic acids may be RNA or DNA. The nucleic acids may be single- or double-stranded RNA or single- or double-stranded DNA. The nucleic acids may be located on a plasmid or other vector (e.g. a yeast artificial chromosome (YAC)). The nucleic acids may be introduced and expressed by a yeast cell using conventional techniques known to those in the art.

Provided herein are yeast cells that include a hexose or pentose transporter protein described herein. In one aspect is a yeast cell that includes a recombinant xylose transporter protein described herein. The yeast cell including a recombinant xylose transporter protein described herein may be a *S. stipitis* yeast cell, a *C. intermedia* yeast cell, a *S. cerevisiae* yeast cell, a *D. hansenii* yeast cell, or a *Y. lipolytica* yeast cell. The yeast cell including a recombinant xylose transporter protein described herein may be capable of growth when placed in the presence of pentoses. The yeast cell including a recombinant xylose transporter protein described herein may be capable of growth, or have significantly increased growth compared to a yeast cell lacking the recombinant xylose transporter protein when placed in the presence of a xylose compound. The xylose compound is described herein. The xylose compound may be derived from lignocellulosic biomass.

The xylose compound may be present at a concentration of about 0.05 g/L to about 20 g/L. The xylose compound may be present at a concentration of about 0.05 g/L to about 15 g/L. The xylose compound may be present at a concentration of about 0.05 g/L to about 10 g/L. The xylose compound may be present at a concentration of about 0.05 g/L to about 5 g/L. The xylose compound may be present at a concentration of about 0.05 g/L to about 4 g/L. The xylose compound may be present at a concentration of about 0.05 g/L to about 3 g/L. The xylose compound may be present at a concentration of about 0.05 g/L to about 2 g/L. The xylose compound may be present at a concentration of about 0.05 g/L to about 1 g/L. The xylose compound may be present at a concentration of about 0.05 g/L to about 0.5 g/L. The xylose compound may be present at a concentration of about 0.05 g/L to about 0.1 g/L. The xylose compound may be present at a concentration of about 0.05 g/L. The xylose compound may be present at a concentration of about 0.1 g/L. The xylose compound may be present at a concentration of about 0.5 g/L. The xylose compound may be present at a concentration of about 0.1 g/L. The xylose compound may be present at a concentration of about 0.5 g/L. The xylose compound may be present at a concentration of about 1 g/L. The xylose compound may be present at a concentration of about 2 g/L. The xylose compound may be present at a concentration of about 3 g/L. The xylose compound may be present at a concentration of about 4 g/L. The xylose compound may be present at a concentration of about 5 g/L. The xylose compound may be present at a concentration of about 10 g/L. The xylose compound may be present at a concentration of about 15 g/L. The xylose compound may be present at a concentration of about 20 g/L.

The xylose compound may be present at a concentration of about 0.05 g/L to about 300 g/L. The xylose compound may be present at a concentration of about 0.05 g/L to about 250 g/L. The xylose compound may be present at a concentration of about 0.05 g/L to about 200 g/L. The xylose compound may be present at a concentration of about 0.05 g/L to about 150 g/L. The xylose compound may be present at a concentration of about 0.05 g/L to about 100 g/L. The xylose compound may be present at a concentration of about 0.05 g/L to about 50 g/L. The xylose compound may be present at a concentration of about 0.05 g/L to about 25 g/L. The xylose compound may be present at a concentration of about 1 g/L to about 300 g/L. The xylose compound may be present at a concentration of about 10 g/L to about 300 g/L. The xylose compound may be present at a concentration of about 20 g/L to about 300 g/L. The xylose compound may be present at a concentration of about 30 g/L to about 300 g/L. The xylose compound may be present at a concentration of about 40 g/L to about 300 g/L. The xylose compound may be present at a concentration of about 50 g/L to about 300 g/L. The xylose compound may be present at a concentration of about 75 g/L to about 300 g/L. The xylose compound may be present at a concentration of about 100 g/L to about 300 g/L. The xylose compound may be present at a concentration of about 125 g/L to about 300 g/L. The xylose compound may be present at a concentration of about 150 g/L to about 300 g/L. The xylose compound may be present at a concentration of about 175 g/L to about 300 g/L. The xylose compound may be present at a concentration of about 200 g/L to about 300 g/L. The xylose compound may be present at a concentration of about 225 g/L to about 300 g/L. The xylose compound may be present at a concentration of about 250 g/L to about 300 g/L. The xylose compound may be present at a concentration of about 275 g/L to about 300 g/L.

The xylose compound may be present at a concentration of about 10 g/L to about 275 g/L. The xylose compound may be present at a concentration of about 10 g/L to about 250 g/L. The xylose compound may be present at a concentration of about 10 g/L to about 225 g/L. The xylose compound may be present at a concentration of about 10 g/L to about 200 g/L. The xylose compound may be present at a concentration of about 10 g/L to about 175 g/L. The xylose compound may be present at a concentration of about 10 g/L to about 150 g/L. The xylose compound may be present at a concentration of about 10 g/L to about 125 g/L. The xylose compound may be present at a concentration of about 10 g/L to about 100 g/L. The xylose compound may be present at a concentration of about 10 g/L to about 75 g/L. The xylose compound may be present at a concentration of about 10 g/L to about 50 g/L. The xylose compound may be present at a concentration of about 10 g/L to about 25 g/L.

The xylose compound may be present at a concentration of about 25 g/L. The xylose compound may be present at a concentration of about 50 g/L. The xylose compound may be present at a concentration of about 75 g/L. The xylose compound may be present at a concentration of about 100 g/L. The xylose compound may be present at a concentration of about 125 g/L. The xylose compound may be present at a concentration of about 150 g/L. The xylose compound may be present at a concentration of about 175 g/L. The xylose compound may be present at a concentration of about 200 g/L. The xylose compound may be present at a concentration of about 225 g/L. The xylose compound may be present at a concentration of about 250 g/L. The xylose compound may be present at a concentration of about 275 g/L. The xylose compound may be present at a concentration of about 300 g/L.

The yeast cell including a recombinant xylose transporter protein described herein may be incapable of growth, or have significantly impaired growth compared to a yeast cell lacking the recombinant xylose transporter protein when placed in the presence of only hexoses. The hexose (e.g. glucose) may be present at a concentration of about 0.05 g/L to about 20 g/L. The hexose (e.g. glucose) may be present at a concentration of about 0.05 g/L to about 15 g/L. The hexose (e.g. glucose) may be present at a concentration of about 0.05 g/L to about 10 g/L. The hexose (e.g. glucose) may be present at a concentration of about 0.05 g/L to about 5 g/L. The hexose (e.g. glucose) may be present at a concentration of about 0.05 g/L to about 4 g/L. The hexose (e.g. glucose) may be present at a concentration of about 0.05 g/L to about 3 g/L. The hexose (e.g. glucose) may be present at a concentration of about 0.05 g/L to about 2 g/L. The hexose (e.g. glucose) may be present at a concentration of about 0.05 g/L to about 1 g/L. The hexose (e.g. glucose) may be present at a concentration of about 0.05 g/L to about 0.5 g/L. The hexose (e.g. glucose) may be present at a concentration of about 0.05 g/L to about 0.1 g/L. The hexose (e.g. glucose) may be present at a concentration of about 0.05 g/L. The hexose (e.g. glucose) may be present at a concentration of about 0.1 g/L. The hexose (e.g. glucose) may be present at a concentration of about 0.5 g/L. The hexose (e.g. glucose) may be present at a concentration of about 0.1 g/L. The hexose (e.g. glucose) may be present at a concentration of about 0.5 g/L. The hexose (e.g. glucose) may be present at a concentration of about 1 g/L. The hexose (e.g. glucose) may be present at a concentration of about 2 g/L. The hexose (e.g. glucose) may be present at a concentration of about 3 g/L. The hexose (e.g. glucose) may be present at a concentration of about 4 g/L. The hexose (e.g. glucose) may be present at a concentration of about 5 g/L. The hexose (e.g. glucose) may be present at a concentration of about 10 g/L. The hexose (e.g. glucose) may be present at a concentration of about 15 g/L. The hexose (e.g. glucose) may be present at a concentration of about 20 g/L.

The recombinant xylose transporter protein of the yeast cell may include a transporter motif sequence as set forth herein. The yeast cell may metabolize the xylose compound. The yeast cell may convert xylose compound to a biofuel (e.g. ethanol) or a biochemical described herein. The yeast cell may convert xylose compound to a biofuel (e.g. ethanol). The yeast cell may convert xylose compound to a biochemical described herein.

In another aspect is a yeast cell that includes a recombinant galactose-arabinose transporter protein described herein. The yeast cell including a recombinant galactose-arabinose transporter protein described herein may be a *S. stipitis* yeast cell, a *C. intermedia* yeast cell, a *S. cerevisiae* yeast cell, a *D. hansenii* yeast cell, or a *Y. lipolytica* yeast cell. The yeast cell including the recombinant galactose-arabinose transporter protein may be capable of growth, or have significantly increased growth compared to a yeast cell lacking the recombinant galactose-arabinose transporter protein when placed in the presence of pentoses (e.g. arabinose). The yeast cell including the recombinant galactose-arabinose transporter protein may be capable of growth, or have significantly increased growth compared to a yeast cell lacking the recombinant galactose-arabinose transporter protein when placed in the presence of an arabinose compound. The arabinose compound is described herein. The arabinose compound may be derived from lignocellulosic biomass.

The arabinose compound may be present at a concentration of about 0.05 g/L to about 20 g/L. The arabinose compound may be present at a concentration of about 0.05 g/L to about 15 g/L. The arabinose compound may be present at a concentration of about 0.05 g/L to about 10 g/L. The arabinose compound may be present at a concentration of about 0.05 g/L to about 5 g/L.

The arabinose compound may be present at a concentration of about 0.05 g/L to about 4 g/L. The arabinose compound may be present at a concentration of about 0.05 g/L to about 3 g/L. The arabinose compound may be present at a concentration of about 0.05 g/L to about 2 g/L. The arabinose compound may be present at a concentration of about 0.05 g/L to about 1 g/L. The arabinose compound may be present at a concentration of about 0.05 g/L to about 0.5 g/L. The arabinose compound may be present at a concentration of about 0.05 g/L to about 0.1 g/L. The arabinose compound may be present at a concentration of about 0.05 g/L. The arabinose compound may be present at a concentration of about 0.1 g/L. The arabinose compound may be present at a concentration of about 0.5 g/L. The arabinose compound may be present at a concentration of about 0.1 g/L. The arabinose compound may be present at a concentration of about 0.5 g/L. The arabinose compound may be present at a concentration of about 1 g/L. The arabinose compound may be present at a concentration of about 2 g/L. The arabinose compound may be present at a concentration of about 3 g/L. The arabinose compound may be present at a concentration of about 4 g/L. The arabinose compound may be present at a concentration of about 5 g/L. The arabinose compound may be present at a concentration of about 10 g/L. The arabinose compound may be present at a concentration of about 15 g/L. The arabinose compound may be present at a concentration of about 20 g/L.

The arabinose compound may be present at a concentration of about 0.05 g/L to about 300 g/L. The arabinose compound may be present at a concentration of about 0.05 g/L to about 250 g/L. The arabinose compound may be present at a concentration of about 0.05 g/L to about 200 g/L. The arabinose compound may be present at a concentration of about 0.05 g/L to about 150 g/L. The arabinose compound may be present at a concentration of about 0.05 g/L to about 100 g/L. The arabinose compound may be present at a concentration of about 0.05 g/L to about 50 g/L. The arabinose compound may be present at a concentration of about 0.05 g/L to about 25 g/L. The arabinose compound may be present at a concentration of about 1 g/L to about 300 g/L. The arabinose compound may be present at a concentration of about 10 g/L to about 300 g/L. The arabinose compound may be present at a concentration of about 20 g/L to about 300 g/L. The arabinose compound may be present at a concentration of about 30 g/L to about 300 g/L. The arabinose compound may be present at a concentration of about 40 g/L to about 300 g/L. The arabinose compound may be present at a concentration of about 50 g/L to about 300 g/L. The arabinose compound may be present at a concentration of about 75 g/L to about 300 g/L. The arabinose compound may be present at a concentration of about 100 g/L to about 300 g/L.

The arabinose compound may be present at a concentration of about 125 g/L to about 300 g/L. The arabinose compound may be present at a concentration of about 150 g/L to about 300 g/L. The arabinose compound may be present at a concentration of about 175 g/L to about 300 g/L. The arabinose compound may be present at a concentration of about 200 g/L to about 300 g/L. The arabinose compound may be present at a concentration of about 225 g/L to about 300 g/L. The arabinose compound may be present at a concentration of about 250 g/L to about 300 g/L. The arabinose compound may be present at a concentration of about 275 g/L to about 300 g/L.

The arabinose compound may be present at a concentration of about 10 g/L to about 275 g/L. The arabinose compound may be present at a concentration of about 10 g/L to about 250 g/L. The arabinose compound may be present at a concentration of about 10 g/L to about 225 g/L. The arabinose compound may be present at a concentration of about 10 g/L to about 200 g/L. The arabinose compound may be present at a concentration of about 10 g/L to about 175 g/L. The arabinose compound may be present at a concentration of about 10 g/L to about 150 g/L. The arabinose compound may be present at a concentration of about 10 g/L to about 125 g/L. The arabinose compound may be present at a concentration of about 10 g/L to about 100 g/L. The arabinose compound may be present at a concentration of about 10 g/L to about 75 g/L. The arabinose compound may be present at a concentration of about 10 g/L to about 50 g/L. The arabinose compound may be present at a concentration of about 10 g/L to about 25 g/L.

The arabinose compound may be present at a concentration of about 25 g/L. The arabinose compound may be present at a concentration of about 50 g/L. The arabinose compound may be present at a concentration of about 75 g/L. The arabinose compound may be present at a concentration of about 100 g/L. The arabinose compound may be present at a concentration of about 125 g/L. The arabinose compound may be present at a concentration of about 150 g/L. The arabinose compound may be present at a concentration of about 175 g/L. The arabinose compound may be present at a concentration of about 200 g/L. The arabinose compound may be present at a concentration of about 225 g/L. The arabinose compound may be present at a concentration of about 250 g/L. The arabinose compound may be present at a concentration of about 275 g/L. The arabinose compound may be present at a concentration of about 300 g/L.

The yeast cell including the recombinant galactose-arabinose transporter protein may be incapable of growth, or have significantly impaired growth compared to a yeast cell lacking the recombinant galactose-arabinose transporter protein when placed in the presence of hexoses such as glucose or mannose (i.e. the recombinant galactose-arabinose transporter protein does not transport glucose or mannose). The hexose (e.g. glucose) may in present in a concentration as set forth herein. The yeast cell including the recombinant galactose-arabinose transporter protein may be capable of growth, or have significantly increased growth compared to a yeast cell lacking the recombinant galactose-arabinose transporter protein when placed in the presence of a galactose compound. The galactose compound is described herein. The galactose compound may be derived from lignocellulosic biomass.

The galactose compound may be present at a concentration of about 0.05 g/L to about 20 g/L. The galactose compound may be present at a concentration of about 0.05 g/L to about 15 g/L. The galactose compound may be present at a concentration of about 0.05 g/L to about 10 g/L. The galactose compound may be present at a concentration of about 0.05 g/L to about 5 g/L. The galactose compound may be present at a concentration of about 0.05 g/L to about 4 g/L. The galactose compound may be present at a concentration of about 0.05 g/L to about 3 g/L. The galactose compound may be present at a concentration of about 0.05 g/L to about 2 g/L. The galactose compound may be present at a concentration of about 0.05 g/L to about 1 g/L. The galactose compound may be present at a concentration of about 0.05 g/L to about 0.5 g/L. The galactose compound may be present at a concentration of about 0.05 g/L to about 0.1 g/L. The galactose compound may be present at a concentration of about 0.05 g/L. The galactose compound may be present at a concentration of about 0.1 g/L. The galactose compound may be present at a concentration of about 0.5 g/L. The galactose compound may be present at a concentration of about 0.1 g/L. The galactose compound may be present at a concentration of about 0.5 g/L. The galactose compound may be present at a concentration of about 1 g/L. The galactose compound may be present at a concentration of about 2 g/L. The galactose compound may be present at a concentration of about 3 g/L. The galactose compound may be present at a concentration of about 4 g/L. The galactose compound may be present at a concentration of about 5 g/L. The galactose compound may be present at a concentration of about 10 g/L. The galactose compound may be present at a concentration of about 15 g/L. The galactose compound may be present at a concentration of about 20 g/L.

The galactose compound may be present at a concentration of about 0.05 g/L to about 300 g/L. The galactose compound may be present at a concentration of about 0.05 g/L to about 250 g/L. The galactose compound may be present at a concentration of about 0.05 g/L to about 200 g/L. The galactose compound may be present at a concentration of about 0.05 g/L to about 150 g/L. The galactose compound may be present at a concentration of about 0.05 g/L to about 100 g/L. The galactose compound may be present at a concentration of about 0.05 g/L to about 50 g/L. The galactose compound may be present at a concentration of about 0.05 g/L to about 25 g/L. The galactose compound may be present at a concentration of about 1 g/L to about 300 g/L. The galactose compound may be present at a concentration of about 10 g/L to about 300 g/L. The galactose compound may be present at a concentration of about 20 g/L to about 300 g/L. The galactose compound may be present at a concentration of about 30 g/L to about 300 g/L. The galactose compound may be present at a concentration of about 40 g/L to about 300 g/L. The galactose compound may be present at a concentration of about 50 g/L to about 300 g/L. The galactose compound may be present at a concentration of about 75 g/L to about 300 g/L. The galactose compound may be present at a concentration of about 100 g/L to about 300 g/L. The galactose compound may be present at a concentration of about 125 g/L to about 300 g/L. The galactose compound may be present at a concentration of about 150 g/L to about 300 g/L. The galactose compound may be present at a concentration of about 175 g/L to about 300 g/L. The galactose compound may be present at a concentration of about 200 g/L to about 300 g/L. The galactose compound may be present at a concentration of about 225 g/L to about 300 g/L. The galactose compound may be present at a concentration of about 250 g/L to about 300 g/L. The galactose compound may be present at a concentration of about 275 g/L to about 300 g/L.

The galactose compound may be present at a concentration of about 10 g/L to about 275 g/L. The galactose compound may be present at a concentration of about 10 g/L to about 250 g/L. The galactose compound may be present at a concentration of about 10 g/L to about 225 g/L. The galactose compound may be present at a concentration of about 10 g/L to about 200 g/L. The galactose compound may be present at a concentration of about 10 g/L to about 175 g/L. The galactose compound may be present at a concentration of about 10 g/L to about 150 g/L. The galactose compound may be present at a concentration of about 10 g/L to about 125 g/L. The galactose compound may be present at a concentration of about 10 g/L to about 100 g/L. The galactose compound may be present at a concentration of about 10 g/L to about 75 g/L. The galactose compound may be present at a concentration of about 10 g/L to about 50 g/L. The galactose compound may be present at a concentration of about 10 g/L to about 25 g/L.

The galactose compound may be present at a concentration of about 25 g/L. The galactose compound may be present at a concentration of about 50 g/L. The galactose compound may be present at a concentration of about 75 g/L. The galactose compound may be present at a concentration of about 100 g/L. The galactose compound may be present at a concentration of about 125 g/L. The galactose compound may be present at a concentration of about 150 g/L. The galactose compound may be present at a concentration of about 175 g/L. The galactose compound may be present at a concentration of about 200 g/L. The galactose compound may be present at a concentration of about 225 g/L. The galactose compound may be present at a concentration of about 250 g/L. The galactose compound may be present at a concentration of about 275 g/L. The galactose compound may be present at a concentration of about 300 g/L.

The yeast cell including the recombinant galactose-arabinose transporter protein may be capable of growth, or have significantly increased growth when compared to a yeast cell lacking the recombinant galactose-arabinose transporter protein when placed in the presence of an arabinose compound and a galactose compound. The arabinose compound is described herein and may be present in a concentration described herein. The galactose compound is described herein and may be present in a concentration described herein. The arabinose compound may be derived from lignocellulosic biomass. The galactose compound may be derived from lignocellulosic biomass.

The recombinant galactose-arabinose transporter protein of the yeast cell may include a transporter motif sequence as set forth herein. The yeast cell may metabolize the arabinose compound. The yeast cell may metabolize the galactose compound. The yeast cell may convert the arabinose compound to a biofuel (e.g. ethanol) or a biochemical described herein. The yeast cell may convert the galactose compound to a biofuel (e.g. ethanol) or a biochemical described herein. The yeast cell may convert the arabinose compound to a biofuel (e.g. ethanol). The yeast cell may convert the arabinose compound to a biochemical described herein. The yeast cell may convert the galactose compound to a biofuel (e.g. ethanol). The yeast cell may convert the galactose compound to a biochemical described herein.

Also provided herein are methods of transporting hexose or pentose moieties into a yeast cell. In one aspect is a method for transporting xylose into a yeast cell. The method includes contacting a yeast cell having a recombinant xylose transport protein described herein with a xylose compound described herein. The recombinant xylose transport protein is allowed to transport the xylose compound into the cell. The yeast cell may be a yeast cell described herein. The yeast cell may be a *S. stipitis* yeast cell, a *C. intermedia* yeast cell, a *S. cerevisiae* yeast cell, a *D. hansenii* yeast cell, or a *Y. lipolytica* yeast cell.

The xylose compound may be derived from lignocellulosic biomass, hemicellulose, or xylan. The xylose compound may be derived from lignocellulosic biomass. The xylose compound may be derived from hemicellulose. The xylose compound may be derived from xylan. The yeast cell may metabolize the xylose compound. The yeast cell may preferentially grow in the presence of a xylose compound and may not grow using only another sugar source (e.g. glucose) when compared to a yeast cell lacking the recombinant xylose transporter protein. The xylose compound may be present in a concentration described herein. The yeast cell may convert the xylose compound to a biofuel (e.g. ethanol) or to a biochemical described herein. The yeast cell may convert the xylose compound to a biofuel (e.g. ethanol). The yeast cell may convert the xylose compound to a biochemical described herein.

The recombinant xylose transport protein may have a binding affinity of about 1 mM to about 0.02 mM for a xylose compound. The recombinant xylose transport protein may have a binding affinity of about 0.8 mM to about 0.02 mM for a xylose compound. The recombinant xylose transport protein may have a binding affinity of 0.8 mM to about 0.05 mM for a xylose compound. The recombinant xylose transport protein may have a binding affinity of 0.8 mM to about 0.1 mM for a xylose compound. The recombinant xylose transport protein may have a binding affinity of 0.8 mM to about 0.2 mM for a xylose compound. The recombinant xylose transport protein may have a binding affinity of 0.8 mM to about 0.3 mM for a xylose compound. The recombinant xylose transport protein may have a binding affinity of 0.8 mM to about 0.4 mM for a xylose compound. The recombinant xylose transport protein may have a binding affinity of 0.8 mM to about 0.5 mM for a xylose compound. The recombinant xylose transport protein may have a binding affinity of 0.8 mM to about 0.6 mM for a xylose compound. The recombinant xylose transport protein may have a binding affinity of 0.8 mM to about 0.7 mM for a xylose compound.

The recombinant xylose transport protein may have a binding affinity of at least 0.02 mM for a xylose compound. The recombinant xylose transport protein may have a binding affinity of at least 0.05 mM for a xylose compound. The recombinant xylose transport protein may have a binding affinity of at least 0.1 mM for a xylose compound. The recombinant xylose transport protein may have a binding affinity of at least 0.2 mM for a xylose compound. The recombinant xylose transport protein may have a binding affinity of at least 0.3 mM for a xylose compound. The recombinant xylose transport protein may have a binding affinity of at least 0.4 mM for a xylose compound. The recombinant xylose transport protein may have a binding affinity of at least 0.5 mM for a xylose compound. The recombinant xylose transport protein may have a binding affinity of at least 0.6 mM for a xylose compound. The recombinant xylose transport protein may have a binding affinity of at least 0.7 mM for a xylose compound. The recombinant xylose transport protein may have a binding affinity of at least 0.8 mM for a xylose compound. The recombinant xylose transport protein may have a binding affinity of at least 0.9 mM for a xylose compound. The recombinant xylose transport protein may have a binding affinity of at least 1 mM for a xylose compound.

The recombinant xylose transport protein may have a rate of transporting a xylose compound into a yeast cell of about 7 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 8 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 9 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 11 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 12 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 13 nmol min$^{-1}$ gDCW$^{-1}$ to about 15 nmol min$^{-1}$ gDCW$^{-1}$. The recombinant xylose transport protein may have a rate of transporting a xylose compound into a yeast cell of about 14 nmol min gDCW$^{-1}$ to about 15 nmol min$^{-1}$ gDCW$^{-1}$.

The recombinant xylose transport protein may have a rate of at least 7 nmol min$^{-1}$ gDCW$^{-1}$ of transporting a xylose compound into a yeast cell. The recombinant xylose transport protein may have a rate of at least 8 nmol min$^{-1}$ gDCW$^{-1}$ of transporting a xylose compound into a yeast cell. The recombinant xylose transport protein may have a rate of at least 9 nmol min$^{-1}$ gDCW$^{-1}$ of transporting a xylose compound into a yeast cell. The recombinant xylose transport protein may have a rate of at least 10 nmol min$^{-1}$ gDCW$^{-1}$ of transporting a xylose compound into a yeast cell. The recombinant xylose transport protein may have a rate of at least 11 nmol min$^{-1}$ gDCW$^{-1}$ of transporting a xylose compound into a yeast cell. The recombinant xylose transport protein may have a rate of at least 12 nmol min$^{-1}$ gDCW$^{-1}$ of transporting a xylose compound into a yeast cell. The recombinant xylose transport protein may have a rate of at least 13 nmol min$^{-1}$ gDCW$^{-1}$ of transporting a xylose compound into a yeast cell. The recombinant xylose transport protein may have a rate of at least 14 nmol min$^{-1}$ gDCW$^{-1}$ of transporting a xylose compound into a yeast cell. The recombinant xylose transport protein may have a rate of at least 15 nmol min$^{-1}$ gDCW$^{-1}$ of transporting a xylose compound into a yeast cell.

The recombinant xylose transport protein may have a rate of transporting a xylose compound into a yeast cell of about 10 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 20 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 30 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 40 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 50 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 60 nmol min$^{-1}$ gDCW$^{-1}$ to about 70 nmol min$^{-1}$ gDCW$^{-1}$. The recombinant xylose transport protein may have a rate of transporting a xylose compound into a yeast cell of about 80 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 90 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 100 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 110 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 120 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 130 nmol min$^{-1}$ gDCW$^{-1}$ to about 150 nmol min$^{-1}$ gDCW$^{-1}$. The recombinant xylose transport protein may have a rate of transporting a xylose compound into a yeast cell of about 140 nmol min$^{-1}$ gDCW$^{-1}$ to about 150 nmol min$^{-1}$ gDCW$^{-1}$.

The recombinant xylose transport protein may have a rate of transporting a xylose compound into a yeast cell of about 10 nmol min$^{-1}$ gDCW$^{-1}$ to about 140 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 130 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 120 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 110 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 100 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 90 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 80 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 70 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 60 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 50 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 40 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 30 nmol min$^{-1}$ gDCW$^{-1}$. The recombinant xylose transport protein may have a rate of transporting a xylose compound into a yeast cell of about 10 nmol min$^{-1}$ gDCW$^{-1}$ to about 20 nmol min$^{-1}$ gDCW$^{-1}$.

The recombinant xylose transport protein may have a rate of at least 20 nmol min$^{-1}$ gDCW$^{-1}$ of transporting a xylose compound into a yeast cell. The recombinant xylose transport protein may have a rate of at least 30 nmol min$^{-1}$ gDCW$^{-1}$ of transporting a xylose compound into a yeast cell. The recombinant xylose transport protein may have a rate of at least 40 nmol min$^{-1}$ gDCW$^{-1}$ of transporting a xylose compound into a yeast cell. The recombinant xylose transport protein may have a rate of at least 50 nmol min$^{-1}$ gDCW$^{-1}$ of transporting a xylose compound into a yeast cell. The recombinant xylose transport protein may have a rate of at least 60 nmol min$^{-1}$ gDCW$^{-1}$ of transporting a xylose compound into a yeast cell. The recombinant xylose transport protein may have a rate of at least 70 nmol min$^{-1}$ gDCW$^{-1}$ of transporting a xylose compound into a yeast cell. The recombinant xylose transport protein may have a rate of at least 80 nmol min$^{-1}$ gDCW$^{-1}$ of transporting a xylose compound into a yeast cell. The recombinant xylose transport protein may have a rate of at least 90 nmol min$^{-1}$ gDCW$^{-1}$ of transporting a xylose compound into a yeast cell. The recombinant xylose transport protein may have a rate of at least 100 nmol min$^{-1}$ gDCW$^{-1}$ of transporting a xylose compound into a yeast cell. The recombinant xylose transport protein may have a rate of at least 110 nmol min$^{-1}$ gDCW$^{-1}$ of transporting a xylose compound into a yeast cell. The recombinant xylose transport protein may have a rate of at least 120 nmol min$^{-1}$ gDCW$^{-1}$ of transporting a xylose compound into a yeast cell. The recombinant xylose transport protein may have a rate of at least 130 nmol min$^{-1}$ gDCW$^{-1}$ of transporting a xylose compound into a yeast cell. The recombinant xylose transport protein may have a rate of at least 140 nmol min$^{-1}$ gDCW$^{-1}$ of transporting a xylose compound into a yeast cell. The recombinant xylose transport protein may have a rate of at least 150 nmol min$^{-1}$ gDCW$^{-1}$ of transporting a xylose compound into a yeast cell.

In another aspect is a method of transporting galactose or arabinose into a yeast cell. The method includes contacting a yeast cell including a recombinant galactose-arabinose transport protein described herein, with a galactose compound or an arabinose compound described herein. The recombinant galactose-arabinose transport protein is allowed to transport the galactose compound or the arabinose compound into the yeast cell. The yeast cell may be a yeast cell described herein. The yeast cell may be a *S. stipitis* yeast cell, a *C. intermedia* yeast cell, a *S. cerevisiae* yeast cell, a *D. hansenii* yeast cell, or a *Y. lipolytica* yeast cell.

In the presence of arabinose, the recombinant galactose-arabinose transport protein may transport arabinose into a yeast cell. The arabinose compound may be present at a concentration as set forth herein. The arabinose compound may be derived from lignocellulosic biomass, hemicellulose, or arabinoxylan. The arabinose compound may be derived from lignocellulosic biomass. The arabinose compound may be derived from hemicellulose. The arabinose compound may be derived from arabinoxylan. The yeast cell may metabolize the arabinose compound. The yeast cell may preferentially grow in the presence of an arabinose compound and may not grow using only another sugar source (e.g. glucose) as compared to a yeast cell lacking the recombinant galactose-arabinose transporter protein. The yeast cell may convert the arabinose compound to a biofuel (e.g. ethanol) or to a biochemical (e.g. an organic acid.) The yeast cell may convert the arabinose compound to a biofuel (e.g. ethanol). The yeast cell may convert the arabinose compound to a biochemical described herein.

In the presence of galactose, the recombinant galactose-arabinose transport protein transports galactose into a yeast cell. The galactose compound may be at a concentration as set forth herein. The galactose compound may be derived from lignocellulosic biomass, hemicellulose, or galactan. The galactose compound may be derived from lignocellulosic biomass. The galactose compound may be derived from hemicellulose. The galactose compound may be derived from galactan. The yeast cell may metabolize the galactose compound. The yeast cell may preferentially grow in the presence of a galactose compound and may not grow using only another sugar source (e.g. glucose). The yeast cell may convert the galactose compound to a biofuel (e.g. ethanol) or to a biochemical described herein. The yeast cell may convert the galactose compound to a biofuel (e.g. ethanol). The yeast cell may convert the galactose compound to a biochemical described herein.

I. EMBODIMENTS

Embodiment 1

A recombinant xylose transporter protein comprising a transporter motif sequence corresponding to amino acid residue positions 36, 37, 38, 39, 40, and 41 of SEQ ID NO: 1 of *Candida intermedia* GXSJ protein, wherein said transporter motif sequence is -G-G/F-X$^1$-X$^2$-X$^3$-G-(SEQ ID NO: 29); wherein, X$^1$ is D, C, G, H, I, L, or F; X$^2$ is A, D, C, E, G, H, or I; X$^3$ is N, C, Q, F, G, L, M, S, T, or P; and wherein, said transporter motif sequence is not -G-G-L-I-F-G- (SEQ ID NO: 2) or -G-G-F-I-F-G-(SEQ ID NO: 3).

Embodiment 2

The recombinant xylose transporter protein of embodiment 1, wherein, X$^1$ is D, C, G, H, or F; X$^2$ is H or I; and X$^3$ is S, T, or M.

Embodiment 3

The recombinant xylose transporter protein of embodiment 1 or 2, wherein X$^1$ is F, X$^2$ is I, and X$^3$ is M or S.

Embodiment 4

The recombinant xylose transporter protein of any one of embodiments 1 to 3, wherein said transporter motif sequence is -G-G-F-I-M-G-(SEQ ID NO: 4), -G-F-F-I-M-G-(SEQ ID NO: 5), -G-G-F-I-S-G-(SEQ ID NO: 6), -G-F-F-I-S-G-(SEQ ID NO: 7), -G-G-F-I-T-G-(SEQ ID NO: 8), -G-F-F-I-T-G-(SEQ ID NO: 9), -G-G-F-L-M-G-(SEQ ID NO: 10), -G-F-F-L-M-G-(SEQ ID NO: 11), -G-G-F-L-S-G-(SEQ ID NO: 12), -G-F-F-L-S-G-(SEQ ID NO: 13), -G-G-F-L-T-G-(SEQ ID NO: 14), -G-F-F-L-T-G-(SEQ ID NO: 15), -G-G-F-H-M-G-(SEQ ID NO: 16), -G-F-F-H-M-G-(SEQ ID NO: 17), -G-G-F-H-S-G-(SEQ ID NO: 18), -G-F-F-H-S-G-(SEQ ID NO: 19), -G-G-F-H-T-G-(SEQ ID NO: 20) or -G-F-F-H-T-G-(SEQ ID NO: 21).

Embodiment 5

The recombinant xylose transporter protein of any one of embodiments 1 to 4, wherein said transporter motif sequence is -G-G-F-I-M-G- (SEQ ID NO: 4), -G-F-F-I-M-G-(SEQ ID NO: 5), -G-G-F-I-S-G-(SEQ ID NO: 6), or -G-F-F-I-S-G-(SEQ ID NO: 7).

Embodiment 6

The recombinant xylose transporter protein of any one of embodiments 1 to 5 further comprising a mutation of an amino acid at the residue position corresponding to 297 of *Candida intermedia* GXS1 protein.

Embodiment 7

The recombinant xylose transporter protein of any one of embodiments 1 to 6, wherein said amino acid at the residue position corresponding to 297 of *Candida intermedia* GXS1 protein is substituted with a Met, Ala, Ser, or Asn residue.

Embodiment 8

The recombinant xylose transporter protein of any one of embodiments 1 to 7, wherein said recombinant xylose transporter protein is derived from a *C. intermedia* gxs1 transporter protein, a *S. stipitis* rgt2 transporter protein, or a *S. cerevisiae* hxt7 transporter protein.

Embodiment 9

A recombinant galactose-arabinose transporter protein comprising a transporter motif sequence corresponding to amino acid residue positions 36, 37, 38, 39, 40, and 41 of SEQ ID NO: 1 of *Candida intermedia* GXSJ protein, wherein said transporter motif sequence is -G-G/F-X$^4$-X$^5$-X$^6$-G-(SEQ ID NO: 30); wherein, X$^4$ is D, C, F, G, H, L, R, T, or P; X$^5$ is A, C, E, F, H, K, S, P, or V; X$^6$ is R, D, E, F, H, I, M, T, or Y; and wherein said sequence is not -G-G-L-V-Y-G-(SEQ ID NO: 22), or -G-G-F-V-F-G- (SEQ ID NO: 23).

Embodiment 10

The recombinant galactose-arabinose transporter protein of embodiment 9, wherein, X$^4$ is R, T, H, or F; X$^5$ is P, H, or V; and X$^6$ is T, H, F, M, or Y.

Embodiment 11

The recombinant galactose-arabinose transporter protein of embodiment 9, wherein X$^4$ is F or T, X$^5$ is P or I, and X$^6$ is M or T.

Embodiment 12

The recombinant galactose-arabinose transporter protein of embodiment 10 or 11, wherein said transporter motif sequence is -G-G-F-H-M-G-(SEQ ID NO: 16), -G-F-F-H-M-G-(SEQ ID NO: 17), -G-G-R-P-T-G-(SEQ ID NO: 24), -G-F-R-P-T-G-(SEQ ID NO: 25), -G-G-T-P-T-G-(SEQ ID NO: 26), or -G-F-T-P-T-G-(SEQ ID NO: 27).

Embodiment 13

The recombinant galactose-arabinose transporter protein of any one of embodiments 9 to 12, wherein said galactose-arabinose transporter protein further comprises a mutation of an amino acid at the residue position corresponding to 297 of *Candida intermedia* GXS1 protein.

Embodiment 14

The recombinant galactose-arabinose transporter protein of any one of embodiments 9 to 13, wherein said amino acid at the residue position corresponding to 297 of *Candida intermedia* GXS1 protein is substituted with a Met, Thr, Ala, or Ile residue.

Embodiment 15

The recombinant galactose-arabinose transporter protein of any one of embodiments 9 to 14, wherein said recombinant galactose-arabinose transporter protein is derived from a *C. intermedia* gxs1 transporter protein, a *S. stipitis* rgt2 transporter protein, a *S. cerevisiae* hxt7 transporter protein, or a *S. cerevisiae* GAL2 protein.

Embodiment 16

A yeast cell comprising the recombinant xylose transporter protein of any one of embodiments 1 to 8.

Embodiment 17

A yeast cell comprising the recombinant galactose-arabinose transporter protein of any one of embodiments 9 to 15.

Embodiment 18

A nucleic acid encoding the recombinant xylose transporter protein of any one of embodiments 1 to 8.

Embodiment 19

A nucleic acid encoding the recombinant galactose-arabinose transporter protein of any one of embodiments 9 to 15.

Embodiment 20

A method of transporting xylose into a yeast cell, said method comprising: contacting a yeast cell comprising the recombinant xylose transporter protein of any one of embodiments 1 to 8 with a xylose compound; and allowing said recombinant xylose transporter protein to transport said xylose compound into said yeast cell.

Embodiment 21

The method of embodiment 20, wherein said xylose compound forms part of lignocellulosic biomass, hemicellulose, or xylan.

Embodiment 22

The method of embodiment 20 or 21, wherein said yeast cell metabolizes said xylose compound.

Embodiment 23

The method of any one of embodiments 20 to 22, wherein said yeast cell converts said xylose compound to a biofuel.

Embodiment 24

The method of any one of embodiments 20 to 23, wherein said recombinant xylose transporter protein has a binding affinity of at least 0.7 mM for said xylose compound.

Embodiment 25

The method of any one of embodiments 20 to 24, wherein said recombinant xylose transporter protein has a rate of at least 15 nmol min$^{-1}$ gDCW$^{-1}$ of transporting said xylose compound into said yeast cell.

Embodiment 26

A method of transporting galactose or arabinose into a yeast cell, said method comprising: contacting a yeast cell comprising the recombinant galactose-arabinose transporter protein of any one of embodiments 9 to 15 with a galactose compound or an arabinose compound; and allowing said recombinant galactose-arabinose transporter protein to transport said galactose compound or said arabinose compound into said yeast cell.

Embodiment 27

The method of embodiment 26, wherein said recombinant galactose-arabinose transporter protein is contacted with an arabinose compound.

Embodiment 28

The method of any one of embodiments 26 to 27, wherein said arabinose compound forms part of lignocellulosic biomass, hemicellulose or arabinoxylan.

Embodiment 29

The method of any one of embodiments 26 to 28, wherein said yeast cell metabolizes said arabinose compound.

Embodiment 30

The method of any one of embodiments 26 to 29, wherein said yeast cell converts said arabinose compound to a biofuel.

Embodiment 31

The method of any one of embodiments 26 to 30, wherein said recombinant galactose-arabinose transporter protein is contacted with a galactose compound.

Embodiment 32

The method of any one of embodiments 26 to 31, wherein said galactose compound forms a part of lignocellulosic biomass, hemicellulose, or galactan.

Embodiment 33

The method of any one of embodiments 26 to 32, wherein said yeast cell metabolizes said galactose compound.

Embodiment 34

The method of any one of embodiments 26 to 33, wherein said yeast cell converts said galactose compound to a biofuel.

Embodiment 35

The method of embodiment 20, wherein said yeast cell is a *S. stipitis* yeast cell, a *C. intermedia* yeast cell, a *S. cerevisiae* yeast cell, a *D. hansenii* yeast cell, or a *Y. lipolytica* yeast cell.

Embodiment 36

The method of embodiment 26, wherein said yeast cell is a *S. stipitis* yeast cell, a *C. intermedia* yeast cell, a *S. cerevisiae* yeast cell, a *D. hansenii* yeast cell, or a *Y. lipolytica* yeast cell.

II. EXAMPLES

Figure 8:
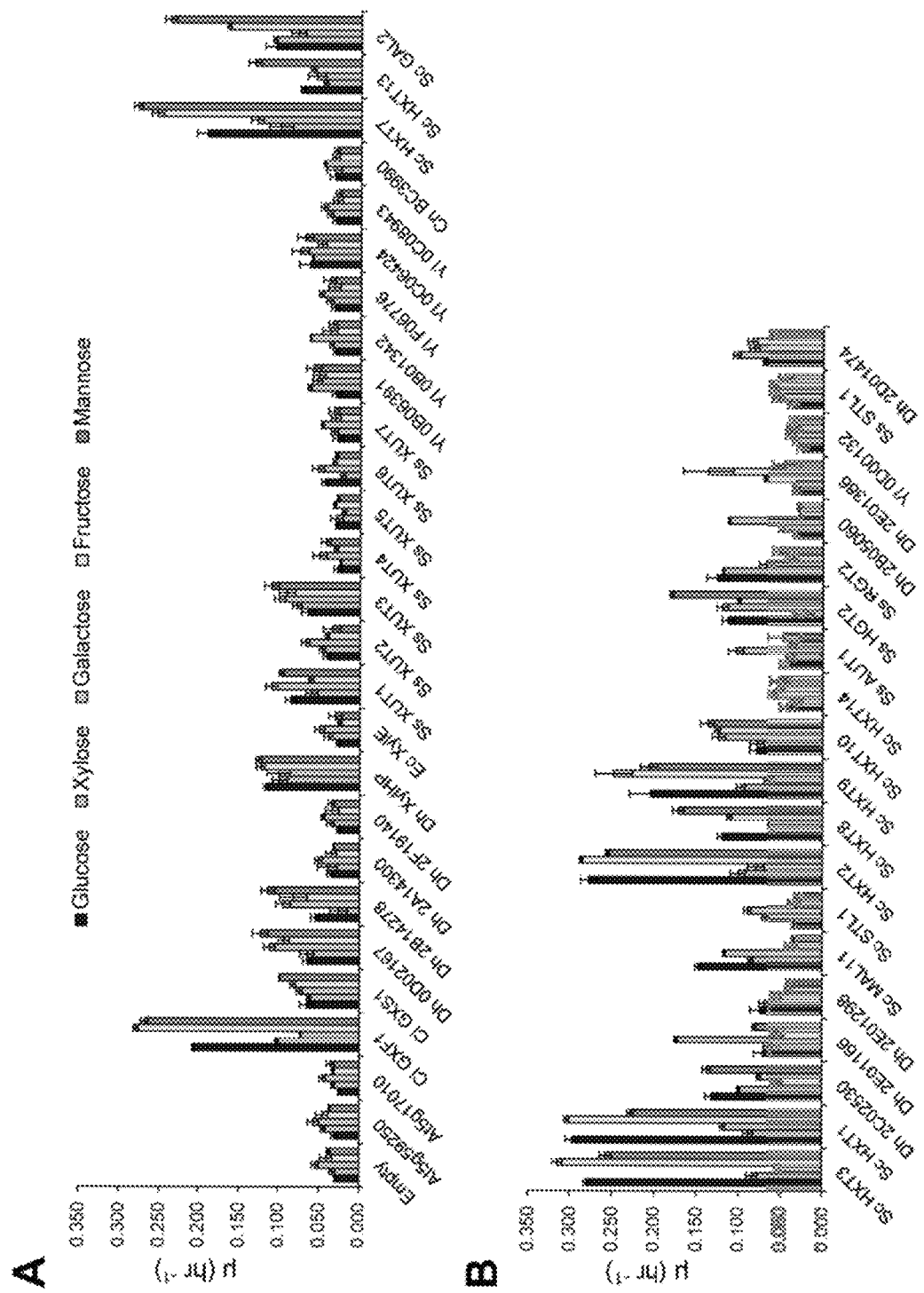
FIG. 8—Maximum exponential growth rates for all cloned native and heterologous transporters. Bar chart of growth rate (µ) calculated from growth curves of S. cerevisiae EX.12 measured on a Bioscreen C. Carbon source profiling on five different sugars allows better functional classification than measuring only glucose and xylose. Error is standard deviation of biological triplicates. A) Transporters cloned in the initial study measured for the first time in S. cerevisiae EX.12. B) Novel transporters identified and characterized. Abbreviations: Empty—empty vector control strain. A.t.—Arabidopsis thaliana. C.i.—Candida intermedia. C.n.—Cryptococcos neoformans. D.h.—Debaryomyces hansenii. S.c.—Saccharomyces cerevisiae. S.s.—Scheffersomyces stipitis. Y.l.—Yarrowia lipolytica.

Example 1: Identification of the G-G/F-XXX-G (SEQ ID NO: 29) Motif that Controls Sugar Transport Preference A multiple sequence alignment of 26 previously cloned transporters (36) indicates that Phe40 was part of a highly conserved glycine-rich motif of the form G-G/F-XXX-G (SEQ ID NO: 29), where X represents a variable, but usually nonpolar amino acid residue. In *C. intermedia* GXS 1, the wild type motif is G36G37V38L39F40G41. The high conservation of this motif suggested it could be responsible for xylose uptake, transporter efficiency, and monosaccharide selectivity. To further corroborate this hypothesis, an additional 20 putative transporters were identified using a BLAST search seeded with transporters functionally characterized in *S. cerevisiae* EX 12, a recombinant strain lacking endogenous monosaccharide transporters (FIG. 8 and Table 1) (26, 38). The vast majority of these transporters were functional and all possessed a similar motif. Among these transporters, *D. hansenii* 2D01474 confers much faster growth on xylose than on glucose and *S. stipitis* RGT2 confers the fastest growth on xylose of all the *S. stipitis* derived transporters in this study.

Following the functional characterization, motif sequence was correlated with transporter carbon source growth profile. Four major phenotypic classifications were made: (a) transporters that failed to function heterologously ($\mu$an=0), (b) transporters that conferred growth on a hexose but not xylose ($\mu$x=0), (c) transporters that conferred growth on xylose but not as fast as glucose ($\mu$x<$\mu$G) and (d) transporters that conferred a higher growth rate on xylose than on glucose ($\mu$x>$\mu$G). FIG. 1A displays the relative proportions of each of these classifications in the group of 46 transporters studied. To characterize the sequence, four major motif classifications were made: (a) a full G-G/F-XXXG (SEQ ID NO: 29) motif, (b) a related S-G-XXXG (SEQ ID NO: 31) motif, (c) a motif unrelated to the glycine rich motif, and (d) the lack of homology to other transporters at both the motif and surrounding residues. FIG. 1B depicts the distribution of the four sequence motif classifications within the four phenotypic classifications. Strikingly, there is a clear enrichment of the G-G/F-XXXG (SEQ ID NO: 29) motif among the functional transporters that enable high xylose transport rates. In fact, this motif is exclusively seen in phenotype class (d) where $\mu$x>$\mu$G. The enrichment and convergence of the variable residues within the motif is displayed in FIG. 1C. It should be noted that the consensus sequence from this analysis appears to be G-G/F-XX-F-G (SEQ ID NO: 32). Yet, variations at the consensus F residue led to the discovery of the motif, therefore this position was considered variable. FIG. 1C highlights the strong correlation between sequence motif and xylose transport function and suggests an important role of TMS1 on sugar recognition.

Identification of potentiating variable residues within the G-G/F-X-X-X-G (SEQ ID NO: 29) motif.

Figure 2:
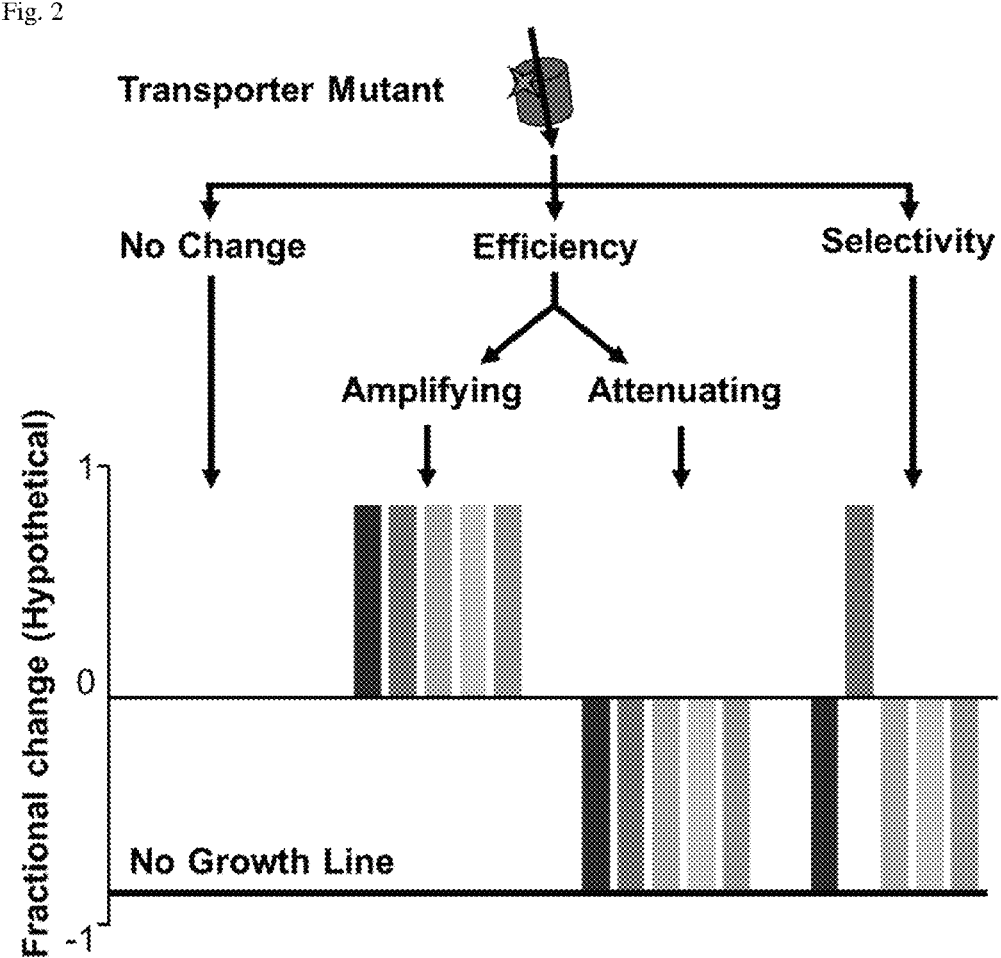
FIG. 2—Classification tree of fractional change in carbon source growth profile. This Fig. depicts hypothetical fractional change data in order to demonstrate how these phenotypes were classified. Little fractional change across all sugars indicates that the substitution does not control efficiency or selectivity in this background Amplification or attenuation of growth rates across all carbon sources indicates an efficiency substitution Amplification of growth on one sugar, ideally xylose, and attenuation of all others indicates a selectivity substitution.

To examine the role of the variable region, complete saturation mutagenesis was performed for each of the three residues (Val$^{38}$, Leu$^{39}$, and Phe$^{40}$) in *C. intermedia* GXS1 and evaluated the impact on carbon source growth profile as measured by growth rate. Previous studies demonstrate that growth rate in this test strain is a good surrogate for transporter kinetics (36, 38). Specifically, the fractional change in growth rate of *S. cerevisiae* EX.12 on glucose, xylose, galactose, fructose, or mannose as the sole carbon source was evaluated compared to the wild-type transporter. The impact of each residue can be classified as having no change, altered efficiency, altered selectivity, or a combination of the three (FIG. 2). For creating xylose specific transporters, the goal is to identify mutations that attenuate hexose growth while either amplifying or maintaining xylose growth.

Figure 3:
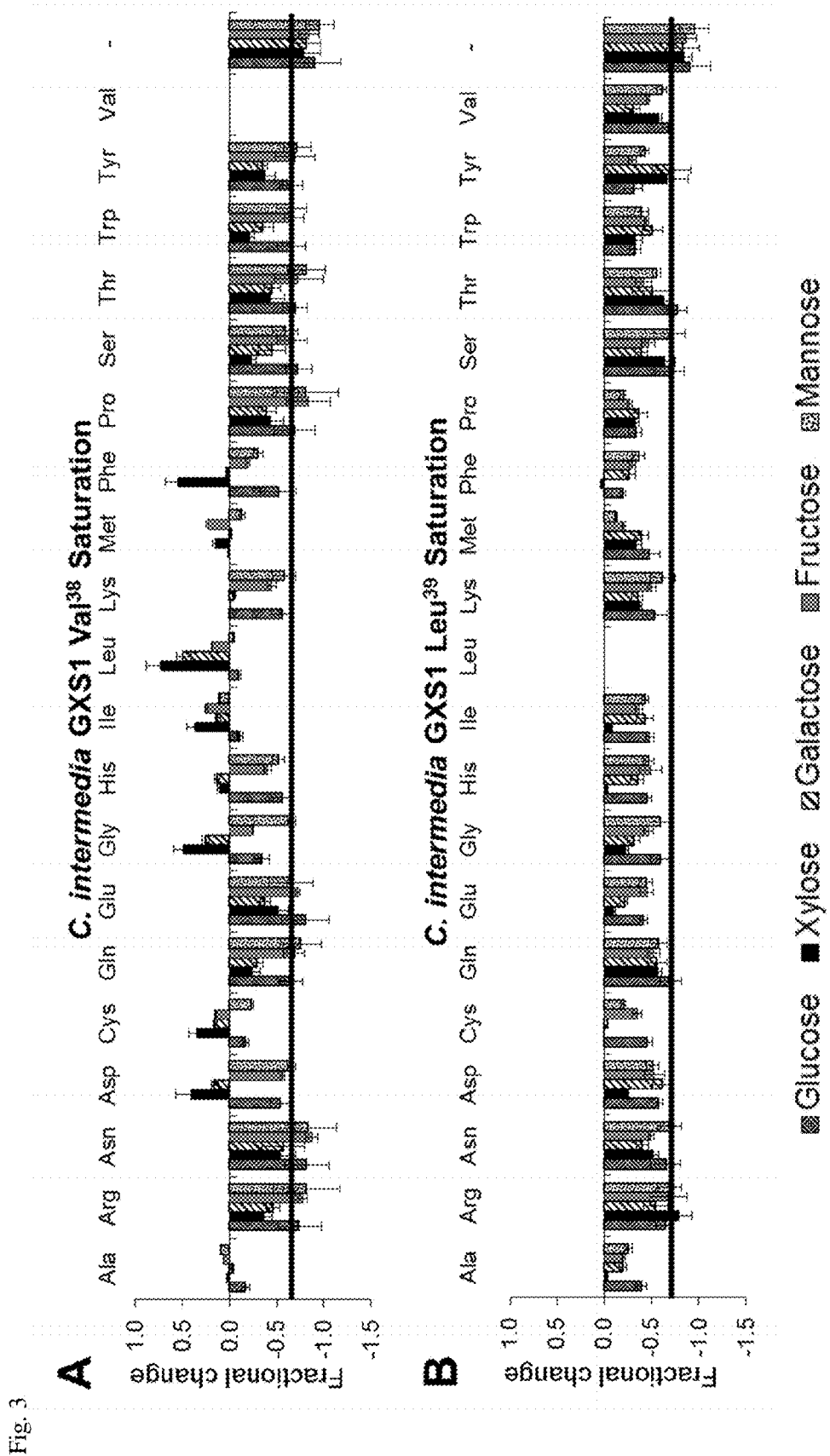
FIG. 3—Fractional change of saturation mutagenesis libraries of C. intermedia GXS1. A) Fractional change in growth by substitutions at position 38. B) Fractional change in growth by substitutions at position 39. C) Fractional change in growth by substitutions at position 40. The solid line is the confidence line for no growth based on the negative control sample.

Members of the *C. intermedia* gxs1 Val$^{38}$ saturation library (FIG. 3A) display differential exponential growth rates with the most significant one being the Phe$^{38}$ substitution. frequency of selectivity and differentially attenuating phenotypes arising at this residue indicates that position 38 predominately influences monosaccharide selectivity.

TABLE 1

Exponential growth rate values for each cloned transporter

| | | | Glucose | | Xylose | | Galactose | | Fructose | | Mannose | |
|---|---|---|---|---|---|---|---|---|---|---|---|---|
| | GeneID | GenBank | μ (1/hr) | st. dev | μ (1/hr) | st. dev | μ (1/hr) | st. dev | μ (1/hr) | st. dev | μ (1/hr) | st. dev |
| Empty | — | — | 0.028 | 0.002 | 0.033 | 0.004 | 0.054 | 0.004 | 0.041 | 0.008 | 0.038 | 0.002 |
| At5g59250 | 836043 | | 0.031 | 0.004 | 0.045 | 0.003 | 0.057 | 0.007 | 0.046 | 0.008 | 0.037 | 0.001 |
| At5g17010 | 831564 | | 0.024 | 0.002 | 0.032 | 0.002 | 0.046 | 0.004 | 0.032 | 0.002 | 0.036 | 0.005 |
| Ci GXF1 | | AJ937350.1 | 0.206 | 0.002 | 0.101 | 0.003 | 0.072 | 0.000 | 0.278 | 0.003 | 0.268 | 0.004 |
| Ci GXS1 | | AJ875406.1 | 0.065 | 0.008 | 0.062 | 0.002 | 0.074 | 0.004 | 0.082 | 0.003 | 0.098 | 0.000 |
| Dh 0D02167 | 2901237 | | 0.064 | 0.005 | 0.065 | 0.008 | 0.111 | 0.007 | 0.093 | 0.007 | 0.123 | 0.010 |
| Dh 2B14278 | 2913528 | | 0.055 | 0.005 | 0.026 | 0.011 | 0.094 | 0.009 | 0.081 | 0.017 | 0.114 | 0.009 |
| Dh 2A14300 | 8998057 | | 0.036 | 0.004 | 0.040 | 0.013 | 0.051 | 0.004 | 0.035 | 0.007 | 0.032 | 0.001 |
| Dh 2F19140 | 8999011 | | 0.026 | 0.002 | 0.036 | 0.005 | 0.046 | 0.002 | 0.034 | 0.009 | 0.035 | 0.004 |
| Dh XylHP | 50419268 | | 0.116 | 0.003 | 0.098 | 0.010 | 0.100 | 0.014 | 0.123 | 0.006 | 0.126 | 0.004 |
| Ec XylE | 948529 | | 0.026 | 0.002 | 0.039 | 0.006 | 0.050 | 0.006 | 0.024 | 0.002 | 0.030 | 0.009 |
| Ss XUT1 | 4839826 | | 0.085 | 0.007 | 0.060 | 0.007 | 0.109 | 0.008 | 0.060 | 0.003 | 0.096 | 0.003 |
| Ss XUT2 | 4852047 | | 0.042 | 0.005 | 0.047 | 0.004 | 0.067 | 0.005 | 0.041 | 0.002 | 0.035 | 0.011 |
| Ss XUT3 | 4851844 | | 0.064 | 0.008 | 0.078 | 0.005 | 0.099 | 0.007 | 0.090 | 0.010 | 0.109 | 0.009 |
| Ss XUT4 | 4840896 | | 0.027 | 0.005 | 0.024 | 0.001 | 0.050 | 0.009 | 0.029 | 0.003 | 0.043 | 0.006 |
| Ss XUT5 | 4840252 | | 0.029 | 0.001 | 0.029 | 0.008 | 0.020 | 0.003 | 0.031 | 0.002 | 0.027 | 0.002 |
| Ss XUT6 | 4841106 | | 0.044 | 0.004 | 0.021 | 0.003 | 0.053 | 0.007 | 0.032 | 0.003 | 0.029 | 0.002 |
| Ss XUT7 | 4851701 | | 0.028 | 0.008 | 0.032 | 0.005 | 0.048 | 0.001 | 0.030 | 0.006 | 0.033 | 0.007 |
| Yl 0B06391 | 2907283 | | 0.030 | 0.006 | 0.063 | 0.002 | 0.054 | 0.006 | 0.051 | 0.007 | 0.058 | 0.009 |
| Yl 0B01342 | 2906708 | | 0.031 | 0.003 | 0.036 | 0.003 | 0.062 | 0.001 | 0.038 | 0.010 | 0.035 | 0.005 |
| Yl F06776 | 2908504 | | 0.032 | 0.005 | 0.039 | 0.004 | 0.049 | 0.003 | 0.033 | 0.008 | 0.039 | 0.008 |
| Yl 0C06424 | 2909312 | | 0.063 | 0.013 | 0.059 | 0.001 | 0.075 | 0.010 | 0.048 | 0.005 | 0.069 | 0.010 |
| Yl 0C08943 | 2909701 | | 0.031 | 0.005 | 0.039 | 0.003 | 0.046 | 0.004 | 0.029 | 0.007 | 0.027 | 0.003 |
| Cn BC3990 | 4935064 | | 0.031 | 0.008 | 0.034 | 0.010 | 0.045 | 0.001 | 0.032 | 0.005 | 0.030 | 0.004 |
| Sc HXT7 | 851943 | | 0.191 | 0.013 | 0.099 | 0.015 | 0.130 | 0.008 | 0.254 | 0.008 | 0.278 | 0.005 |
| Sc HXT13 | 856640 | | 0.072 | 0.003 | 0.045 | 0.003 | 0.055 | 0.011 | 0.059 | 0.003 | 0.132 | 0.008 |
| Sc GAL2 | 856640 | | 0.105 | 0.013 | 0.107 | 0.003 | 0.078 | 0.009 | 0.164 | 0.003 | 0.237 | 0.008 |
| Sc HXT3 | 851946 | | 0.280 | 0.003 | 0.083 | 0.006 | 0.053 | 0.002 | 0.314 | 0.006 | 0.258 | 0.007 |
| Sc HXT1 | 856494 | | 0.297 | 0.008 | 0.088 | 0.006 | 0.118 | 0.003 | 0.303 | 0.003 | 0.229 | 0.004 |
| Dh 2C02530 | 8998297 | | 0.132 | 0.007 | 0.099 | 0.002 | 0.055 | 0.006 | 0.075 | 0.002 | 0.138 | 0.005 |
| Dh 2E01166 | 2902950 | | 0.071 | 0.010 | 0.061 | 0.010 | 0.174 | 0.002 | 0.054 | 0.007 | 0.081 | 0.002 |
| Dh 2E01298 | 2902912 | | 0.074 | 0.011 | 0.069 | 0.006 | 0.056 | 0.005 | 0.041 | 0.002 | 0.040 | 0.002 |
| Sc MAL11 | 853207 | | 0.148 | 0.004 | 0.085 | 0.003 | 0.117 | 0.001 | 0.038 | 0.006 | 0.034 | 0.002 |
| Sc STL1 | 852149 | | 0.034 | 0.001 | 0.069 | 0.003 | 0.089 | 0.004 | 0.344 | 0.006 | 0.029 | 0.004 |
| Sc HXT2 | 855023 | | 0.278 | 0.009 | 0.101 | 0.009 | 0.079 | 0.009 | 0.287 | 0.002 | 0.256 | 0.002 |
| Sc HXT8 | 853216 | | 0.120 | 0.005 | 0.060 | 0.000 | 0.064 | 0.001 | 0.111 | 0.003 | 0.172 | 0.007 |
| Sc HXT9 | 853236 | | 0.205 | 0.026 | 0.098 | 0.005 | 0.065 | 0.005 | 0.249 | 0.022 | 0.207 | 0.011 |
| Sc HXT10 | 850536 | | 0.079 | 0.009 | 0.078 | 0.008 | 0.124 | 0.008 | 0.125 | 0.003 | 0.137 | 0.009 |
| Sc HXT14 | 855398 | | 0.042 | 0.009 | 0.032 | 0.006 | 0.061 | 0.005 | 0.051 | 0.003 | 0.051 | 0.012 |
| Ss AUT1 | 4836720 | | 0.046 | 0.005 | 0.038 | 0.004 | 0.104 | 0.009 | 0.035 | 0.004 | 0.046 | 0.019 |
| Ss HGT2 | 4836632 | | 0.113 | 0.007 | 0.024 | 0.010 | 0.120 | 0.007 | 0.100 | 0.002 | 0.179 | 0.002 |
| Ss RGT2 | 4840859 | | 0.126 | 0.013 | 0.119 | 0.001 | 0.068 | 0.008 | 0.038 | 0.007 | 0.053 | 0.006 |
| Dh 2B05060 | 2913215 | | 0.033 | 0.003 | 0.050 | 0.002 | 0.112 | 0.001 | 0.028 | 0.001 | 0.029 | 0.001 |
| Dh 2E01386 | 2902914 | | 0.032 | 0.004 | 0.035 | 0.001 | 0.069 | 0.002 | 0.137 | 0.030 | 0.045 | 0.015 |
| Yl 0D00132 | 2910370 | | 0.026 | 0.006 | 0.034 | 0.002 | 0.039 | 0.005 | 0.035 | 0.007 | 0.035 | 0.005 |
| Ss STL1 | 4838168 | | 0.037 | 0.006 | 0.055 | 0.006 | 0.060 | 0.005 | 0.061 | 0.004 | 0.045 | 0.008 |
| Dh 2D01474 | 2901237 | | 0.072 | 0.000 | 0.104 | 0.004 | 0.062 | 0.006 | 0.085 | 0.006 | 0.061 | 0.004 | tution. This mutant confers a selectivity phenotype that almost completely attenuates glucose exponential growth rate while amplifying exponential xylose growth rate by 50%. Other substitutions that confer desirable selectivity phenotypes are Asp$^{38}$, Cys$^{38}$, Gly$^{38}$, and His$^{38}$. All of these affect the growth profile in different patterns, but none as significantly as Phe$^{38}$. Three substitutions, Ile$^{38}$, Leu$^{38}$, and Met$^{38}$, differentially amplify growth on multiple sugars while glucose growth remains unchanged. The Leu$^{38}$ substitution in particular increases exponential xylose growth rate by 73% without altering glucose exponential growth rate significantly. Ala$^{38}$ attenuates growth on glucose only. Nearly all of the remaining substitutions attenuate growth, yet many preferentially attenuate growth on hexoses. In this subset, Lys$^{38}$ attenuates growth on glucose, fructose, and mannose without affecting growth rate on xylose. The Nearly all members of the Leu$^{39}$ saturation library (FIG. 3B) display uniform attenuation patterns across sugars. Thus, residue 39 appears to greatly control transporter efficiency. Nevertheless, several of these substitutions differentially attenuate growth. Specifically, Asp$^{39}$, Cys$^{39}$, Gly$^{39}$, His$^{39}$, Ile$^{39}$, and Phe$^{39}$ reduce exponential growth on hexoses without drastically altering xylose growth rate. Of these, His$^{39}$ and Ile$^{39}$ establish the greatest difference between the hexose and pentose growth rates.

Members of the Phe$^{40}$ library (FIG. 3C) display differential carbon source selectivity similar to Val$^{38}$ and have the greatest frequency of selectivity substitutions. Specifically, amino acid substitutions that confer a selectivity phenotype for xylose over glucose are Asn$^{40}$, Cys$^{40}$, Gly$^{40}$, Leu$^{40}$, Met$^{40}$, Ser$^{40}$, and Thr$^{40}$. Of these, Ser$^{40}$ and Met$^{40}$ appear as the most significant. There are several attenuating substitutions that can be seen at residue 40 including Are, Asp$^{40}$, Glu$^{40}$, Ile$^{40}$, Lys$^{40}$, Pro$^{40}$, and Tyr$^{40}$. Of these, Pro$^{40}$ appears as the only one that does not attenuate growth on xylose. Finally, Ala$^{40}$, His$^{40}$, and Trp$^{40}$ confer increased growth on most of the monosaccharides tested. In summary, residues 38 and 40 appear to play a role in transporter selectivity while residue 39 appears to play a role for controlling net transporter efficiency. In general, hydrophobic residues of moderate to large size were beneficial for xylose growth, while charged residues were not (also seen with the evaluated transporters in FIG. 1C). These motif design guidelines may be used to reprogram transporter function.

Rewiring *C. intermedia* GXS1 into a Xylose Specific Transporter.

Figure 4:
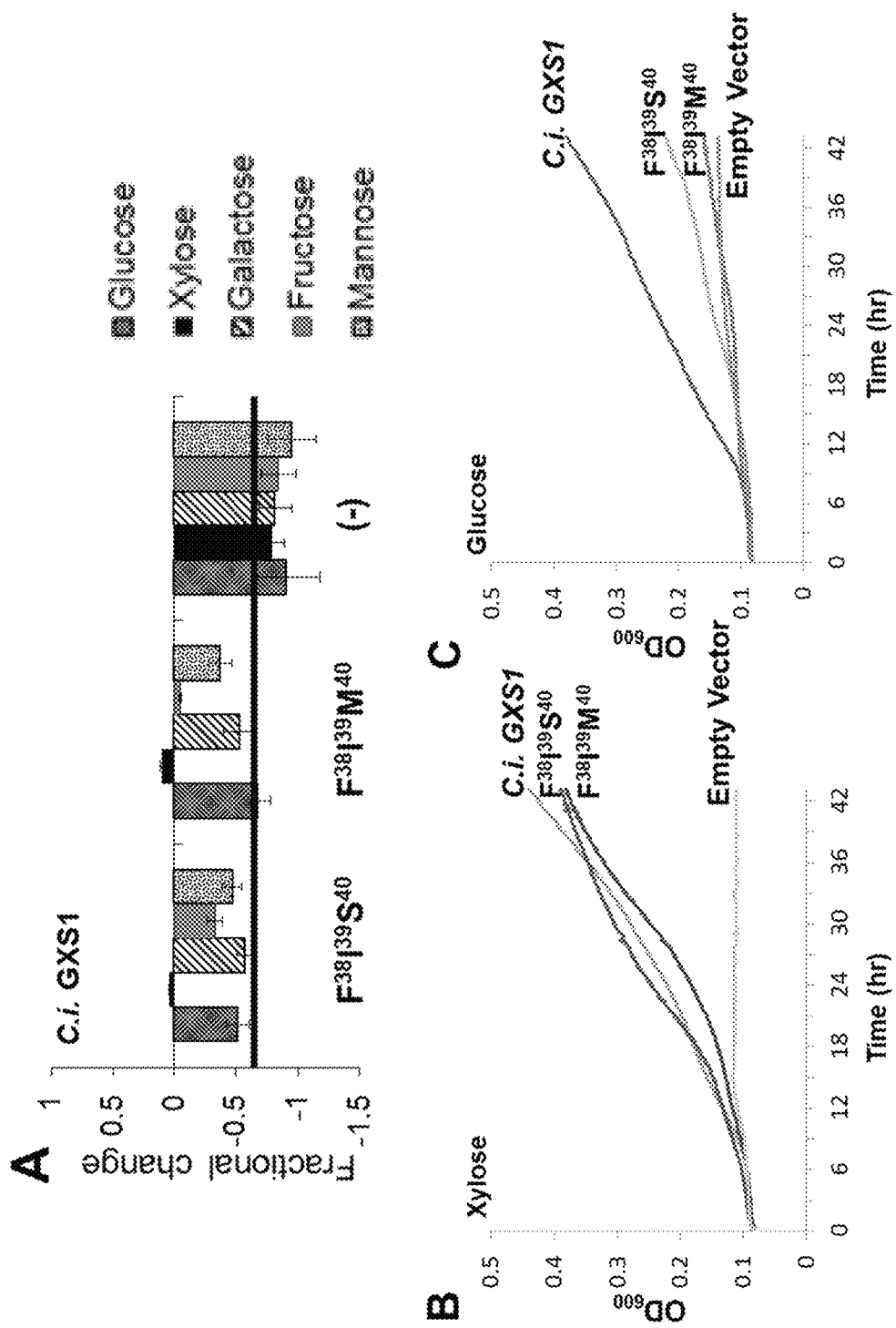
FIG. 4—Growth characterization of C. intermedia gxs1 triple mutants. A) Fractional change from wild type for the two triple mutants and an empty vector control. B) Average growth curves on xylose based on optical density at 600 nm C) Average growth curves on glucose based on optical density at 600 nm.
Figure 9:
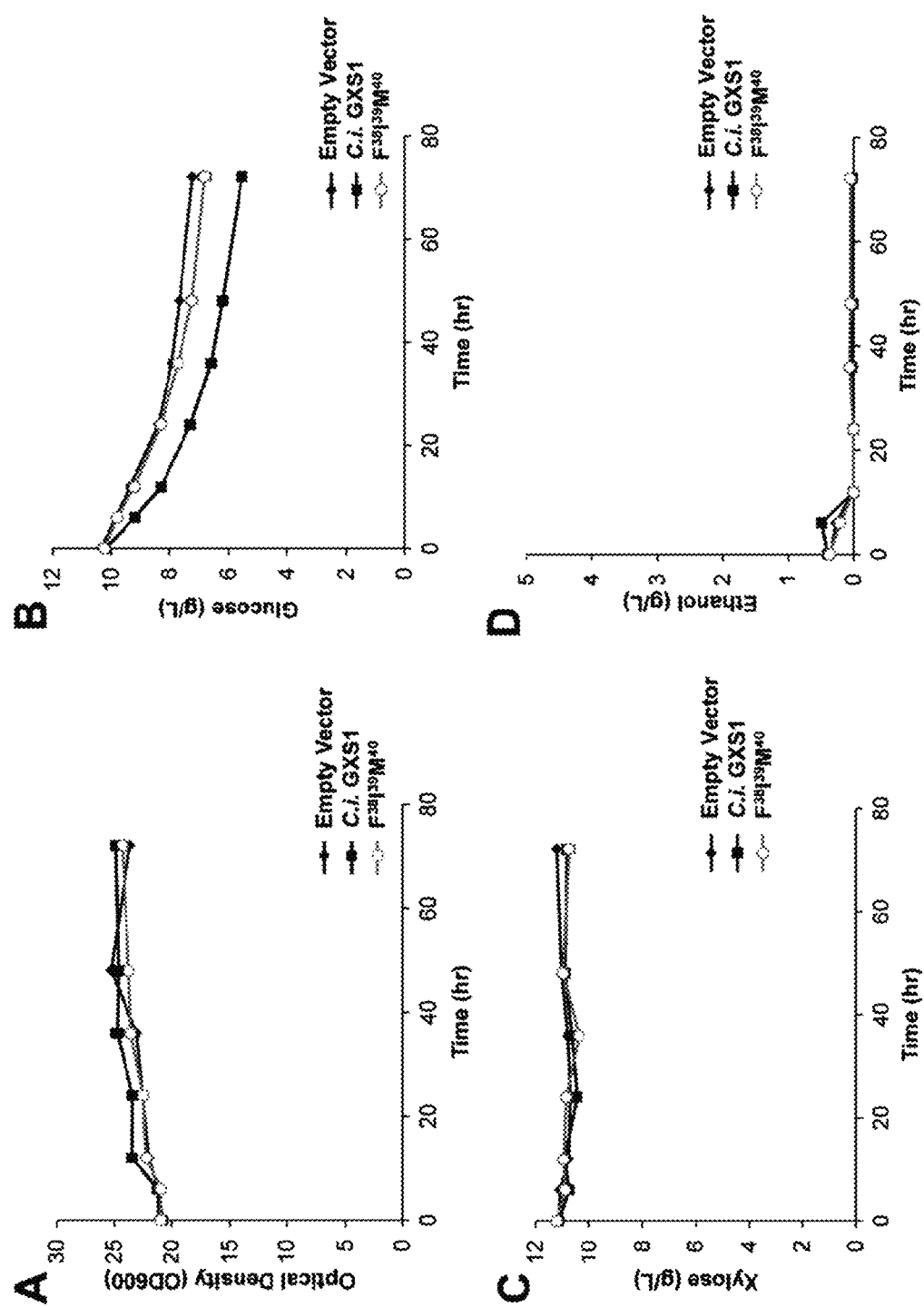
FIG. 9—High cell density cofermentation in S. cerevisiae EX.12. Cells were inoculated at OD 20 in a mixture of 10 g/L glucose and 10 g/L xylose. Optical density, glucose, xylose, and ethanol concentration was measured over the length of the fermentation. Note that the triple mutant does not consume either xylose or glucose, nor is an appreciable amount of ethanol produced in this multiple knockout strain. A) Optical density over time. B) Glucose concentration in the media over time. C) Xylose concentration in the media over time. D) Ethanol concentration in the media over time.
Figure 10:
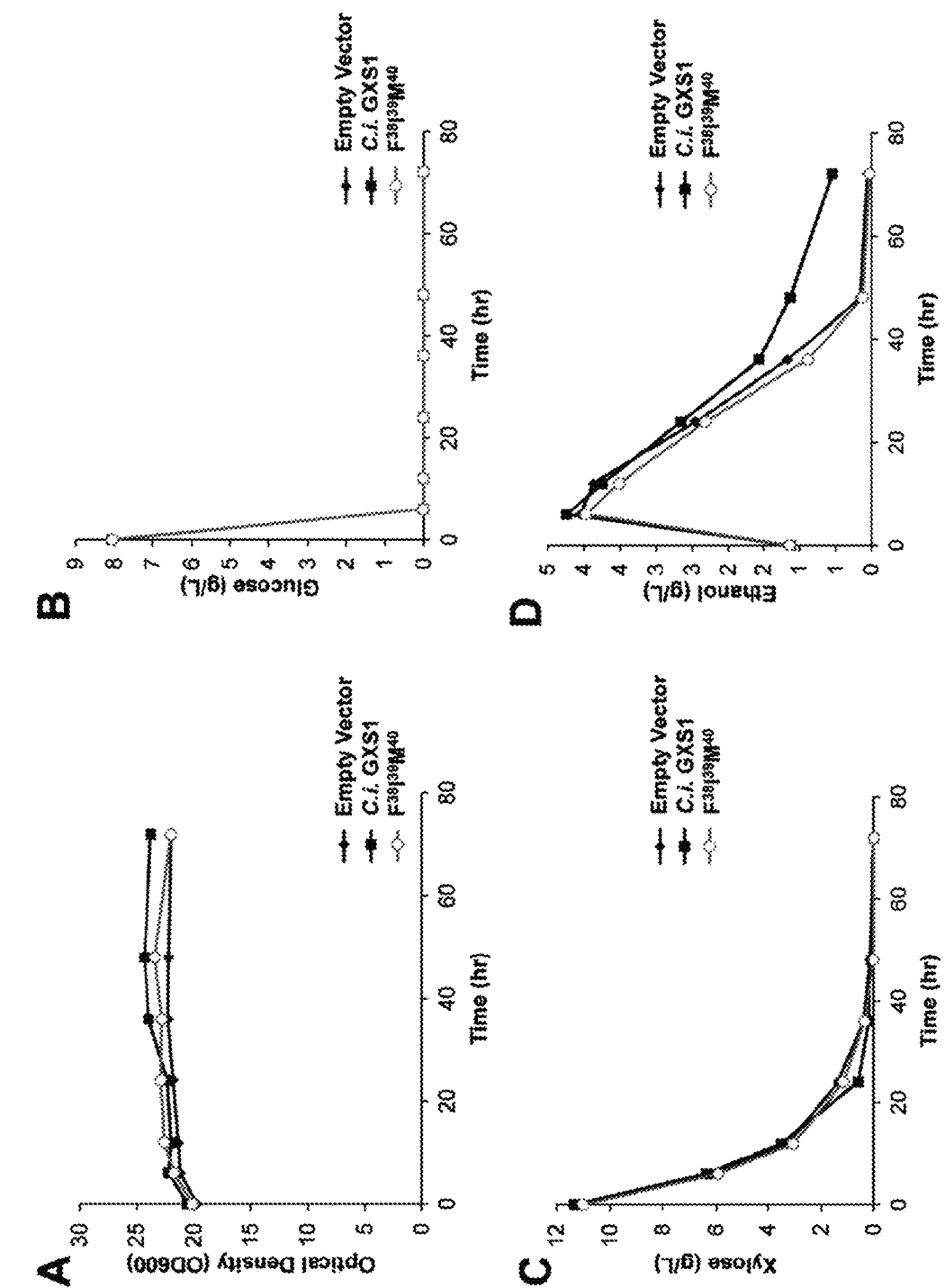
FIG. 10—High cell density cofermentation in S. cerevisiae YSX3. Cells were inoculated at OD 20 in a mixture of 10 g/L glucose and 10 g/L xylose. Optical density, glucose, xylose, and ethanol concentration was measured over the length of the fermentation. Note that the triple mutant does not appreciably alter the fermentation dynamics in a strain that is expressing the full suite of transporters. A) Optical density over time B) Glucose concentration in the media over time. C) Xylose concentration in the media over time. D) Ethanol concentration in the media over time.

Using the design guidelines discovered above, triple mutants were constructed to investigate the synergy between xylose favoring substitutions (in particular, Phe$^{38}$, Ile$^{39}$, and Ser$^{40}$/Met$^{40}$). Both Phe$^{38}$ Ile$^{39}$ Ser$^{40}$ and Phe$^{38}$ Ile$^{39}$ Met$^{40}$ attenuate glucose exponential growth while maintaining or slightly increasing xylose exponential growth (FIG. 4A), with the Phe$^{38}$ Ile$^{39}$ Met$^{40}$ triple mutant attenuating glucose growth to the same level as the negative control. Average growth curves on xylose and glucose (FIG. 4B-C) highlight that both triple mutants maintain wild-type xylose growth profile while severely attenuate glucose growth. Further characterization of the best mutant, gxs1 Phe$^{38}$ Ile$^{39}$ Met$^{40}$ was performed. First, to assay transport capacity, high cell density fermentations with xylose and glucose were performed (FIG. 5A-B). The Phe$^{38}$ Ile$^{39}$ Met$^{40}$ triple mutant displayed no appreciable glucose uptake whereas xylose uptake has become more efficient compared to the wild-type GXS1. These results display a rewiring of the sugar uptake ratio. However, despite minimizing glucose transport capacity, glucose at levels of 5 g/L still appear to inhibit xylose growth (FIG. 5C). This finding is corroborated by high cell density cofermentations (FIG. 9 and FIG. 10).

Radiolabelled xylose uptake experiments were performed to quantify the improvement of transport kinetics in the Phe$^{38}$ Ile$^{39}$ Met$^{40}$ triple mutant. The improvements in xylose utilization observed at high cell density culturing were mainly due to a doubling in $V_{max}$ (FIG. 5D). An increased $K_M$ was observed as well (FIG. 5E), a phenotype observed in previous efforts to engineer this transporter (38). Nevertheless, the binding affinity is still quite high for practical culturing at a value corresponding to around 0.1 g/L (Table 2). These kinetics experiments were also performed in the presence of glucose and no radiolabelled xylose uptake was detected indicating that while glucose cannot pass through the transporter, it can still bind and inhibit xylose uptake. Hence, binding appears to occur at a different residue.

TABLE 2 kinetics values calculated from radiolabeled xylose uptake

| Gene in p414-TEF | $K_M$ (mM) | $V_{MAX}$ (nmol min$^{-1}$ gDCW$^{-1}$) |
| --- | --- | --- |
| C.i. GXS1 | 0.0256 ± 0.0659 | 7.23 ± 0.6 |
| C.i. GXS1 F$^{38}$I$^{39}$M$^{40}$ | 0.721 ± 0.116 | 15.01 ± 2.38 |

The G-G/F-XXXG Motif can be used to Rewire Other Transporters

Figure 6:
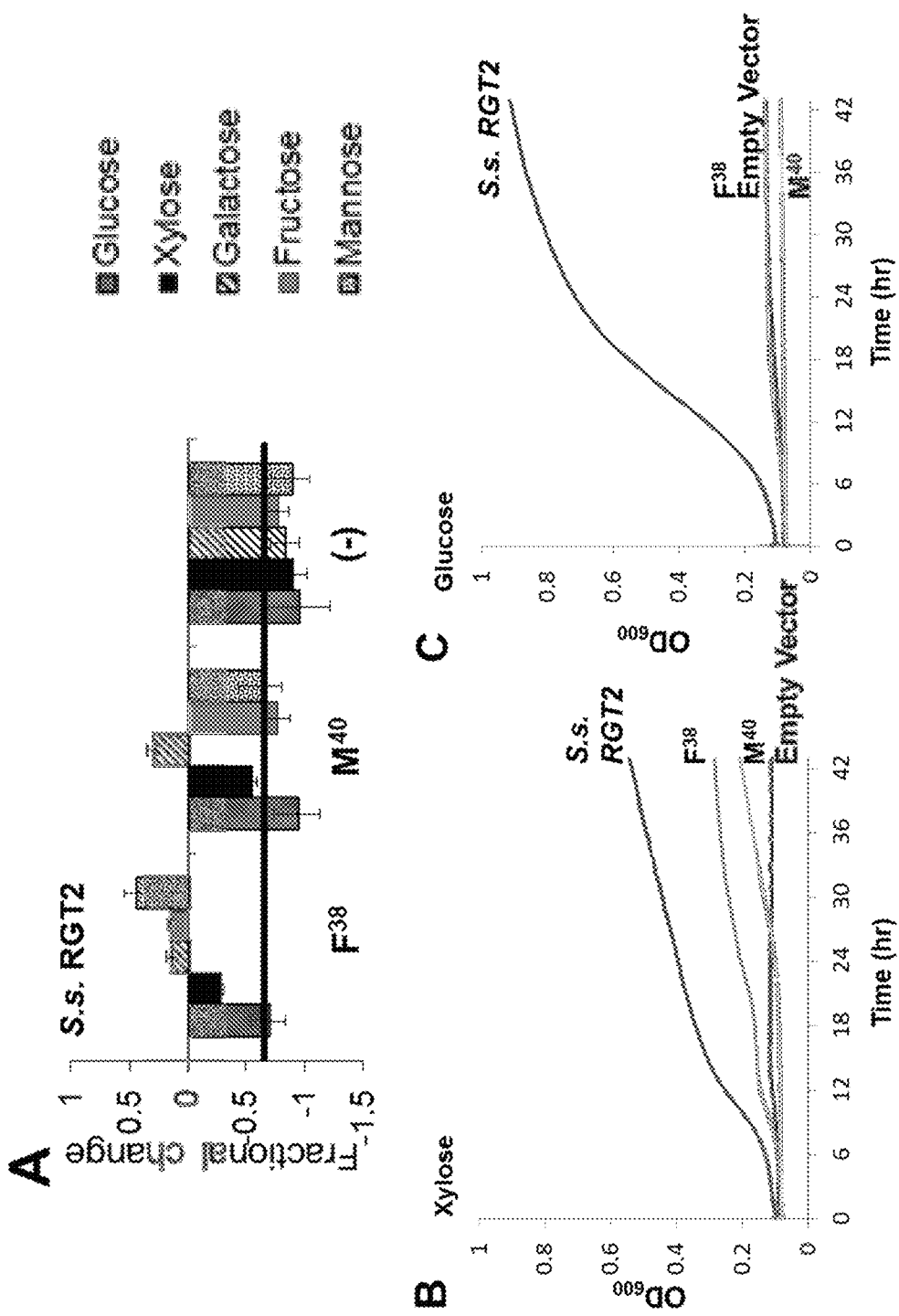
FIG. 6—Growth characterization of S. stipitis RGT2 and mutants. A) Fractional change from wild type for the two single mutants and an empty vector control. B) Average growth curves on xylose based on optical density at 600 nm C) Average growth curves on glucose based on optical density at 600 nm.
Figure 11:
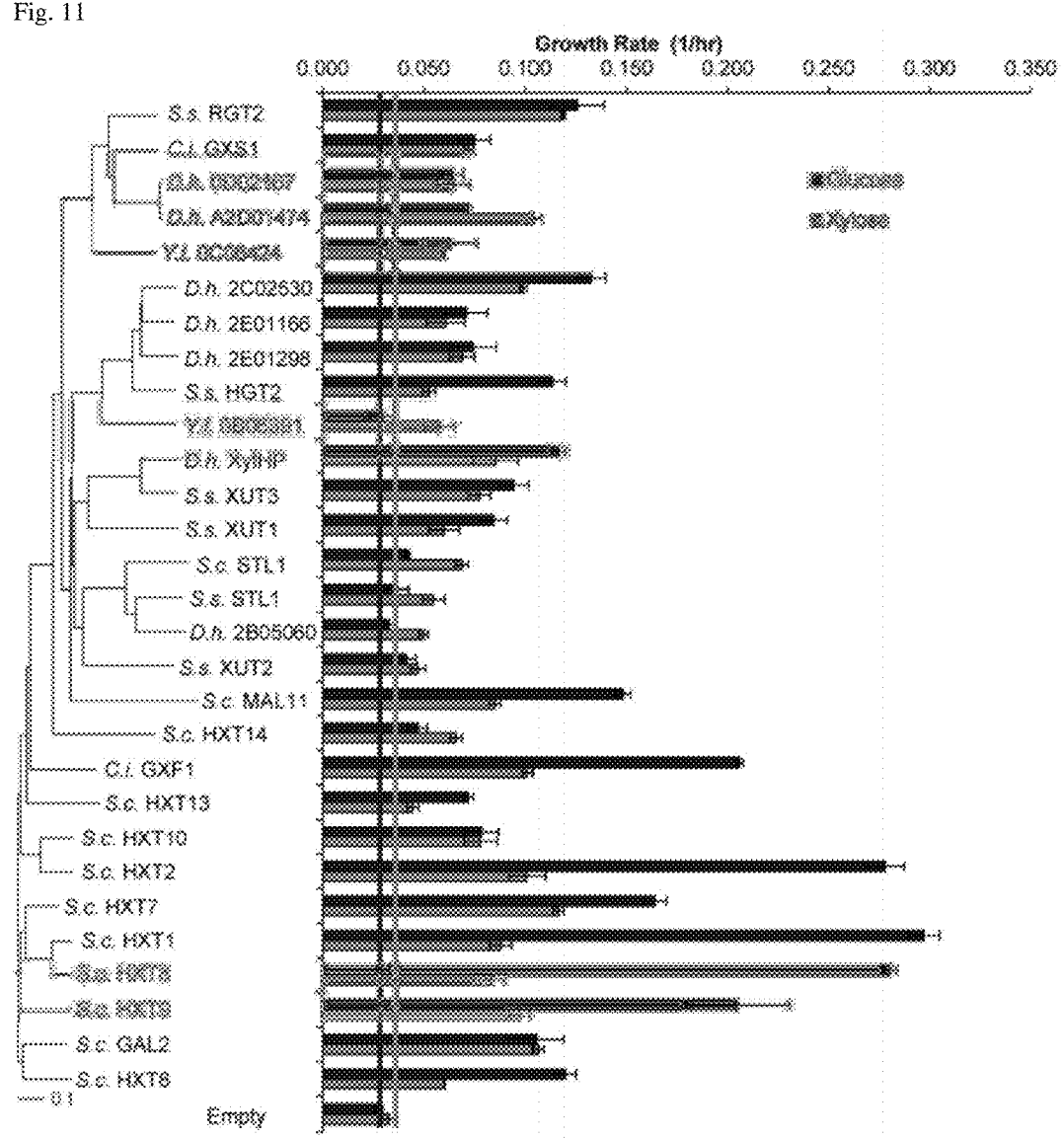
FIG. 11—Growth curves of transporters of interest. Optical density measurements from the Bioscreen C were plotted over time. Each line represents the growth curve for S. cerevisiae EX.12 expressing a transporter on a particular carbon source. A) D.h. 2D01474. B) S.s. RGT2. C) D.h. 2E01166. D) D.h. 2B05060. E) S. c. STL1. F) S.s. AUT1.
Figure 12:
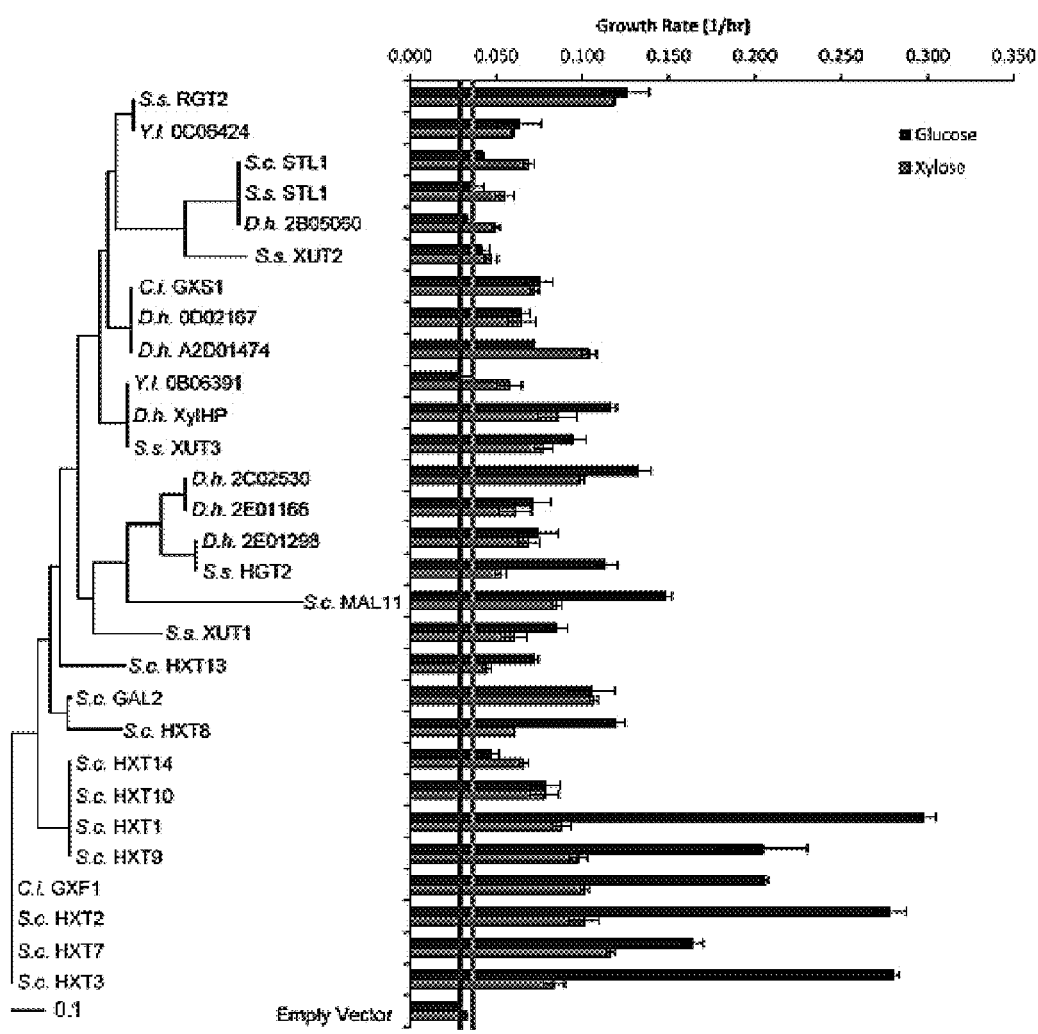
FIG. 12—Phylogenetic tree and growth rate. Phylogram constructed in TreeView of a ClustalW multiple sequence alignment with the full amino acid sequences of all transporters. To the right of the phylogram is plotted the exponential growth rate of S. cerevisiae EX.12 conferred by transporter expression. A blue line and a green line are placed across the chart to mark the upper limit of no growth for glucose and xylose, respectively. Note the most robust glucose growth phenotypes are clustered in the HXT family and related transporters. Some of the more desirable growth phenotypes for xylose growth are clustered in the transporters related to C. i. GXS1 and S.s. XUT3.

To test how broad these design guidelines are for transporters, the conserved G-G/F-XXXG motif was utilized to reengineer the sugar preference of other predominately hexose transporters. Specifically, two transporters, *S. stipitis* RGT2 and *S. cerevisiae* HXT7, were selected based on evolutionary distance from GXS1. *S. stipitis* RGT2 is closely related to *C. intermedia* GXS1, while the native HXT transporters are more distant (FIGS. 11 and 12). First, the impact of rewiring the closely related transporter, *S. stipitis* RGT2 was investigated. This transporter contains a G$^{36}$G$^{37}$I$^{38}$L$^{39}$F$^{40}$G$^{41}$ motif and two separate point mutations were characterized, Phe$^{38}$ and Met$^{40}$. In both cases, glucose growth has been completely attenuated (FIG. 6). Most striking is the Met$^{40}$ mutation, which eliminates growth on all carbon sources but xylose and galactose. By modifying the motif in RGT2, two additional mutant proteins were generated that transport xylose, but not glucose.

Figure 7:
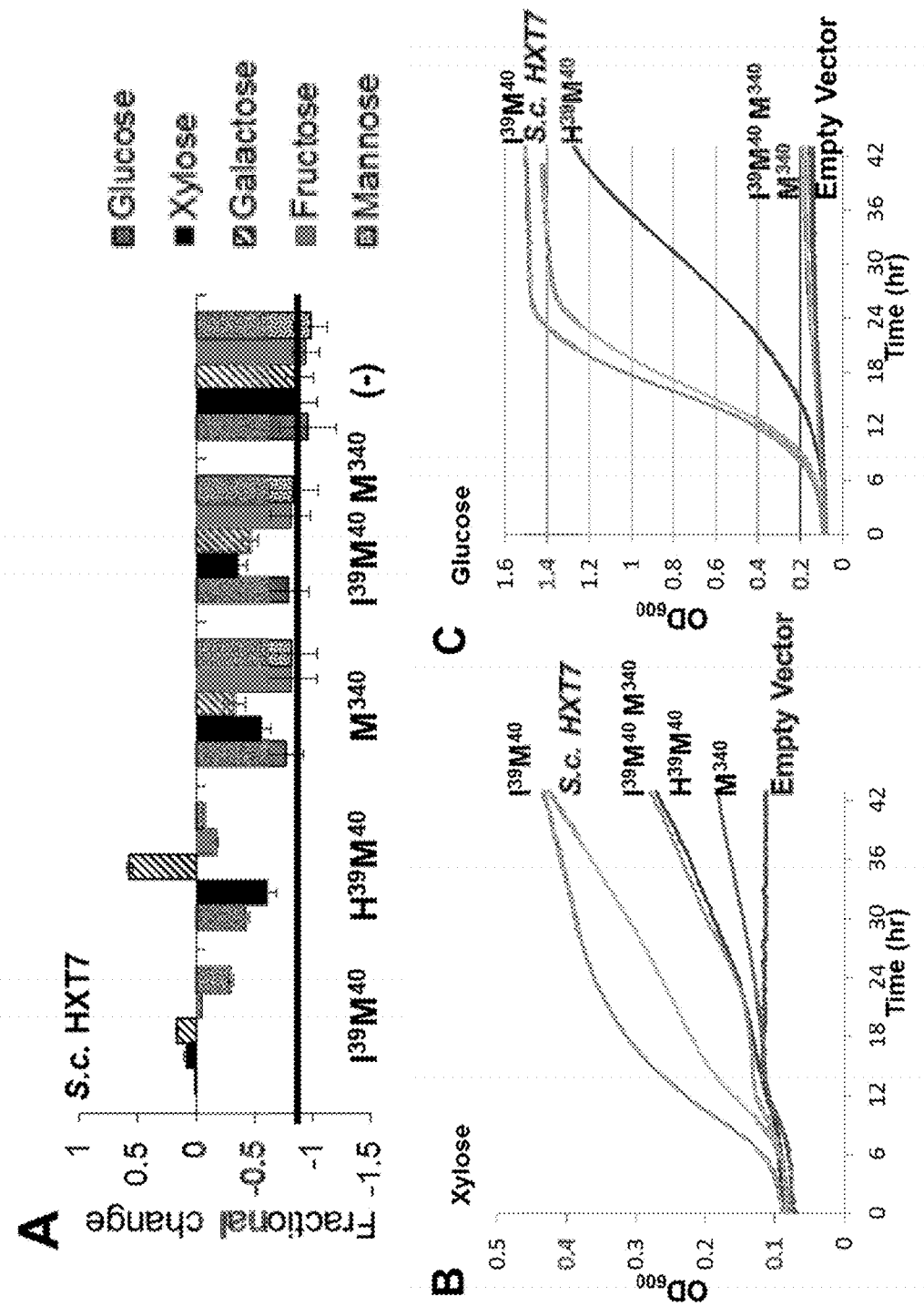
FIG. 7—Growth characterization of S. cerevisiae HXT7 and mutants. A) Fractional change from wild type for the mutants and an empty vector control. B) Average growth curves on xylose based on optical density at 600 nm C) Average growth curves on glucose based on optical density at 600 nm.

Second, the potential to rewire *S. cerevisiae* HXT7, a more distantly related protein yet is able to efficiently transport hexoses and xylose in yeast, was evaluated (32, 42). Given the proficiency of hexose transport by this protein, rewiring to attenuate growth on hexoses presents a greater challenge. The native motif within *S. cerevisiae* HXT7 is G$^{36}$G$^{37}$F$^{38}$V$^{39}$F$^{40}$G$^{41}$. Two double mutations to this motif-Ile$^{39}$Met$^{40}$ and His$^{39}$Met$^{40}$ were initially evaluated. FIG. 7 demonstrates that the Ile$^{39}$Met$^{40}$ double mutant amplified xylose exponential growth and attenuated growth on all hexoses save glucose whereas the His$^{39}$Met$^{40}$ double mutant attenuated glucose growth yet also severely attenuated xylose exponential growth. Previous studies have indicated that mutations at Asp$^{340}$ can eliminate glucose transport (39) in HXT7 and transport of nearly all monosaccharides is severely attenuated with this mutation was verify herein (FIG. 7). Coupling the Met$^{340}$ mutation with the Ile$^{39}$Met$^{40}$ double mutant resulted in robust growth on xylose while maintaining the inability to transport glucose. With this triple mutant, a robust hexose transporter was converted to a xylose transporter unable to support growth on glucose.

Thus, a short, six residue motif of the form G-G/F-XXXG in TMS1 was identified that exerts control over selectivity and efficiency of monosaccharide transport of MFS family transporters. This motif is conserved among functional transporters and highly enriched in transporters that confer growth on xylose. Altering the composition of the variable region changes the sugar uptake profiles of these transporters and can thus be used to rewire transporter function. Altering the residues in this domain can eliminate glucose transport while retaining xylose transport, a major step forward for molecular transporter engineering. As a result, several transporter mutants were create that support the transport of xylose and not glucose.

Hydrophobic, nonpolar, and moderate to large size residues often attenuated glucose compared to xylose Amino acids such as Phe, Ile, Ser, and Met were among the most effective substitutions that differentially amplified xylose growth rate. While many of these residues are found naturally in wild type motif sequences (FIG. 2), the combinations found herein (particularly Phe$^{38}$Ile$^{39}$ Met$^{40}$) are not found naturally. Hypotheses concerning transporter substrate recognition and transport mechanism may be formed based on these results. Without being bound to any particular theory, the advantage of large and nonpolar residues suggests that glucose growth attenuation is due to steric exclusion. The larger side chains may physically restrict the size of the pore, allowing the smaller xylose molecule to bind and traverse more efficiently than larger hexoses. A similar hypothesis has been proposed to explain an observed correlation between amino acid size and transporter function for glucose (43). This hypothesis is supported by the crystal structure of a related MFS transporter, *E. coli* xylE (41). Based on the structure, *E. coli* xylE Phe$^{24}$, an analogous residue to C. intermedia gxs1 Phe$^{40}$, appears to interact with sugars as they pass through the pore. E. coli xylE is too dissimilar from yeast MFS transporters to enable structure prediction, yet this evidence suggests that this residue appears to play a role in all MFS sugar transporters.

Transporters from Neurospora crassa and S. stipitis were found to be exclusive for xylose in uptake assays (35), but are unable to support robust growth of recombinant S. cerevisiae on xylose. The Escherichia coli xylE transporter is xylose specific when expressed in its native host (44), but is inhibited by glucose and remains non-functional in S. cerevisiae despite attempts at directed evolution. Prior to this work, no evidence has demonstrated a defined transporter engineering approach that is able to effectively eliminate glucose transport while amplifying xylose transport and supporting robust xylose growth. The mutants generated in this study demonstrate this desirable phenotype and provide evidence that the G-G/F-XXXG motif controls transport phenotype in a large number of MFS transport proteins.

Figure 5:
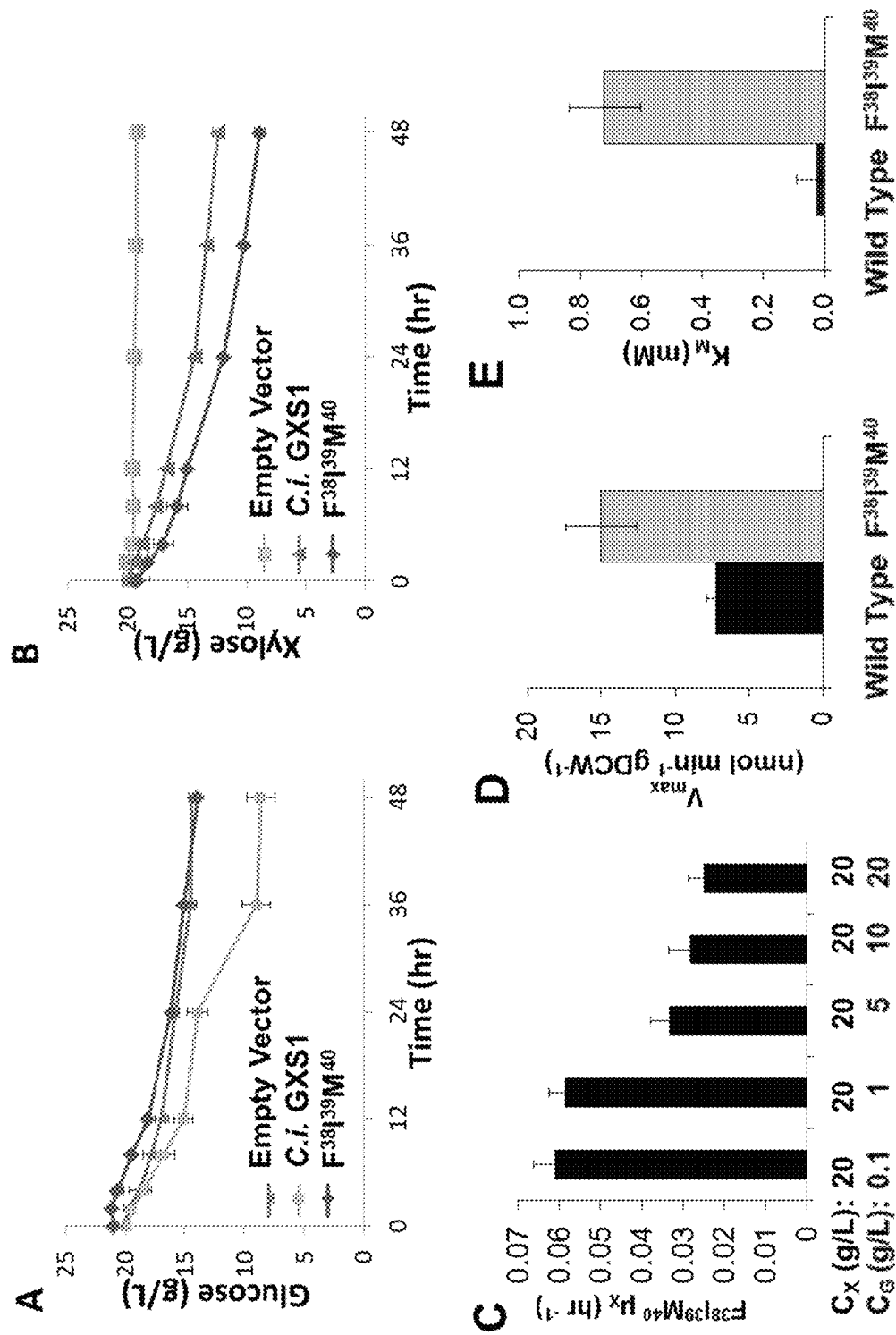
FIG. 5—Further characterization of C. intermedia gxs1 $Phe^{38}$ $Ile^{39}$ $Met^{40}$ triple mutant. A) Glucose uptake at high cell density for S. cerevisiae EX.12 expressing wild type, $Phe^{38}$ $Ile^{39}$ $Met^{40}$, and empty vector. B) Xylose uptake at high cell density for S. cerevisiae EX.12 expressing wild type, $Phe^{38}$ $Ile^{39}$ $Met^{40}$, and empty vector. C) Inhibition of growth rate on xylose with increasing glucose concentration. D) $V_{max}$ of both the wild type and the mutant. E) $K_M$ of both the wild type and triple mutant. Error is based on standard deviation of biological replicates.

It is also important to note that altering this motif in C. intermedia GXS 1 not only had an impact on glucose uptake, but also had an impact on the kinetics of xylose uptake. Specifically, the $K_m$ for xylose was significantly increased compared to wild type, indicating that exclusion of glucose was obtained at the expense of reduced affinity for xylose. Nevertheless, the affinity for xylose remains sufficiently high for nearly all fermentation conditions ($K_M$=0.721±0.116 mM, or approximately 0.1 g/L), and was partially compensated by a doubling in $V_{max}$ (FIG. 5). This result suggests a complex set of interactions between the transporter and sugar substrate, and is similar to other mutants of C. intermedia GXS1 (38).

Figure 13:
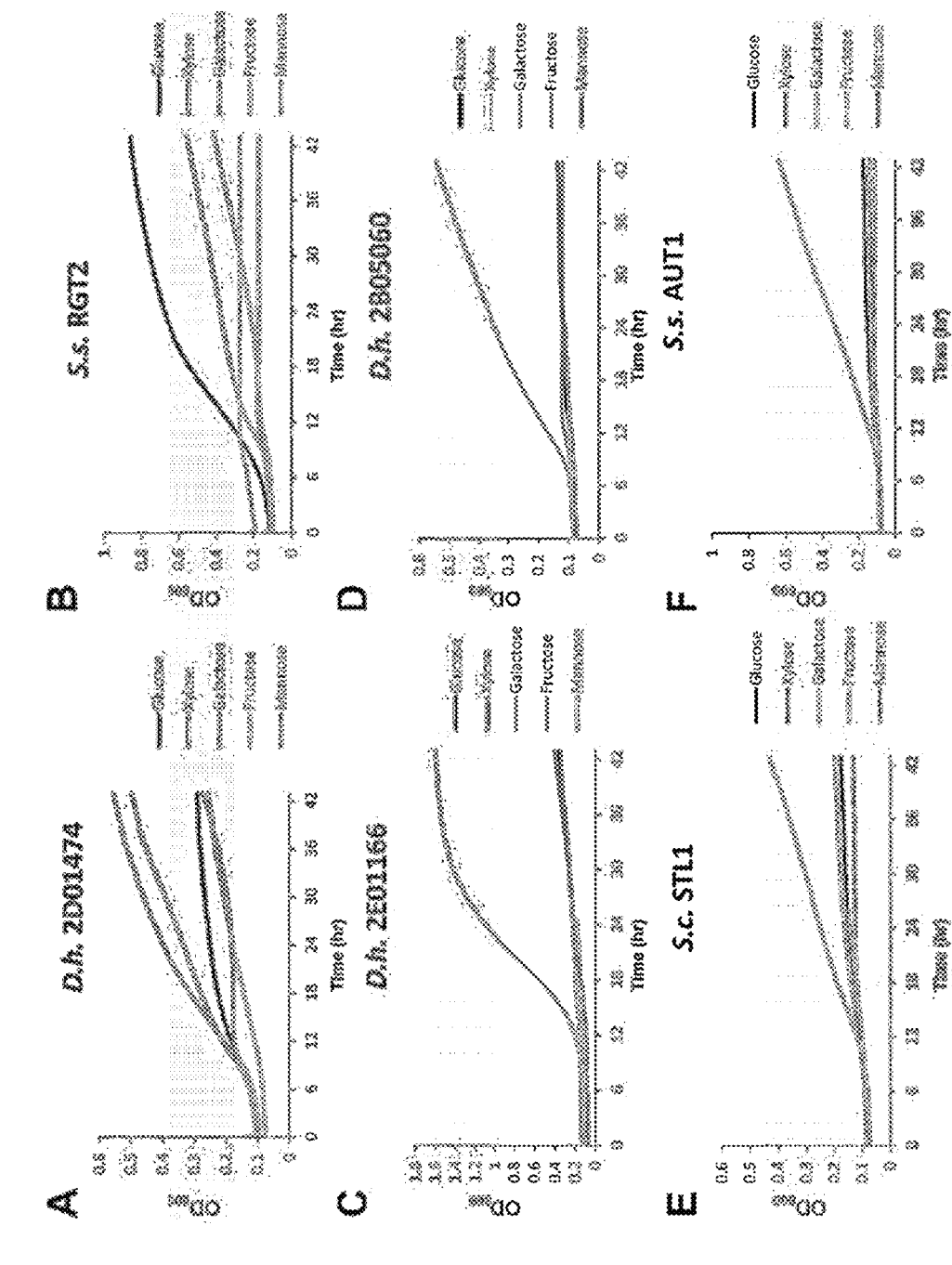
FIG. 13—Relatedness based on G-G/F-XXXG motif and growth rate data. Phylogram constructed in TreeView of a ClustalW multiple sequence alignment of the G-G/F-XXG motif of each transporter. To the right of the phylogram is plotted the exponential growth rate of S. cerevisiae EX.12 conferred by transporter expression. Two lines are placed across the chart to mark the upper limit of no growth for glucose and xylose. Arranging the transporters in this fashion remarkably clusters conferred phenotype better than basing the alignment on the whole amino acid sequence. This is further evidence of the influence the G-G/F-XXG motif has over monosaccharide uptake.
Figure 14:
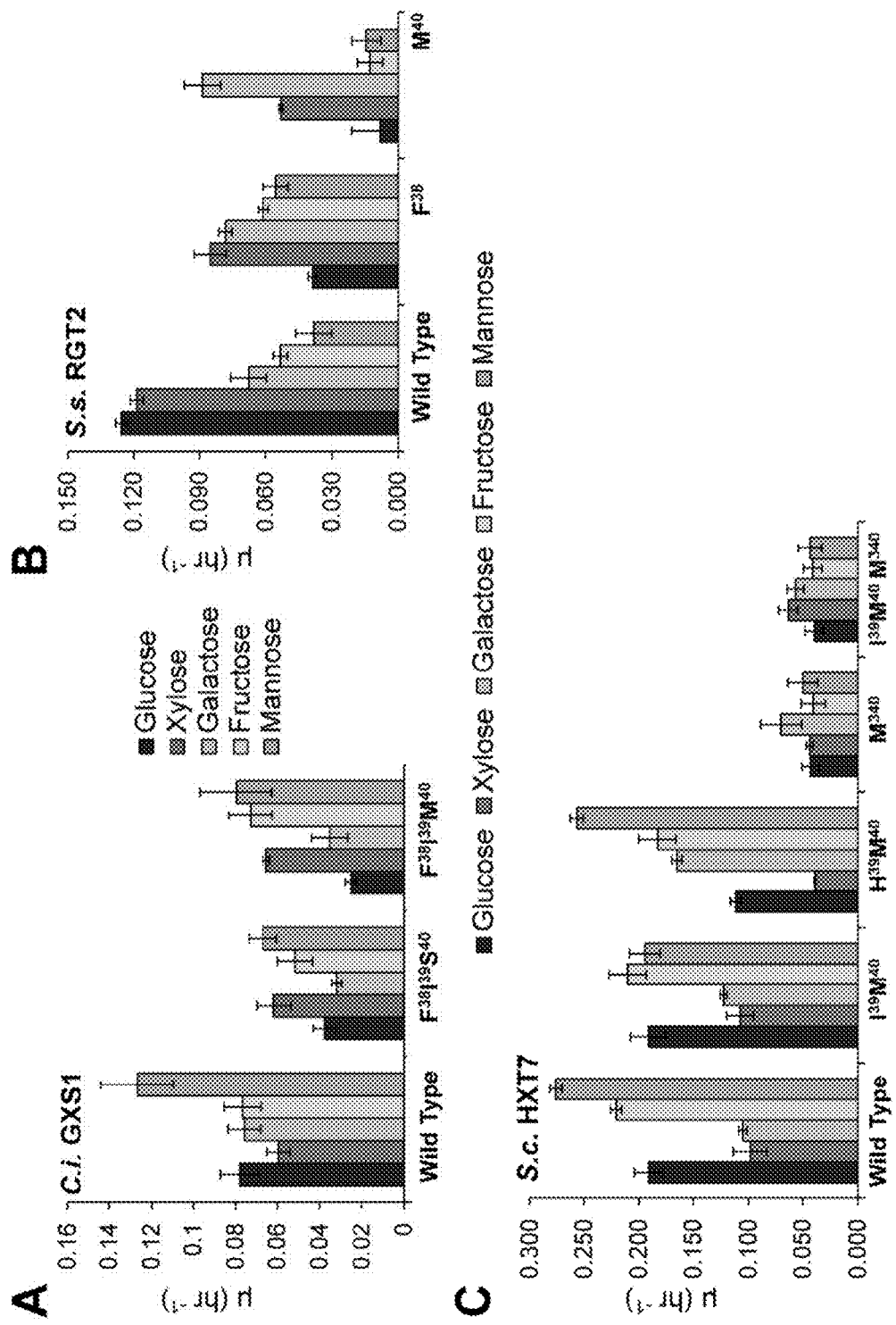
FIG. 14—Carbon source profile comparison. A) C. i. GXS1 and mutants. B) S. s. RGT2 and mutants. C) S.c. HXT7 and mutants. Note that these values are maximum exponential growth rates, and therefore may produce different comparisons than the late-stage linear exponential portions of the growth curves.

In the course of identifying and validating this motif, several novel native and heterologous transporters were identified and shown to possess previously unreported phenotypes (FIG. 13). The transporter D. hansenii 2D01474 can natively support growth on xylose compared with glucose. The transporter S. stipitis RGT2 confers the fastest growth rate on xylose over any ORF cloned from S. stipitis. Both of these transporters are closely related to C. intermedia GXS1 (FIG. 12) and may present a new class of related transporters that make excellent starting scaffolds for engineering exclusive xylose uptake. Of the remaining novel ORFs studied here, one group (D. hansenii 2E01166, D. hansenii 2B05060, S. cerevisiae STL1, and S. stipitis AUT1) confer higher exponential growth rates on galactose than any other sugar tested. This hexose transport profile is indicative of the potential for L-arabinose transport, since the galactose transporter S. cerevisiae GAL2 is one of the few transporters able to facilitate L-arabinose (45). This correlation is likely due to the similar stereochemistry between L-arabinose and galactose.

Figure 15:
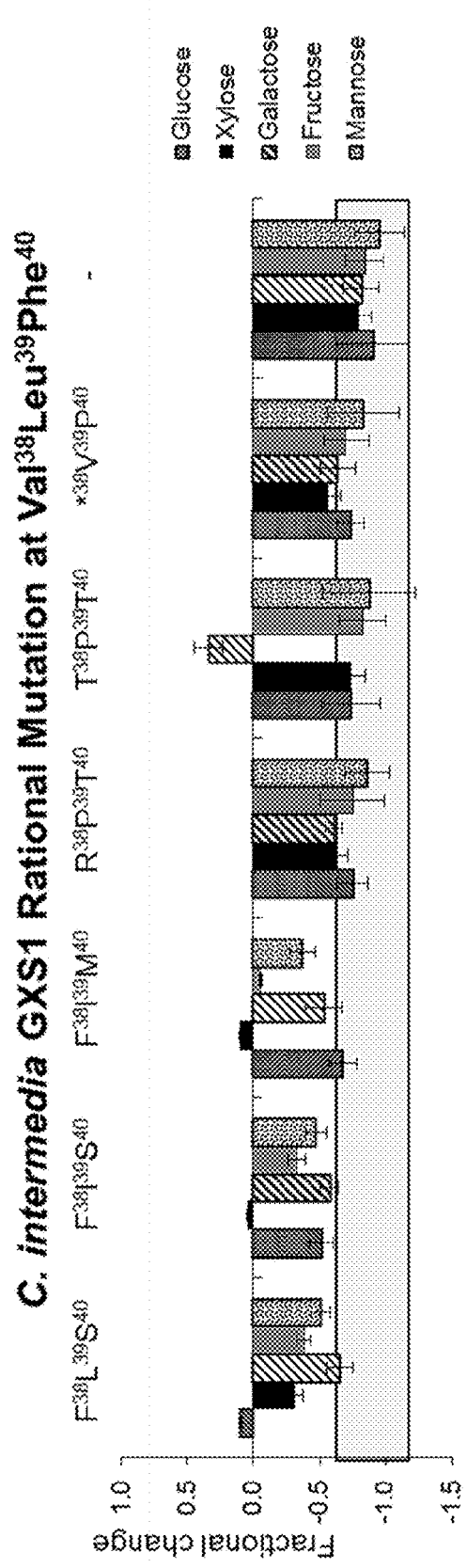
FIG. 15—Growth characterization of C. intermedia gxs1 rationally designed triple mutants. Fractional change from wild type is calcualted on a variety of carbon sources for five mutants with differing transporter motif sequences (e.g. FLS, FIS, FIM, RPT, TPT, *VP which contains a stop codon in the motif) compared to the negative control with no transporter motif sequence. The $T^{38}P^{39}T^{40}$ mutant shows a distinct preference toward galactose and away from the other sugars tested.
Figure 16:
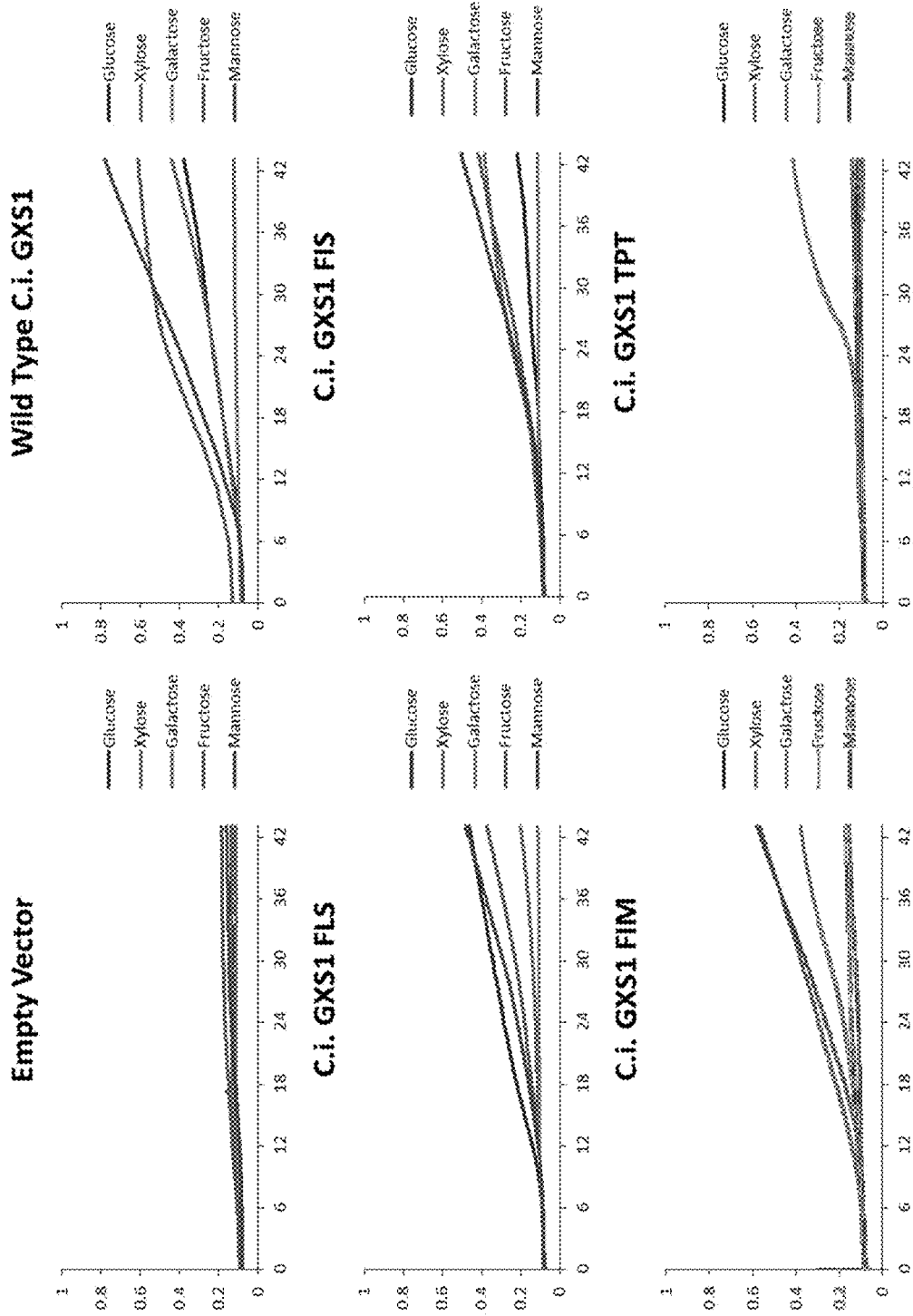
FIG. 16—Growth curves of rational gxs 1 mutants by mutation. Growth curves are presented for the mutants described in FIG. 15 on glucose, xylose, galactose, fructose, and mannose. Data is presented in graphs separated by mutant.
Figure 17:
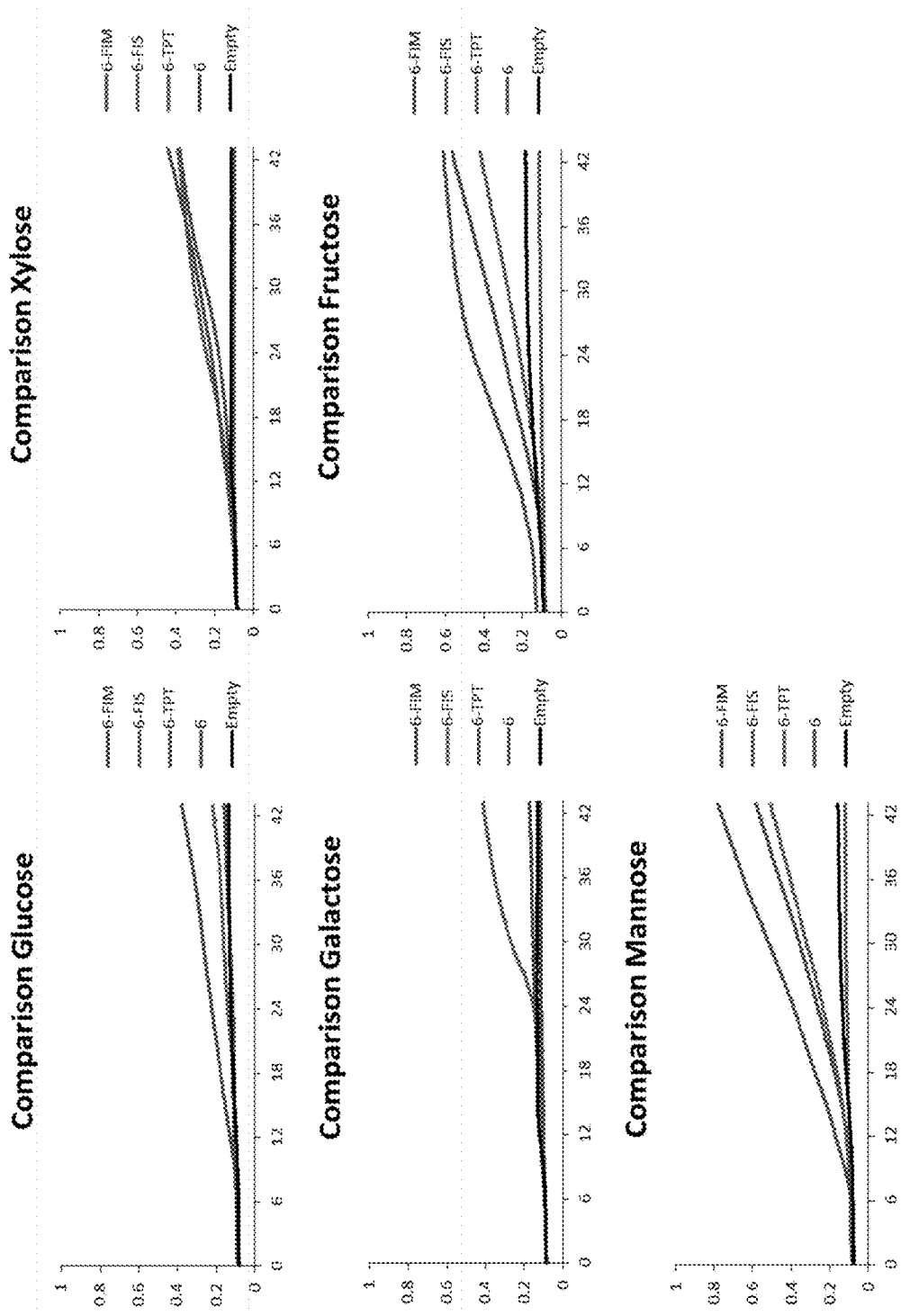
FIG. 17—Growth curves of rational gxs 1 mutants by mutation. Growth curves are presented for the mutants described in FIG. 15 on glucose, xylose, galactose, fructose, and mannose. Data is presented in graphs separated by carbon source.
Figure 18:
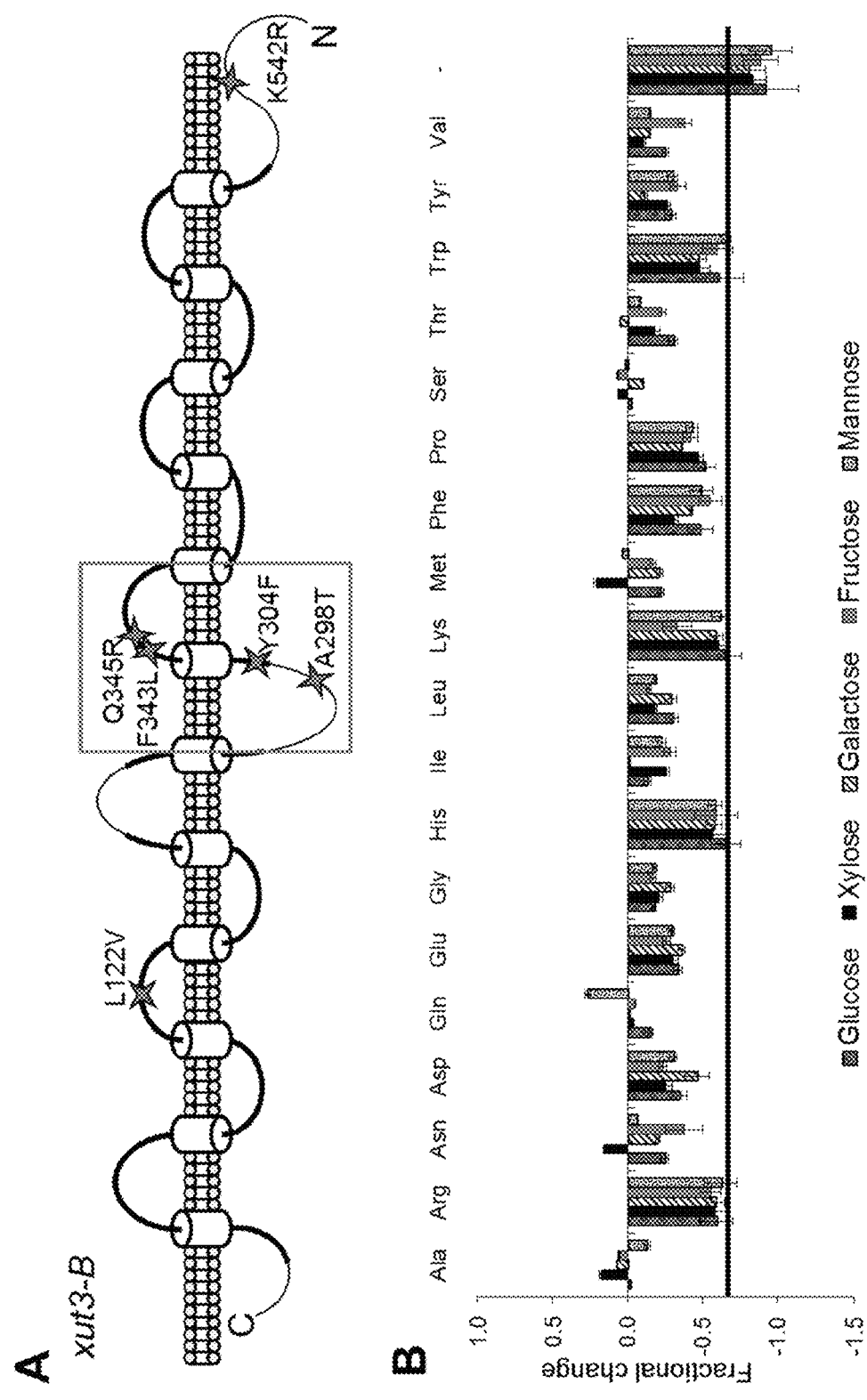
FIG. 18—Rewiring xut3 transporter proteins through the equivalent of the 297 residue from C. intermedia GXS1. A) Identification of previously identified mutations in the xut3 mutant transporter. B) Saturation mutagenesis was performed on the equivalent of the 297 residue from C. intermedia GXS1. Fractional change on growth of various carbon sources was measured and the results illustrated that this residue can control sugar transporter preference.

As discovered herein, substitution at the -XXX- positions of the transporter motif sequence uncovered several interesting phenotypes. Indeed, substitution with Thr and Pro (e.g. a transporter motif sequence of -G-G-T$^{38}$P$^{39}$T$^{40}$G-) results in selective galactose uptake in the modified transporter protein. Such exclusive uptake, as discussed herein, is also indicative of L-arabinose uptake ability (FIGS. 15 & 16). Thus, the work described herein shows transporter proteins can successfully be engineered into galactose and arabinose transporters.

This work describes a conserved G-G/F-XXXG motif and an engineering approach to modify this motif. This motif allowed for the rewiring of several transporters and yielded the mutant transporters C. intermedia gxs1 Phe$^{38}$ Ile$^{39}$ Met$^{40}$, S. stipitis rgt2 Phe$^{38}$ and Met$^{40}$, and S. cerevisiae hxt7 Ile$^{39}$Met$^{40}$Met$^{340}$ that do not transport glucose yet support S. cerevisiae EX.12 growth on xylose. This motif also yielded C. intermedia Thr$^{28}$Pro$^{39}$Thr$^{40}$ that supports S. cerevisiae EX.12 growth on galactose, and no other sugar tested. These major facilitator superfamily transporters are channels and thus a substrate molecule interacts with many residues during transport. Yet, no other residues discovered to date display the degree to which glucose transport can be attenuated and xylose transport amplified than the residues in the G-G/F-XXXG motif. Thus, this study provides further insight into the residues responsible for monosaccharide transport in MFS proteins while establishing a platform for engineering a specific, efficient xylose transporter.

Materials and Methods

Strains, media, and plasmids—Molecular cloning and standard culturing techniques with E. coli DH10B were performed according to Sambrook (46). S. cerevisiae EX.12 was used for all yeast experiments and was constructed as previously described (38). All transporters were cloned into p414-TEF, a standard yeast shuttle vector created by Mumberg (47). Yeast synthetic complete media was used for culture and experimental growth media. CSM-Trp was used when S. cerevisiae EX.12 was carrying a transporter. Carbon sources were provided at 20 g/L.

Transporter Cloning—Potential xylose transporters were identified from literature and BLAST search. To obtain this list of 46, we combined 26 transporters from our previous survey of transporters (36) along with 20 additional transporters identified through homology search using C. intermedia GXS1 and S. cerevisiae STL1 as a template. Details on cloning and transporter libraries are described herein. Primers are listed in Table 4 (cloning), Table 5 (saturation mutagenesis), and Table 6 (point mutations).

TABLE 4 primers used for cloning putative transporters.

| Name | Target ORF | Orientation | $T_m$ | R. Enz. | Sequence | SEQ ID NO: |
|---|---|---|---|---|---|---|
| EY194 | ScHXT3 | F | 55 | XmaI | TATTCCCCCGGGatgaattcaact ccagatttaatatctcc | 2 |
| EY208 | ScHXT3 | R | 64 | ClaI | CGGTATCCATCGATttatttCttg ccgaacattttctt | 3 |
| EY265 | HXT1 | F | 64 | XmaI | TATTCCCCCGGGatgaattcaact cccgatctaatatc | 4 |
| EY266 | HXT1 | R | 64 | ClaI | CGGTATCCATCGATttatttcctg ctaaacaaactcttg | 5 |

TABLE 4-continued primers used for cloning putative transporters.

| Name | Target ORF | Orientation | $T_m$ | R. Enz. | Sequence | SEQ ID NO: |
|---|---|---|---|---|---|---|
| EY554 | SsHGT2 | F | 60 | SpeI | GGACTAGTatgagctacgaagataaactcg | 6 |
| EY555 | SsHGT2 | R | 60 | SalI | TATTCCGTCGACttaaggcttttcctcagaactt | 7 |
| EY558 | Dh2C02530 | F | 60 | SpeI | GGACTAGTatgggttacgaagataaattagtg | 8 |
| EY559 | Dh2C02530 | R | 60 | SalI | TATTCCGTCGACttaagtcatgtgagaagtatcgc | 9 |
| EY560 | Dh2E01166 | F | 61 | SpeI | GGACTAGTatgggatatgaagaaaagttgg | 10 |
| EY561 | Dh2E01166 | R | 59 | SalI | TATTCCGTCGACtcaagcaatgtgatctgc | 11 |
| EY562 | Dh2E01298 | F | 61 | SpeI | GGACTAGTatgggatacgaagataaattactagg | 12 |
| EY563 | Dh2E01298 | R | 60 | SalI | TATTCCGTCGACctaagcaatatggacagcactag | 13 |
| EY564 | ScMAL11 | F | 60 | SpeI | GGACTAGTatgaaaaatatcatttcattggtaag | 14 |
| EY565 | ScMAL11 | R | 60 | SalI | TATTCCGTCGACttaacatttatcagctgcatttaat | 15 |
| EY566 | ScSTL1 | F | 60 | SpeI | GGACTAGTatgaaggatttaaaattatcgaatttt | 16 |
| EY567 | ScSTL1 | R | 60 | SalI | TATTCCGTCGACtcaaccctcaaaatttgct | 17 |
| EY568 | SsRGT2 | F | 60 | SpeI | GGACTAGTatgggtttagaagacagtgct | 18 |
| EY569 | SsRGT2 | R | 61 | SalI | TATTCCGTCGACctatacagaagcttcttcaacttcag | 19 |
| EY572 | SsAUT1 | F | 61 | XmaI | TATTCCCCCGGGatgagtgctgacgaaaaagtc | 20 |
| EY573 | SsAUT1 | R | 61 | XhoI | TATTCCCTCGAGctactcgacataagagacttctgg | 21 |
| EY574 | HXT8 | F | 61 | XmaI | TATTCCCCCGGGatgactgatcgtaaaaccaactt | 22 |
| EY575 | HXT8 | R | 61 | XhoI | TATTCCCTCGAGctaaaacattcttttgtagaagggtt | 23 |
| EY576 | HXT2 | F | 62 | XmaI | TATTCCCCCGGGatgtctgaattcgctactagcc | 24 |
| EY577 | HXT2 | R | 63 | XhoI | TATTCCCTCGAGttattcctcggaaactcttttttc | 25 |
| EY578 | HXT9 | F | 62 | XmaI | TATTCCCCCGGGatgtccggtgttaataatacatcc | 26 |
| EY579 | HXT9 | R | 62 | XhoI | TATTCCCTCGAGttagctggaaaagaacctcttg | 27 |
| EY580 | HXT10 | F | 60 | XmaI | TATTCCCCCGGGatggttagttcaagtgtttcca | 28 |
| EY581 | HXT10 | R | 60 | XhoI | TATTCCCTCGAGttatttactatcaacaataactaatggtgtac | 29 |
| EY582 | HXT14 | F | 61 | XmaI | TATTCCCCCGGGatgactgctcagattccgtat | 30 |

TABLE 4-continued primers used for cloning putative transporters.

| Name | Target ORF | Orientation | $T_m$ | R. Enz. | Sequence | SEQ ID NO: |
|---|---|---|---|---|---|---|
| EY583 | HXT14 | R | 61 | XhoI | TATTCCCTCGAGctactccggttcaaatattttattg | 31 |
| EY644 | SsSTL1 | F | 61 | SpeI | GGACTAGTatggcatatcttgattggttaac | 32 |
| EY645 | SsSTL1 | R | 62 | XmaI | TATTCCCCCGGGctaggctgctttaggttttctg | 33 |
| EY646 | DhE01386 | F | 61 | SpeI | GGACTAGTatgtataaaatatggtcaaaaactaacact | 34 |
| EY647 | DhE01386 | R | 61 | XmaI | TATTCCCCCGGGttaaacttccgcaggcttaa | 35 |
| EY648 | DhB05060 | F | 63 | SpeI | GGACTAGTatggctttaaaaatcttttctagaacc | 36 |
| EY649 | DhB05060 | R | 63 | XmaI | TATTCCCCCGGGttaagcattaggagttaagataccttctg | 37 |
| EY650 | Y10D00132 | F | 63 | SpeI | GGACTAGTatggttttttggacgagaaaaag | 38 |
| EY651 | Y10D00132 | R | 63 | XmaI | TATTCCCCCGGGttaaacgaactcggcagtgt | 39 |
| EY700 | DhA2D01474 | F | 55 | XmaI | TATTCCCCCGGGatgggtttagaagataatgc | 40 |
| EY701 | DhA2D01474 | R | 56 | XhoI | TATTCCCTCGAGttagactgaagtggtttcaat | 41 |

TABLE 5 primers used for saturation mutagenesis of C. intermedia GXS1.

| Name | Target A.A. | Orientation | $T_m$ | Kit Used | Sequence | SEQ ID NO: |
|---|---|---|---|---|---|---|
| EY630 | GXS1Sat40 | F | 79 | Sat Multi | tttgctgcttctggtggtgtccttNNKggatacgatactggtacta | 42 |
| EY675 | GXS1 39LSat | F | 79 | Sat Multi | tttgctgcttctggtggtgtcnnkttcggatacgatactggtact | 43 |
| EY676 | GXS1 38VSat | R | 79 | Sat Multi | gtcttttttgctgcttctggtggtnnkcttttcggatacgatactggtac | 44 |
| EY711 | GXS1 38Sat | F | 79 | Sat Multi | gtcttttttgctgcttctggtggtyrkcttttcggatacgatactggtac | 45 |
| EY712 | GXS1 39LSat | F | 79 | Sat Multi | tttgctgcttctggtggtgtcvvgttcggatacgatactggtact | 46 |
| EY723 | GXS139DDK | F | 78 | Sat Multi | tttgctgcttctggtggtgtcDDKttcggatacgatactggtact | 47 |
| EY727 | GXS1 38Y | F | 78 | Quik | gctgcttctggtggttatcttttcggatacgatac | 48 |
| EY728 | GXS1 38Y | R | 78 | Quik | gtatcgtatccgaaaagataaccaccagaagcagc | 49 |
| EY729 | GXS1 38C | F | 78 | Quik | gctgcttctggtggttgtcttttcggatacgatac | 50 |

TABLE 5-continued primers used for saturation mutagenesis of *C. intermedia* GXS1.

| Name | Target A.A. | Orientation | $T_m$ | Kit Used | Sequence | SEQ ID NO.: |
|---|---|---|---|---|---|---|
| EY730 | GXS1 38C | R | 78 | Quik | gtatcgtatccgaaaagacaac caccagaagcagc | 51 |
| EY731 | GXS1 38H | F | 78 | Quik | gctgcttctggtggtcatcttt tcggatacgatac | 52 |
| EY732 | GXS1 38H | R | 78 | Quik | gctgcttctggtggtcatcttt tcggatacgatac | 53 |
| EY733 | GXS1 39H | F | 78 | Quik | tgcttctggtggtgtccatttc ggatacgatactg | 54 |
| EY734 | GXS1 39H | R | 78 | Quik | cagtatcgtatccgaaatggac accaccagaagca | 55 |
| EY735 | GXS1 39M | F | 78 | Quik | gctgcttctggtggtgtcatgt tcggatacgatactggt | 56 |
| EY736 | GXS1 39M | R | 78 | Quik | accagtatcgtatccgaacatg acaccaccagaagcagc | 57 |

TABLE 6

Primers used for point mutations.

| Name | Target A.A. | Orientation | $T_m$ | Sequence | SEQ ID NO.: |
|---|---|---|---|---|---|
| EY702 | SsRGT2-F40M | F | 78 | cagccttcggtggtatccttatgggttatga cactggt | 58 |
| EY703 | SsRGT2-F40M | R | 78 | accagtgtcataacccataaggataccaccg aaggctg | 59 |
| EY737 | GXS1 FLS | F | 78 | tttttgctgcttctggtggtttcctttctgg atacg | 60 |
| EY738 | GXS1 FLS | R | 78 | cgtatccagaaaggaaaccaccagaagcagc aaaaa | 61 |
| EY739 | GXS1 FIS | F | 78 | ttttgctgcttctggtggttttcatttctgga tacgatactgg | 62 |
| EY740 | GXS1 FIS | R | 78 | ccagtatcgtatccagaaatgaaaccaccag aagcagcaaaa | 63 |
| EY741 | GXS1 FIM | F | 78 | ttttgctgcttctggtggtttcattatggga tacgatactgg | 64 |
| EY742 | GXS1 FIM | R | 78 | ccagtatcgtatcccataatgaaaccaccag aagcagcaaaa | 65 |
| EY747 | ScHXT7M340 | F | 78 | ctatgattcaatctctacaacaattgacagg tatgaactatttcttctactatggtactact atttt | 66 |
| EY748 | ScHXT7M340 | R | 78 | aaaatagtagtaccatagtagaagaaatagt tcatacctgtcaattgttgtagagattgaat catag | 67 |
| EY749 | ScHXT7FHM | F | 78 | catgatcgcctttggtggtttccatatgggt tgggatactggtaccattt | 68 |
| EY750 | ScHXT7FHM | R | 78 | aaatggtaccagtatcccaacccatatggaa accaccaaaggcgatcatg | 69 |
| EY753 | ScHXT10 63M | F | 78 | ctgatgattgcctttggtggattcattatgg gttgggatacagg | 70 |
| EY754 | ScHXT10 63M | R | 78 | cctgtatcccaacccataatgaatccaccaa aggcaatcatcag | 71 |

TABLE 6-continued

Primers used for point mutations.

| Name | Target A.A. | Orientation | $T_m$ | Sequence | SEQ ID NO.: |
|------|-------------|-------------|-------|----------|-------------|
| EY760 | SsRGT2-38F | F | 78 | gttcgcagccttcggtggtttccttttcggtta | 72 |
| EY761 | SsRGT2-38F | R | 78 | taaccgaaaaggaaaccaccgaaggctgcgaac | 73 |
| EY766 | ScHXT7-FIM | F | 78 | catgatcgcctttggtggtttcattatgggttgggatactggtaccattt | 74 |
| EY767 | ScHXT7-FIM | R | 78 | aaatggtaccagtatcccaacccataatgaaaccaccaaaggcgatcatg | 75 |

Growth rate measurements—All exponential growth rates were measured and calculated according to the method previously described using a Bioscreen C (Growth Curves USA, Piscataway, N.J.) and a MATLAB script (36, 38).

Fractional change—Fractional change in growth rate from wild type was calculated by taking the difference between the growth rates of the mutant and wild type over the growth rate of the wild type for each individual carbon source. Error was propagated using the least squares method based on the standard deviation in exponential growth rates of the mutant and the wild type.

High cell density fermentation—High cell density experiments were conducted as previously described (38). Yeast cultures were suspended at OD in 20 g/L glucose, 10 g/L glucose and 10 g/L xylose, or 20 g/L xylose. Supernatant concentration of xylose and/or glucose was measured using a YSI Life Sciences Bioanalyzer 7100MBS.

Radiolabeled xylose uptake—Uptake of $^{14}C$ labeled xylose was used to determine the Michaelis-Menten parameters for C. intermedia GXS1 and the Phe$^{38}$ Ile$^{39}$ Met$^{40}$ triple mutant. The method was performed as previously described (38).

Growth rate measurements—All exponential growth rates were measured and calculated according to the method previously described using a Bioscreen C (Growth Curves USA, Piscataway, N.J.) and a MATLAB script. The Bioscreen C measures online optical density for easy and accurate measurement of the growth curves of up to 200 strains at one time. Error was calculated based on biological triplicate in all cases. In all cases, the Bioscreen C was set to maintain a temperature of 30° C., employ high continuous shaking, and to measure optical density every 10 minutes. A single carbon source per well was used in all experiments save one. Growth on xylose in the presence of increasing concentrations of glucose was measured for C. intermedia gxs1 Phe38 Ile39 Met40.

It is important to note that the environment of the Bioscreen C does not support cultures reaching high optical density and observed values are below $OD_{600}$ of 2. This does not reflect the optical densities reached in flasks, which typically approach $OD_{600}$ of 10.

Transporter Cloning—Each of these transporters was functionally analyzed for conferred growth rate on xylose and glucose in S. c. EX.12. Genomic DNA and PCR were performed as previously described (36). Using this approach, open reading frames from Scheffersomyces stipits, Debaryomyces hansenii, Yarrowia lipolytica, and Saccharomyces cerevisiae were cloned using primers listed in Table 4. Mutant transporters and saturation library construction is described below and Primers are listed in Table 5 (saturation) and Table 6 (point).

Saturation mutagenesis and point mutation—The Stratagene Multi mutagenesis kit was used to generate saturation mutagenesis libraries at positions 38, 39, and 40 in C.i. GXS1. Each codon was replaced with the degenerate NNK sequence recommended for use when creating saturation mutagenesis libraries. It is important to note that the wild type codon was represented in the NNK library for both Val38 and Leu39 thus alternative 3 primers that did not contain the wild type sequence were designed. This subsequently necessitated the design of specific point mutation primers to access certain residues and the use of the Stratagene Quikchange kit. Some single point mutation primers were ordered to complete the saturation libraries. The Stratagene Quikchange mutagenesis kit was used to generate all rational single, double, and triple mutants. Primers are listed in Table 5 (saturation) and Table 6 (point).

Example 2

Sequence alignment of 54 sequences from major facilitator superfamily sugar transporter proteins. The transporter motif sequence is shown as bolded residues and corresponds as described herein to residue positions 36-41 of C. intermedia GXS1 protein.

```
Dh2C02530p    KFRNFLDKTPNIYNVFVIASISCISGLMFGIDISSMSLFIGDDKYIKYFHK---------   63

Dh2E01166p    KLRLFLDKLPNIYNIYVIATISCISGLMFGIDISSMSAFLSNDAYLKYFGT---------   63

Dh2E01298p    KFRNFLDKFPNIHNVYIVVGISCISGMMFGIDISSMSLFIGDDKYLDYFNS---------   63

SsHGT2        KFRTFLDRLPNIYNVYIIASISCISGMMFGFDISMSAFIGEDDYKNFFNN---------   63

Dh2A14300p    SLNKELDKFHTTYNIYVIAMITTISGMMFGFDVSSISAFISEPSYRRFFNY---------   61
```

```
Y10B06391p    QVGALQHRFPKLHNPYLTAAVATMGGLLFGFDISSVSAFVDTKPYKEYFGY---------    59
Y10B01342p    --------MYKVHNPYLTAAVATMGGMLFGFDISSVSAFVGEDNYMNYFGH---------    43
BmHGT2        --------MGRITNPYVLTALACTGGLLFGFDISSMSAIISSPNYLTYFGPKDLTVECPD    52
At5g59250     LASDAPESFSWSSVILPFIFP-ALGGLLFGYDIGATSGATLSLQSP----ALSGTTWFNF   139
At5g17010     ---HVPENYSVVAAILPFLFP-ALGGLLYGYEIGATSCATISLQEPMTLLSYYAVPFSAV    89
SsAUT1        LNAEATNKWHIPPRLIGVIALGSMAAAVQGMDESVINGANLFYPKAFGVD----TMHNSD   161
Y10D00132     LNREITNKWDHPMKVYYLVVCCSLAAAVQGMDETVINGANIIFPAQFGIKEDSGVVSRKS   180
BmSTIL1       -----FLGMRGIKLNWAIGFAASAGFLLFGYDQGVLGSLYTLPSWNAQFPEINTAAVGDS    73
SsXUT6        AKTNSYLGLRDHKLNFAVSCFAGVGFLLFGYDQGVMGSLLTLPSFENTFPAMP-------    75
Dh2E01386p    --KTNTMGLRGKPLRVAITICCTIGFSLFGYDQGLMSGIITGKQFNEEFPPTHGT-----    59
Dh2B05060p    --RTNTMGLRGKRLRVMFIVVATLGFSLFGYDQGLMSGLITGEQFNAEFPPTAGK-----    60
SsSTL1        --RTNTFGLRGKKLRAFITVVAVTGFSLFGYDQGLMSGIITADQFNSEFPATR-------    60
ScSTL1        --RTSHWGLTGKKLRYFITIASMTGFSLFGYDQGLMASLITGKQFNYEFPATKENG---D    70
BmHXT10       ----IDVGLRGNWLLTVITASCAAGFLLVGYDNGVMGGVVGLGEFNKTFNNPD-------    66
SsXUT2        ----------GKQVSYAVTFTCELAFILFGIEQGIIGNLINNQDFLNTFGNPTG------    53
CnBC3990p     --HKTQRRLVGHNLLYSVSVFSLIGVWLFGYDQGFMSGIITGPYFKAYFNQPTS------    62
Y10F06776p    -----MFSLTGKPLLYFTSVFVSLGVFLFGYDQGVMSGIITGFYFKEYFHEPTR------    49
BmXUT3        VGATGAKGLIKNARTFAIAVFASMGGLIYGYNQGMFGQILSMHSFQEASGVKGIT-----    78
SsXUT1        AGKSGVAGLVANSRSFFIAVFASLGGLVYGYNQGMFGQISGMYSFSKAIGVEKIQD----    77
SsXUT3        AHGNVVTIMMKDPVVFLVILFASLGGLLFGYDQGVISGIVTMESF--GAKPFRTFM----    63
SsXUT3-A      AHGNVVTIMMKDPVVFLVILFASLGGLLFGYDQGVISGIVTMESF--GAKPFRTFM----    63
SsXUT3-B      AHGNVVTIMMKDPVVFLVILFASLGGLLFGYDQGVISGIVTMESF--GAKPFRTFM----    63
DhXylHP       SKGNIITVMSKDPLVFCIIAFASIGGLLFGYDQGVISGIVTMESF--AAKPFRIFS----    64
ScGAL2        PIEIPKKPMSEYVTVSLLCLCVAFGGFMFGWDTGTISGFVVQTDFLRRFG-MKHKDGT--   113
ScHXT8        EVVVPEKPASAYATVSIMCLCMAFGGFMSGWDTGTISGFVNQTDFLRRFGNYSHSKNY--   109
ScHXT1        AVAPPNTGKGVYVTVSICCVMVAFGGFIFGWDTGTISDGVAQTDFLRRFG-MKHHDGS--   107
ScHX73        VLTNPNTGKGAYVTVSICCVMVAFGGFVFGWDTGTISGFVAQTDFLRRFG-MKHKDGS--   104
ScHXT7        VVEIPKRPASAYVTVSIMCIMIAFGGFVFGWDTGTISGFINQTDFIRRFG-MKHKDGT--   107
ScHXT9        PIKLPQKPLSAYTTVAILCLMIAFGGFIFGWDTGTISGFVNLSDFIRRFG-QKNDKGT--   103
ScHXT2        NAELPAKPIAAYWTVICLCLMIAFGGFVFGWDTGTISGFVNQTDFKRRFG-QMKSDGT--    98
ScHXT10       SLDIPYKPIIAYWTVMGLCLMIAFGGFIFGWDTGTISGFINQTDFKRRFG-ELQRDGS--    91
CiGXF1        QVDAPQKGFKDYIVISIFCFMVAFGGFVFGFDTFTISGFVNMSDFKDRFG-QHHADGT--    86
ScHXT13       NVEPPKRGLIGYLVIYLLCYPISFGGFLPGWDSGITAGFINMDNFKMNFGSYKHSTGE--   100
BmGXF1        -MVFQVRGTPIGALTLFIAMLASMGGFLFGWDTGQISGLTQMADFRQRFATVDNPDAIG-    58
ScHXT14       GQAAKISHNASLHIPVLLCLVISLGGFIFGWDIGTIGGMTNMVSFQEKFGTTNIIHDDET   105
BmGXS1        GPVARPASVKQSLPAILVAAASFGGVLFGYDTGTISGLIVMPNFQETFGKPVPGSTTGA    74
BmRGT2        GPVARPASVKQSLPAILVAAASFGGVLFGYDTGTISGLIVMPNFQETFGKPVPGSTTGA    74
Ci2XS1        FVNVGEKKAGSTAMAIIVGLFAASGGVLFGYDTGTISGVMTMDYVLARY------PSNK-    64
CiGXS1-A      FVNVGEKKAGSTAMAIIVGLFAASGGVLVGYDTGTISGVMTMDYVLARY------PSNK-    64
CiGXS1-B      FVNVGEKKAGSTAMAIIVGLFAASFGGVLSGYDTGTISGVMTMDYVLARY------PSNK-   64
Dh2D01474     YVNVGEKRAGSASMGIFVGAFAAFGGVLFGYDTGTISGIMAMNYVKGEF------PANK-    64
```

-continued

```
Dh0D02167p    YVNVGEKRAGSASMGIFVGAFAAFGGVLFGYDTGTISGIMAMNYVKGEF------PANK-     64
SsRGT2        YINFGEKKAGSTTMGICVGLFAAFGGILFGYDTGTISGIMAMDYVTARG------PSNH-     64
Y10C06424p    IINRGEKPEGSAFMAAFVAVFVAFGGILFGYDTGTISGVMAMPFVKKTG------TDDG-     58
Y10C08943p    -------------MAIIVAVFVAFGGLLYGYDTGTIAGIMTMGYVKEHF------TDFGK     41
Dh2B14278p    YYKKMQQKS-SSSSAITVGLVAAVGGFLYGYDTGLINDIMEMTYVKDNF------PANG-     69
EcXylE        -----MNTQYNSSYIFSITLVATLGGLLFGYDTAVISGTVESLHTVFVAPQNLSESAAN-     54
SsXUT5        RSIGPLIPRNKHLFYGSVLLMSIVHPTIMGYDSMMVGSILNLDAYVNYFH----------     53
ScMAL11       KSMTLKQALLKYPKAALWSILVSTTLVMEGYDTALLSALYALPVFQRKFGTLNGEGS---    148
```

Example 3

Sequence alignment of 57 sequences from major facilitator superfamily sugar transporter proteins. Bolded residues correspond to the alignment of conserved residue corresponding to 297 of *C. intermedia* GXS1 protein.

```
Dh2C02530p    WAQAWQQLTGMNTLMYYIVYVFQMAGYEG-DANLVASSIQYCLNTGMTIPALYFMDKLGR   340
Dh2E01166p    FAQIWQQLTGMNTLMYYIVYVFEMAGYHG-DANLVASSIQYCINFAMTIPALYLMDKVGR   340
Dh2E01298p    FAQIWQQLTGMNTLMYYIVYVFDMAGYQG-DANLIASSIQYVLFFVMTAPSLYLMDKLGR   340
SsHGT2        FAQIWQQLTGMNVMMYYIVYIFNMAGYSN-NANLVASSIQYVLNTAATVPALFLMDYIGR   340
Dh2A14300p    SAQIWNQLTGMNVMMYYIVYIFEMVGYTG-NTVLVSSSIQYVINFGVTLIALPLSDYVGR   336
Y10B06391p    WAQIWQQLTGMNVMMYYIVLIFTMAGYTG-NANLVASSIQYVINMIMTIPALLFIDRVGR   336
Y10B01342p    WAQIWQQLTGMNIMMYYVVIIFKMAGYSGKSAVIVSGSIQYIINVVMTIPALLFIDKIGR   320
BmHGT2        FTQIWSQLTGMNVMMYYLSYVFEMAGITG-NIALISNGIQYVINVVMTVPALLYVDRWGR   347
At5g59250     GLVLFQQITGQPSVLYYAGSILQTAGFSAAADATRVSVIIGVFKLLMTWVAVAKVDDLGR   424
At5g17010     GLVLFQQ-----------------------------------LIMTGVAVVIDRLGR   334
SsAUT1        FIVMFMQQFCGINVIAYYSSSIFVQSGFSQTSALIASWGFGMLNFTFAIPAFFTIDRFGR   441
Y10D00132     FIVMFMQQFCGINVIAYYSSSIFMESGFGAIQALLASFGFGAINFVFALPAVYTIDTFGR   459
BmSTL1        MSQMFQQISGINLITYYIGKTLQEQLGFSDINSRILAAANGTEYFIASWAAVFFIEKMGR   353
SsXUT6        WSQIMQQITGINIIITYYAGTIFESYIGMSPFMSRILAALNGTEYFLVSLIAFYTVERLGR   363
Dh2E01386p    STQFFQQFTGCNASIYYSTVLFENSIGLTGKLPLILGGVFATIYALSTIPSFFLIDRLGR   344
DH2B05060p    SGQFFQQFTGCNAAIYYSTVLFEDTIHLERRLALILGGVFATVYALSTIPSFFLVDTLGR   345
SsSTL1        STQFFQQFTGCNAAIYYSTVLFQDTIGLERRMALIIGGVFATVYAIFTIPSFFLVDTLGR   342
ScSTL1        STQFFQQFTGCNAAIYYSTVLFNKTIKLDYRLSMIIGGVFATIYALSTIGSFFLIEKLGR   356
BmHXT10       FIQAAQQLSGINALIYYSGTLFSQSIGLDSKKSALFAGGLNMCLILGSTISIFLIDRVGR   346
SsXUT2        MSMFAQQLSGVNVVNYYITFVLINSVGIEDNLALILGGVAVICFTVGSLVPTFFADRMGR   330
CnBC3990p     SSQLFAQLNGINVISYYAPLVFEQAG-WIGRDAILMTGINALFYVASSLPPWYLMDRAGR   334
Y10F06776p    SSQMFAQLNGINVISYYAPLVFEEAG-WVGRSAILMTGINGIVYVCSTIPPWYLVDKWGR   322
Dh2F19140p    FSQMFAQLNGINMVSYYAPMIFELAG-WVGRQAILMTGINSIVYVLSTIPPWYLVDGWGR   293
SsXUT4        GSQMFAQMNGINMVSYYAPMIFESAG-WVGRQAILMTGINSIIYIFSTIPPWYLVDSWGR   293
SsXUT7        SALGFAQFNGINIISYYAPMVFEEAG-FNNSKALLMTGINSIVYWFSTIPPWFLVDHWGR   274
BmXUT3        LIMLFQQWTGINFILYYAPFIFKQIGLSGNTISLLASGVVGIVLFLATIPAVLYIDSWGR   382
SsXUT1        LIMTFQQWTGVNFILYYAPFIFSSLGLSGNTISLLASGVVGIVMFLATIPAVLWVDRLGR   381
```

-continued

```
SsXUT3       AVMFFQQFIGCNAIIYYAPTIFTQLGMNSTTTSLLGTGLYGIVNCLSTLPAVFLIDRCGR 381
SsXUT3-A     AVMFFQQFIGCNAIIYYAPTIFTQLGMNSTTTSLLGTGLYGIVNCLSTLPAVFLIDRCGR 381
SsXU73-B     AVMFFQQFIGCNAIIYYAPTILTRLGMNSTTTSLLGTGLYGIVNCLSTLPAVFLIDRCGR 381
DhXylHP      AVMFFQQFIGCNAIIYYAPTIFSQLGMDSNTTALLGTGVYGIVNCLSTIPAIFAIDRFGR 382
SoGAL2       EVQMFQQLTFNNYFFYYGTVIFKSVGLDD---SFETSIVIGVVNFASTFFSLWTVENLGH 392
ScHXT8       MINSLQQLTGDNYFFYYGTTIFKSVGMND---SFETSIVLGIVNFASCFFSLYSVDKLGR 388
ScHXT1       MIQSLQQLTGDNYFFYYGTIVFQAVGLSD---SFETSIVFGVVNFFSTCCSLYTVDRFGR 386
ScHXT3       MIQSLQQLTGDNYFFYYGTTVFNAVGMSD---SFETSIVFGVVNFFSTCCSLYTVDRFGR 383
ScHXT7       MIQSLQQLTGDNYFFYYGTTIFKAVGLSD---SFETSIVLGIVNFASTFVGIYVVERYGR 386
ScHXT9       MIQSLQQLTGDNYFFYYGTTIFKSVGLKD---SFQTSIIIGVVNFFSSFIAVYTIERFGR 382
ScHXT2       MIQSLQQLTGNNYFFYYGTTIFNAVGMKD---SFQTSIVLGIVNFASTFVALYTVDKFGR 377
ScHXT10      VIQSLQQLTGCNYFFYYGTTIFNAVGMQD---SFETSIVLGAVNFASTFVALYIVDKFGR 370
CiGXF1       MLQSLQQLTGDNYFFYYGTTIFQAVGLKD---SFQTSIILGIVNFASTFVGIYVIERLGR 365
ScHXT13      LVQTFLQTLGENYFFFYGTTIFKSVGLTD---GRETSIVLGTVNFFSTIIAVMVVDKIGR 379
BmGXF1       TLQAGQQFTGANYFFYFGTAIFTSVGLSD---SFVTQIILGAVNFACTFLGLYILERFGR 340
ScHXT14      MIMAFQQLSGINYFFYYGTSVFKGVGIKD---PYITSIILSSVNFLSTILGIYYVEKWGH 403
BmGXS1       FIQAFQQLTGINFIFYYGTKFFKSALPGTN--PFIFSVISNVVNVVTTVPGMYMMERLGR 354
BmRGT2       FIQAFQQLTGINFIFYYGTKFFKSALPGTN--PFIFSVISNVVNVVTTVPGMYMMERLGR 730
CiGXS1       AIQAFQQLTGVNFIFYYGTTFFKRAGVN----GFTISLATNIVNVGSTIPGILLMEVLGR 342
CiGXS1-A     AIQAFQQLTGVNFIFYYGTTFFKRAGVN----GFTISLATNIVNVGSTIPGILLMEVLGR 342
CiGXS1-B     AIQAFQQLTGVNFIFYYGTTFFKRAGVN----GFTISLATNIVNVGSTIPGILLMEVLGR 342
Dh2D01474    ALQAFQQLTGVNFIFYFGTSFFKSAGIEN---EFLISLATSIVNVGMTVPGIFLIELVGR 343
Dh0D02167p   ALQAFQQLTGVNFIFYFGTSFFKSAGIEN---EFLISLATSIVNVGMTVPGIFLIELVGR 343
SsRGT2       GIQALQQLTGINFIFYYGTNFFKGSGIKN---EFLIQMATNIVNFGSTVPGILLVEIIGR 343
Y10C06424p   AIQALQQLTGINFIFYYGTEFFKKSNISN---PFLIQMITNIVNVVMTIPGIMFVDRVGR 336
Y10C08943p   SIQALQQLTGINFIFYYGTNFFKTAGIKD---PFVVSMITSAVNVAFTLPGILFVDKVGR 319
Dh2B14278p   GVQAFQQSSGINFIFYYGVNFFASSGIKN---YYLMSFVTYAVNTLFTIPGIILIEVIGR 351
EcXylE       MLSIFQQFVGINVVLYYAPEVFKTLGAST-DIALLQTIIVGVINLTFTVLAIMTVDKFGR 341
SsXUT5       TQAIVTEMAGSSVGSYYFSIILTQAGVKDSNDRLRVNIVMSSWSLVIALSGCLMFDRIGR 331
ScMAL11      CLTWVAQNSSGAVLLGYSTYFFERAGMAT-DKAFTFSLIQYCLGLAGTLCSWVISGRVGR 431
```

REFERENCES

1. Reijenga K A, et al. (2001). *Biophysical Journal* 80(2): 626-634.
2. Gardonyi M, Jeppsson M, Liden G, Gorwa-Grausland M F, & Hahn-Hagerdal B (2003). *Biotechnology and Bioengineering* 82(7):818-824.
3. Elbing K, et al. (2004). *Applied and Environmental Microbiology* 70(9):5323-5330.
4. Wahlbom C F, Otero R R C, van Zyl W H, Hahn-Hagerdal B, & Jonsson L J (2003). *Applied and Environmental Microbiology* 69(2):740-746.
5. Bengtsson O, et al. (2008). *Yeast* 25(11):835-847.
6. Jeffries T W & Jin Y S (2004). *Applied Microbiology and Biotechnology* 63(5):495-509.
7. Hahn-Hagerdal B, Karhumaa K, Fonseca C, Spencer-Martins I, & Gorwa-Grauslund M F (2007). *Applied Microbiology and Biotechnology* 74(5):937-953.
8. Martin C H, Nielsen D R, Solomon K V, & Prather K L J (2009). *Chemistry & Biology* 16(3):277-286.
9. Tyo K E J, Kocharin K, & Nielsen J (2010). *Current Opinion in Microbiology* 13(3):255-262.
10. Curran K A & Alper H S (2012). *Metabolic Engineering* 14(4):289-297.
11. Hahn-Hagerdal B, Galbe M, Gorwa-Grauslund M F, Liden G, & Zacchi G (2006). *Trends in Biotechnology* 24(12):549-556.
12. Almeida J R, et al. (2007). *Journal of Chemical Technology & Biotechnology* 82(4):340-349.
13. Van Vleet J H & Jeffries T W (2009). *Curr Opin Biotechnol* 20(3):300-306.
14. Zhang F, Rodriguez S, & Keasling J D (2011). *Current Opinion in Biotechnology* 22(6):775-783.
15. Liu L, Redden H, & Alper H S (2013). *Current Opinion in Biotechnology*. DOI: 10.1016/j.copbio.2013.03.005.

16. Hong K K & Nielsen J (2012). *Cellular and molecular life sciences: CMLS* 69(16):2671-2690.
17. Bae J Y, Laplaza J, & Jeffries T W (2008). *Applied Biochemistry and Biotechnology* 145(1-3):69-78.
18. Karhumaa K, Pahlman A K, Hahn-Hagerdal B, Levander F, & Gorwa-Grauslund M F (2009). *Yeast* 26(7):371-382.
19. Runquist D, Hahn-Hagerdal B, & Bettiga M (2010). *Applied and Environmental Microbiology* 76(23):7796-7802.
20. Krahulec S, Klimacek M, & Nidetzky B (2012). *Journal of Biotechnology* 158(4):192-202.
21. Lee S M, Jellison T, & Alper H S (2012). Applied and Environmental Microbiology 78(16):5708-5716.
22. Scalcinati G, et al. (2012). *FEMS Yeast Res* 12(5):582-597.
23. Jojima T, Omumasaba C A, Inui M, & Yukawa H (2010). *Applied Microbiology and Biotechnology* 85(3):471-480.
24. Young E, Lee S M, & Alper H (2010). *Biotechnology for Biofuels* 3(24):24.
25. Boles E & Hollenberg C P (1997). *FEMS Microbiology Reviews* 21(1):85-111.
26. Wieczorke R, et al. (1999). *FEBS Letters* 464(3):123-128.
27. Pao S S, Paulsen I T, & Saier M H, Jr. (1998). *Microbiology and Molecular Biology Reviews* 62(1):1-34.
28. Ozcan S & Johnston M (1999). *Microbiology and Molecular Biology Reviews* 63(3):554.
29. Sedlak M & Ho N W Y (2004) *Char. Yeast* 21(8):671-684.
30. Subtil T & Boles E (2012). *Biotechnology for Biofuels* 5:14.
31. Leandro M J, Goncalves P, & Spencer-Martins I (2006). *Biochemical Journal* 395:543-549.
32. Saloheimo A, et al. (2007). *Applied Microbiology and Biotechnology* 74(5):1041-1052.
33. Hector R E, Qureshi N, Hughes S R, & Cotta M A (2008). *Applied Microbiology and Biotechnology* 80(4):675-684.
34. Katahira S, et al. (2008). *Enzyme and Microbial Technology* 43(2):115-119.
35. Du J, Li S J, & Zhao H M (2010). *Molecular Biosystems* 6(11):2150-2156.
36. Young E, Poucher A, Corner A, Bailey A, & Alper H (2011). *Applied and Environmental Microbiology* 77(10):3311-3319.
37. Leandro M J, Fonseca C, & Goncalves P (2009). *FEMS Yeast Research* 9(4):511-525.
38. Young E M, Corner A D, Huang H S, & Alper H S (2012) A. *Metabolic Engineering* 14(4):401-411.
39. Kasahara T & Kasahara M (2010). *Journal of Biological Chemistry* 285(34):26263-26268.
40. Ha S J, et al. (2013). *Applied and Environmental Microbiology* 79(5):1500-1507.
41. Sun L, et al. (2012) Cry. *Nature* 490(7420):361-366.
42. Hamacher T, Becker J, Gardonyi M, Hahn-Hagerdal B, & Boles E (2002). *Microbiology* 148(Pt 9):2783-2788.
43. Kasahara T, Shimogawara K, & Kasahara M (2011). *Biochemistry* 50(40):8674-8681.
44. Davis E O & Henderson P J F (1987). *Journal of Biological Chemistry* 262(29):13928-13932.
45. Subtil T & Boles E (2011). Biotechnology for Biofuels 4:38.
46. Sambrook J (2000) Molecular Cloning: A Laboratory Manual. ed Russell D W (Cold Spring Harbor Laboratory Press, Cold Spring Harbor, N.Y.).
47. Mumberg D, Muller R, & Funk M (1995). *Gene* 156(1):119-122.

---

What is claimed is:

1. A non-naturally occurring, recombinant xylose transporter protein comprising a transporter motif sequence corresponding to amino acid residue positions 36, 37, 38, 39, 40, and 41 of SEQ ID NO: 1 of *Candida intermedia* GXS1 protein, wherein said transporter motif sequence is mutated to -G-G/F-$X^1$-$X^2$-$X^3$-G-(SEQ ID NO: 29);
wherein,
$X^1$ is D, C, G, H, I, L, or F;
$X^2$ is A, D, C, E, G, H, or I;
$X^3$ is N, C, Q, F, G, L, M, S, T, or P; and
wherein, said transporter motif sequence is not -G-G-L-I-F-G- (SEQ ID NO: 2) or -G-G-F-I-F-G-(SEQ ID NO: 3);
and further wherein said transporter motif sequence allows transport of xylose into a cell.

2. The non-naturally occurring, recombinant xylose transporter protein of claim 1, wherein $X^1$ is F, $X^2$ is I, and $X^3$ is M or S.

3. The non-naturally occurring, recombinant xylose transporter protein of claim 1, wherein said transporter motif sequence is -G-G-F-I-M-G-(SEQ ID NO: 4), -G-F-F-I-M-G-(SEQ ID NO: 5), -G-G-F-I-S-G-(SEQ ID NO: 6), -G-F-F-I-S-G-(SEQ ID NO: 7), -G-G-F-I-T-G-(SEQ ID NO: 8), -G-F-F-I-T-G-(SEQ ID NO: 9), -G-G-F-L-M-G-(SEQ ID NO: 10), -G-F-F-L-M-G-(SEQ ID NO: 11), -G-G-F-L-S-G-(SEQ ID NO: 12), -G-F-F-L-S-G-(SEQ ID NO: 13), -G-G-F-L-T-G-(SEQ ID NO: 14), -G-F-F-L-T-G-(SEQ ID NO: 15), -G-G-F-H-M-G-(SEQ ID NO: 16), -G-F-F-H-M-G-(SEQ ID NO: 17), -G-G-F-H-S-G-(SEQ ID NO: 18), -G-F-F-H-S-G-(SEQ ID NO: 19), -G-G-F-H-T-G-(SEQ ID NO: 20) or -G-F-F-H-T-G-(SEQ ID NO: 21).

4. The non-naturally occurring, recombinant xylose transporter protein of claim 3 further comprising a mutation of an amino acid at the residue position corresponding to 297 of *Candida intermedia* GXS1 protein.

5. The non-naturally occurring, recombinant xylose transporter protein of claim 4, wherein said amino acid at the residue position corresponding to 297 of *Candida intermedia* GXS1 protein is substituted with a Met, Ala, Ser, or Asn residue.

* * * * *

SEQUENCE LISTING

<160> NUMBER OF SEQ ID NOS: 32

<210> SEQ ID NO 1
<211> LENGTH: 522
<212> TYPE: PRT
<213> ORGANISM: Candida intermedia

<400> SEQUENCE: 1

```
Met Gly Leu Glu Asp Asn Arg Met Val Lys Arg Phe Val Asn Val Gly
1               5                   10                  15

Glu Lys Lys Ala Gly Ser Thr Ala Met Ala Ile Ile Val Gly Leu Phe
            20                  25                  30

Ala Ala Ser Gly Gly Val Leu Phe Gly Tyr Asp Thr Gly Thr Ile Ser
        35                  40                  45

Gly Val Met Thr Met Asp Tyr Val Leu Ala Arg Tyr Pro Ser Asn Lys
    50                  55                  60

His Ser Phe Thr Ala Asp Glu Ser Ser Leu Ile Val Ser Ile Leu Ser
65                  70                  75                  80

Val Gly Thr Phe Phe Gly Ala Leu Cys Ala Pro Phe Leu Asn Asp Thr
                85                  90                  95

Leu Gly Arg Arg Trp Cys Leu Ile Leu Ser Ala Leu Ile Val Phe Asn
            100                 105                 110

Ile Gly Ala Ile Leu Gln Val Ile Ser Thr Ala Ile Pro Leu Leu Cys
        115                 120                 125

Ala Gly Arg Val Ile Ala Gly Phe Gly Val Gly Leu Ile Ser Ala Thr
    130                 135                 140
```

Ile Pro Leu Tyr Gln Ser Glu Thr Ala Pro Lys Trp Ile Arg Gly Ala
145                 150                 155                 160

Ile Val Ser Cys Tyr Gln Trp Ala Ile Thr Ile Gly Leu Phe Leu Ala
                165                 170                 175

Ser Cys Val Asn Lys Gly Thr Glu His Met Thr Asn Ser Gly Ser Tyr
            180                 185                 190

Arg Ile Pro Leu Ala Ile Gln Cys Leu Trp Gly Leu Ile Leu Gly Ile
        195                 200                 205

Gly Met Ile Phe Leu Pro Glu Thr Pro Arg Phe Trp Ile Ser Lys Gly
    210                 215                 220

Asn Gln Glu Lys Ala Ala Glu Ser Leu Ala Arg Leu Arg Lys Leu Pro
225                 230                 235                 240

Ile Asp His Pro Asp Ser Leu Glu Glu Leu Arg Asp Ile Thr Ala Ala
                245                 250                 255

Tyr Glu Phe Glu Thr Val Tyr Gly Lys Ser Ser Trp Ser Gln Val Phe
                260                 265                 270

Ser His Lys Asn His Gln Leu Lys Arg Leu Phe Thr Gly Val Ala Ile
            275                 280                 285

Gln Ala Phe Gln Gln Leu Thr Gly Val Asn Phe Ile Phe Tyr Tyr Gly
        290                 295                 300

Thr Thr Phe Phe Lys Arg Ala Gly Val Asn Gly Phe Thr Ile Ser Leu
305                 310                 315                 320

Ala Thr Asn Ile Val Asn Val Gly Ser Thr Ile Pro Gly Ile Leu Leu
                325                 330                 335

Met Glu Val Leu Gly Arg Arg Asn Met Leu Met Gly Gly Ala Thr Gly
                340                 345                 350

Met Ser Leu Ser Gln Leu Ile Val Ala Ile Val Gly Val Ala Thr Ser
            355                 360                 365

Glu Asn Asn Lys Ser Ser Gln Ser Val Leu Val Ala Phe Ser Cys Ile
370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
                405                 410                 415

Cys Thr Ala Ser Asn Trp Leu Trp Asn Trp Gly Ile Ala Tyr Ala Thr
            420                 425                 430

Pro Tyr Met Val Asp Glu Asp Lys Gly Asn Leu Gly Ser Asn Val Phe
        435                 440                 445

Phe Ile Trp Gly Gly Phe Asn Leu Ala Cys Val Phe Phe Ala Trp Tyr
    450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
                485                 490                 495

Lys His Ser Phe Arg Glu Gln Val Asp Gln Met Asp Ser Lys Thr
            500                 505                 510

Glu Ala Ile Met Ser Glu Glu Ala Ser Val
        515                 520

<210> SEQ ID NO 2
<211> LENGTH: 6
<212> TYPE: PRT
<213> ORGANISM: Artificial Sequence
<220> FEATURE:

```
<223> OTHER INFORMATION: Synthetic Construct

<400> SEQUENCE: 2

Gly Gly Leu Ile Phe Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Gly Gly Phe Ile Phe Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gly Gly Phe Ile Met Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Gly Phe Phe Ile Met Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Gly Gly Phe Ile Ser Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Gly Phe Phe Ile Ser Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 8

Gly Gly Phe Ile Thr Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Gly Phe Phe Ile Thr Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Gly Gly Phe Leu Met Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Gly Phe Phe Leu Met Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Gly Phe Leu Ser Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Gly Phe Phe Leu Ser Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 14

Gly Gly Phe Leu Thr Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Gly Phe Phe Leu Thr Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Gly Gly Phe His Met Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Gly Phe Phe His Met Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Gly Gly Phe His Ser Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Gly Phe Phe His Ser Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20
```

```
Gly Gly Phe His Thr Gly
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Gly Phe Phe His Thr Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Gly Gly Leu Val Tyr Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Gly Gly Thr Pro Thr Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Gly Gly Arg Pro Thr Gly
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Gly Phe Arg Pro Thr Gly
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct

<400> SEQUENCE: 26
```

```
Gly Gly Thr Pro Thr Gly
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Gly Phe Thr Pro Thr Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Gly Gly Thr Pro Thr Gly
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: x
<222> LOCATION: (2)..(5)
<223> OTHER INFORMATION: X can be any naturally occurring amino acid

<400> SEQUENCE: 29

Gly Xaa Xaa Xaa Xaa Gly
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: X
<222> LOCATION: (2)..(5)
<223> OTHER INFORMATION: X can be any naturally occurring amino acid

<400> SEQUENCE: 30

Gly Xaa Xaa Xaa Xaa Gly
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: X
<222> LOCATION: (3)..(5)
<223> OTHER INFORMATION: X can be any naturally occurring amino acid

<400> SEQUENCE: 31

Ser Gly Xaa Xaa Xaa Gly
1               5
```

```
<210> SEQ ID NO 32
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: X
<222> LOCATION: (2)..(4)
<223> OTHER INFORMATION: X can be any naturally occurring amino acid

<400> SEQUENCE: 32

Gly Xaa Xaa Xaa Phe Gly
1               5
```